United States Patent
Johns et al.

(10) Patent No.: US 10,774,035 B2
(45) Date of Patent: Sep. 15, 2020

(54) PREPARATION OF AMINO ACIDS AND AMINO ACID DERIVATIVES

(71) Applicant: Umicore AG & Co. KG, Hanau-Wolfgang (DE)

(72) Inventors: Adam M. Johns, Claremont, CA (US); Jessica R. Herron, Pasadena, CA (US); Richard L. Pederson, San Gabriel, CA (US); Thay A. Ung, Monrovia, CA (US); Ba L. Tran, Kennewick, WA (US); Daryl P. Allen, Pasadena, CA (US)

(73) Assignee: Umicore AG & Co. KG (DE)

( * ) Notice: Subject to any disclaimer, the term of this patent is extended or adjusted under 35 U.S.C. 154(b) by 0 days.

(21) Appl. No.: 16/335,342

(22) PCT Filed: Sep. 6, 2017

(86) PCT No.: PCT/US2017/050185
§ 371 (c)(1),
(2) Date: Mar. 21, 2019

(87) PCT Pub. No.: WO2018/057290
PCT Pub. Date: Mar. 29, 2018

(65) Prior Publication Data
US 2019/0276388 A1 Sep. 12, 2019

Related U.S. Application Data

(60) Provisional application No. 62/398,905, filed on Sep. 23, 2016.

(51) Int. Cl.
| | |
|---|---|
| C07C 227/08 | (2006.01) |
| B01J 31/22 | (2006.01) |
| C07C 227/04 | (2006.01) |
| C07C 229/08 | (2006.01) |
| C07C 67/303 | (2006.01) |
| C07C 67/00 | (2006.01) |
| C07C 67/313 | (2006.01) |
| C07C 67/343 | (2006.01) |
| B01J 31/20 | (2006.01) |
| B01J 31/02 | (2006.01) |
| B01J 31/18 | (2006.01) |
| B01J 31/24 | (2006.01) |

(52) U.S. Cl.
CPC ............ *C07C 227/04* (2013.01); *B01J 31/22* (2013.01); *C07C 67/00* (2013.01); *C07C 67/303* (2013.01); *C07C 67/313* (2013.01); *C07C 67/343* (2013.01); *C07C 227/08* (2013.01); *C07C 229/08* (2013.01); *B01J 31/0244* (2013.01); *B01J 31/189* (2013.01); *B01J 31/20* (2013.01); *B01J 31/2226* (2013.01); *B01J 31/2265* (2013.01); *B01J 31/2278* (2013.01); *B01J 31/2404* (2013.01); *B01J 2231/349* (2013.01); *B01J 2231/543* (2013.01); *B01J 2531/0244* (2013.01); *B01J 2531/821* (2013.01)

(58) Field of Classification Search
CPC ... C07C 227/04; C07C 229/08; C07C 67/303; C07C 67/343; B01J 31/22; B01J 31/2273
See application file for complete search history.

(56) References Cited

U.S. PATENT DOCUMENTS

| | | |
|---|---|---|
| 5,312,940 A | 5/1994 | Grubbs et al. |
| 5,342,909 A | 8/1994 | Grubbs et al. |
| 5,977,393 A | 11/1999 | Grubbs et al. |
| 6,284,852 B1 | 9/2001 | Lynn et al. |
| 6,486,279 B2 | 11/2002 | Lynn et al. |
| 6,552,139 B1 | 4/2003 | Herrmann et al. |
| 6,613,910 B2 | 9/2003 | Grubbs et al. |
| 6,620,955 B1 | 9/2003 | Pederson et al. |
| 6,635,768 B1 | 10/2003 | Herrmann et al. |
| 6,787,620 B2 | 9/2004 | Herrmann et al. |
| 6,838,489 B2 | 1/2005 | Bell et al. |
| 6,921,735 B2 | 7/2005 | Hoveyda et al. |
| 7,026,495 B1 | 4/2006 | Pederson et al. |
| 7,294,717 B2 | 11/2007 | Herrmann et al. |
| 7,378,528 B2 | 5/2008 | Herrmann et al. |
| 7,652,145 B2 | 1/2010 | Herrmann et al. |
| 7,671,224 B2 | 3/2010 | Winde et al. |
| 7,687,635 B2 | 3/2010 | Verpoort et al. |

(Continued)

FOREIGN PATENT DOCUMENTS

| | | |
|---|---|---|
| EP | 1757613 B1 | 1/2011 |
| EP | 1577282 B1 | 6/2011 |

(Continued)

OTHER PUBLICATIONS

Behr, A. et al., The cross-metathesis of methyl oleate with cis-2-butene-1,4-diyldizcetate and the influence of protecting groups, 2011, Beilstein Journal of Organic Chemistry, vol. 7, pp. 1-8 (Year: 2011).*

(Continued)

Primary Examiner — Yate' K Cutliff
(74) Attorney, Agent, or Firm — Faegre Drinker Biddle & Reath LLP

(57) ABSTRACT

The invention relates to a method for synthesizing amino acids or amino acid derivatives involving cross metathesis of functionalized olefins and a tandem amination-reduction process. Amino acids and amino acid derivatives present many interesting physical and chemical properties finding many uses in the automotive, fuel, electronic, and textile industries.

20 Claims, No Drawings

(56) References Cited

U.S. PATENT DOCUMENTS

| | | |
|---|---|---|
| 8,318,965 B2 | 11/2012 | Grela et al. |
| 8,748,651 B2 | 6/2014 | Dubois |
| 9,790,168 B2 | 10/2017 | Dubois et al. |
| 2003/0055262 A1 | 3/2003 | Grubbs et al. |
| 2007/0043188 A1 | 2/2007 | Schaubroeck et al. |
| 2007/0185343 A1 | 8/2007 | Verpoort et al. |
| 2008/0293905 A9 | 11/2008 | Schaubroeck et al. |
| 2011/0105774 A1 | 5/2011 | Dubois |
| 2013/0165672 A1 | 6/2013 | Klasovsky et al. |
| 2014/0046065 A1* | 2/2014 | Milstein ............... C07B 43/04 546/23 |
| 2014/0187808 A1 | 7/2014 | Couturier et al. |
| 2014/0323684 A1 | 10/2014 | Dubois et al. |

FOREIGN PATENT DOCUMENTS

| | | |
|---|---|---|
| WO | WO-0214376 A2 | 2/2002 |
| WO | WO-02079208 A2 | 10/2002 |
| WO | WO-0311455 A1 | 2/2003 |
| WO | WO-2005121158 A1 | 12/2005 |
| WO | WO-2008145941 A2 | 12/2008 |
| WO | WO-2010018570 A1 | 2/2010 |
| WO | WO-2010037550 A1 | 4/2010 |
| WO | WO-2011069134 A2 | 6/2011 |
| WO | WO-2014122412 A1 | 8/2014 |
| WO | WO-2015200200 A1 * | 12/2015 ............... C07C 6/04 |

OTHER PUBLICATIONS

Behr, A., et al., "The cross-metathesis of methyl oleate with cis-2-butene-1,4-diyldiacetate and the influence of protecting groups", Beilstein Journal of Organic Chemistry 2011, vol. 7, pp. 1-8.

International Search Report for PCT/US2017/050185 dated Nov. 16, 2017.

Written Opinion of the International Searching Authority for PCT/US2017/050185 dated Nov. 16, 2017.

* cited by examiner

PREPARATION OF AMINO ACIDS AND AMINO ACID DERIVATIVES

CROSS-REFERENCE TO RELATED APPLICATIONS

This application is a national stage application (under 35 U.S.C. § 371) of PCT/US2017/050185, filed Sep. 6, 2017, which claims benefit of U.S. Application No. 62/398,905, filed Sep. 23, 2016, both of which are incorporated herein by reference in their entirety.

TECHNICAL FIELD

The invention relates to a method for synthesizing amino acids or amino acid derivatives involving cross metathesis of functionalized olefins and a tandem amination-reduction process. Amino acids and amino acid derivatives present many interesting physical and chemical properties finding many uses in the automotive, fuel, electronic, and textile industries.

BACKGROUND

Olefin metathesis has emerged as a unique and powerful transformation for the interconversion of olefinic hydrocarbons, namely due to the development of well-defined catalysts. See Grubbs, R. H. *Handbook of Metathesis*, Wiley-VCH: Weinheim, Germany (2003). The exceptionally wide scope of substrates and functional group tolerances makes olefin metathesis a valuable technique that quickly and efficiently produces otherwise hard to make molecules, compared to traditional synthetic organic techniques. In particular, certain Ruthenium and Osmium metal carbene compounds known as "Grubbs catalysts," have been identified as effective catalysts for olefin metathesis reactions, such as, cross metathesis (CM), ring-closing metathesis (RCM), ring-opening metathesis (ROM), ring-opening cross metathesis (ROCM), ring-opening metathesis polymerization (ROMP) and acyclic diene metathesis (ADMET) polymerization. The use of such Ruthenium carbene complexes has greatly expanded the scope of olefin metathesis due to increased tolerance of organic functionality, moisture, and oxygen.

Polyamide 11 (PA11) or Nylon 11 and Polyamide 12 (PA12) or Nylon 12 are of commercial importance. Arkema sells PA11 and PA12 under the trade name of Rilsan® PA11 and Rilsan® PA12 respectively, while Evonik sells PA12 under the trade name VESTAMID® L. These high-performance polyamides possess a desirable combination of thermal, physical, chemical, and mechanical properties for industrial products, such as electrical cables, and automotive pneumatic and hydraulic hoses.

PA11 is produced from 10-undecenoic acid, derived from castor beans, and is one of the few commercially available polymers derived from a renewable resource. The limited supply of castor oil restricts the amount of PA11 produced.

PA12, which is used as a coating on fuel and braking systems on most passenger cars worldwide, is derived from cyclododecatriene (CDT).

U.S. Pat. No. 8,748,651 teaches the synthesis of long chain amino acids or esters from natural unsaturated fatty acids.

U.S. Pat. No. 8,748,651 describes the use of high catalyst loadings of olefin metathesis catalysts in the cross metathesis with acrylate.

International Patent Application Publication No. WO 2008/145941 teaches the conjugated process for the production of nitriles and/or fatty amines and of polyol carbonates by the reaction of urea with a polyol to liberate ammonia.

International Patent Application Publication No. WO 2014/122412 teaches the synthesis of amino acids from the cross metathesis of unsaturated fatty acids and esters with acrylonitrile or the cross metathesis of 9-decenenitrile and acrylates.

U.S. Patent Application Publication No. US 2014/0187808 teaches the synthesis of amino acids starting from the cross metathesis of 9-decenenitrile and acrylates.

U.S. Patent Application Publication No. US 2014/0323684 describes a method for synthesizing a ω-amino acid compound having formula $HOOC-R^b-CH_2NH_2$.

X. Miao; C. Fischmeister; P. H. Dixneuf; C. Bruneau; J.-L. Dubois; J.-L. Couturier *Green Chem.* (2012), 14, 2179 describes the synthesis of 12-amino acid by the cross metathesis of methyl 10-undecenoate and acrylonitrile, followed by hydrogenation to yield 12-amino acid.

R. Malacea; C. Fischmeister; C. Bruneau; J.-L. Dubois; J.-L. Couturier; P. H. Dixneuf *Green Chem.* (2009), 11, 152 describes the cross metathesis of acrylonitrile or fumaronitrile and unsaturated acid or ester, followed by hydrogenation to yield amino acids.

C. Bruneau; C. Fischmeister; X. Miao; R. Malacea; P. H. Dixneuf; *Eur. J Lipid Sci. Technol.* (2010), 112, 3-9 is a review article, which describes methyl 10-undecenoate and octadec-9-enoic diester cross metathesized with acrylonitrile or fumaronitrile to produce the unsaturated ester nitrile of the formula $NCCH=CH(CH_2)_t CO_2R$.

X. Miao; R. Malacea; C. Fischmeister; C. Bruneau; P. H. Dixneuf; *Green Chem.* (2011), 13, 2911 teaches the slow addition of metathesis catalyst to methyl 10-undecenoate or octadec-9-enoic diester with acrylonitrile or fumaronitrile to produce the unsaturated ester nitrile of the formula $NCCH=CH(CH_2)_d CO_2R$.

X. Miao; A. Blokhin; A. Pasynskii; S. Nefedov; S. N. Osipov; T. Roisnel; C. Bruneau; P. H. Dixneuf in *Organometallics* (2010), 29, 5257 teaches the synthesis of unsaturated ester nitrile of the formula $NCCH=CH(CH_2)_n CO_2R$.

Many literature processes have been reported to produce amino acids or amino acid derivatives but all of these use high metathesis catalysts loadings to obtain sufficient yields or use toxic reagents with their metathesis catalyst. Therefore there is a need for an environmentally friendly process to produce amino acids or amino acid derivatives without high catalyst loadings or the use of toxic reagents. This invention addresses this need.

SUMMARY OF THE INVENTION

The invention relates to an efficient method for synthesizing amino acids and amino acid derivatives involving cross metathesis of functionalized olefins and a tandem amination-reduction process.

The invention generally relates to the synthesis of amino acids or amino acid derivatives by a process of cross metathesis of an unsaturated acid or ester with a protected 2-butene-1,4-diol derivative, removal of the alcohol protecting group yielding the alcohol derivative, subjecting the alcohol derivative to a tandem amination-reduction process in the presence of a Ruthenium pincer complex represented by the structure of Formula 4, to yield the corresponding amino acid or the amino acid derivative. Typically, the removal of the alcohol protecting group is done in the presence of a base in an alcohol at room temperature.

The Ruthenium pincer complex is represented by the structure of Formula 4:

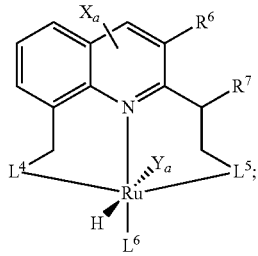

Formula 4 wherein:

$L^4$ and $L^5$ are each independently selected from the group consisting of phosphine ($PR^aR^b$), amine ($NR^aR^b$), imine, sulfide ($SR^d$), thiol (SH), sulfoxide ($S(=O)R^d$) and, heteroaryl containing at least one heteroatom selected from nitrogen and sulfur; arsine ($AsR^aR^b$), stibine ($SbR^aR^b$), and an N-heterocyclic carbene represented by the structures:

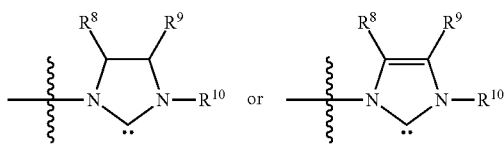

$L^6$ is a mono-dentate two-electron donor, such as CO, $PR^aR^bR^c$, $NO^+$, $AsR^aR^bR^c$, $SbR^aR^bR^c$, $SR^aR^b$, nitrile ($R^dCN$), isonitrile ($R^dNC$), $N_2$, $PF_3$, CS, heteroaryl (e.g., pyridine, thiophene), tetrahydrothiophene, and N-heterocyclic carbene;

$R^6$ and $R^7$ are either each hydrogen or together with the carbons to which they are attached represent a phenyl ring which is fused to the quinolinyl moiety represented by the structure of Formula 4 so as to form an acridinyl moiety;

$R^a$, $R^b$, $R^c$, $R^d$, $R^8$, $R^9$, and $R^{10}$ are each independently alkyl, cycloalkyl, aryl, heterocyclyl, heteroaryl, alkylcycloalkyl, alkylaryl, alkylheterocyclyl, or alkylheteroaryl;

$Y_a$ is a monoanionic ligand, such as halogen, —$OCOR^d$, —$OCOCF_3$, —$OSO_2R^d$, —$OSO_2CF_3$, —CN, —OH, —$OR^d$, and —$NR^d{}_2$; or a neutral solvent molecule, such as $NH_3$, $NR_3$, and $R^d{}_2NSO_2R^d$, wherein $R^d$ is defined above; and when $Y_a$ is neutral, the whole molecule carries a positive charge; and $X_a$ represents one, two, three, four, five, six, or seven substituents positioned at any carbon atom on the acridinyl moiety (in the case where $R^6$ and $R^7$ together with the carbons to which they are attached represent a phenyl ring which is fused to the quinolinyl moiety represented by the structure of Formula 4); or one, two, three, four, or five substituents positioned on any carbon atom on the quinolinyl moiety (in the case where $R^6$ and $R^7$ are each hydrogen), and is selected from the group consisting of hydrogen, alkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support (e.g., silica), and a polymeric moiety (e.g., polystyrene).

In one embodiment, the Ruthenium pincer complex represented by the structure of Formula 4 is [RuHCl(A-iPr-PNP)(CO)], Chlorocarbonylhydrido[4,5-bis-(di-i-propylphosphino methyl) acridine] Ruthenium (II), represented by the structure:

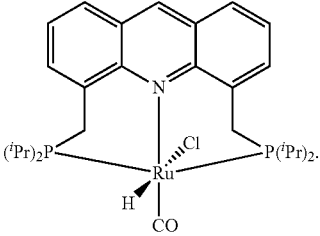

In another embodiment, the Ruthenium pincer complex represented by the structure of Formula 4 is [RuHCl(A-Cy-PNP)(CO)], Chlorocarbonylhydrido[4,5-bis-(di-cyclohexyl phosphinomethyl)acridine] Ruthenium (II), represented by the structure:

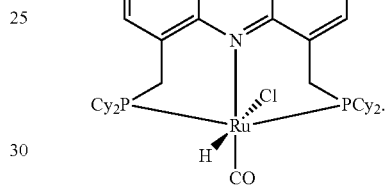

In another aspect, the invention relates to the synthesis of an amino acid or an amino acid derivative by a process of cross metathesis of an unsaturated acid or ester with a 1,4-alcohol protected-2-butene derivative, in the presence of at least one metal carbene olefin metathesis catalyst, followed by removal of the alcohol protecting group to yield the alcohol derivative, and subjecting the alcohol derivative to a tandem amination-reduction process in the presence of a Ruthenium pincer complex represented by the structure of Formula 4, to yield the amino acid or the amino acid derivative.

In another aspect, the invention relates to the synthesis of an amino acid or an amino acid derivative, by a process of cross metathesis of an unsaturated acid or ester with a 1,4-alcohol protected-2-butene derivative, in the presence of at least one Group 8 transition metal complex, followed by removal of the alcohol protecting group to yield the alcohol derivative, and subjecting the alcohol derivative to a tandem amination-reduction process, in the presence of a Ruthenium pincer complex represented by the structure of Formula 4, to yield the amino acid or the amino acid derivative.

The invention relates to a process for synthesizing an amino acid or an amino acid derivative represented by the structure of Formula 1:

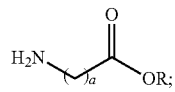

Formula 1 comprising:

(a) subjecting an olefinic substrate represented by the structure of Formula 2:

Formula 2

to a cross metathesis reaction with a cross metathesis substrate represented by the structure of formula

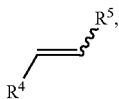

in the presence of at least one metal carbene olefin metathesis catalyst, to form an unsaturated protected alcohol intermediate represented by the structure of Formula 2a:

Formula 2a

(b) subjecting the unsaturated protected alcohol intermediate represented by the structure of Formula 2a to hydrolysis in basic conditions to yield an unsaturated alcohol represented by the structure of Formula 3:

Formula 3

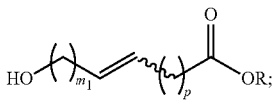

and;

(c) converting the unsaturated alcohol represented by the structure of Formula 3, to an amino acid or to an amino acid derivative represented by the structure of Formula 1, by subjecting the unsaturated alcohol represented by the structure of Formula 3 to a tandem amination-reduction, wherein the tandem amination-reduction is carried out in the presence of ammonia, hydrogen, and a Ruthenium pincer complex represented by the structure of Formula 4;

wherein:

R is —H, optionally substituted $C_1$-$C_{12}$ alkyl, optionally substituted $C_6$-$C_{10}$ aryl, optionally substituted heterocycle, or optionally substituted $C_5$-$C_{10}$ cycloalkyl;

$R^1$ is —H, —$CH_3$, or —COOR;

$R^2$ is —$OR^3$;

$R^3$ is optionally substituted —CO($C_1$-$C_{12}$ alkyl), optionally substituted —CO($C_5$-$C_{10}$ cycloalkyl), optionally substituted —CO($C_6$-$C_{10}$ aryl), or optionally substituted —CO($C_5$-$C_{10}$ heterocycle);

$R^4$ is —H or —$(CH_2)_{m_1}OR^3$;

$R^5$ is —$(CH_2)_{m_1}OR^3$;

a is 3, 4, 5, 6, 7, 8, 9, 10, 11, 12, 13, 14, 15, 16, 17, 18, 19, 20, 21, or 22;

m is 0, 1, 2, 3, 4, 5, 6, 7, 8, 9, 10, 11, 12, 13, 14, 15, 16, 17, 18, or 19;

$m_1$ is 1, 2, 3, 4, 5, 6, 7, 8, 9, 10, 11, 12, 13, 14, 15, 16, 17, 18, or 19;

p is 0, 1, 2, 3, 4, 5, 6, 7, 8, 9, 10, 11, 12, 13, 14, 15, 16, 17, 18, or 19;

$L^4$ and $L^5$ are each independently selected from the group consisting of phosphine ($PR^aR^b$), amine ($NR^aR^b$), imine, sulfide ($SR^d$), thiol (SH), sulfoxide ($S(=O)R^d$), heteroaryl containing at least one heteroatom selected from nitrogen and sulfur; arsine ($AsR^aR^b$), stibine ($SbR^aR^b$), and an N-heterocyclic carbene represented by the structures:

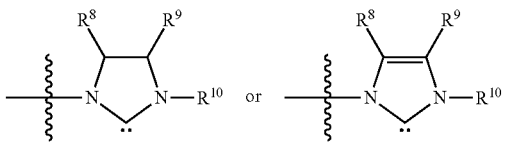

$L^6$ is a mono-dentate two-electron donor, such as CO, $PR^aR^bR^c$, $NO^+$, $AsR^aR^bR^c$, $SbR^aR^bR^c$, $SR^aR^b$, nitrile ($R^dCN$), isonitrile ($R^dNC$), $N_2$, $PF_3$, CS, heteroaryl (e.g., pyridine, thiophene), tetrahydrothiophene, and N-heterocyclic carbene;

$R^6$ and $R^7$ are either each hydrogen or together with the carbons to which they are attached represent a phenyl ring which is fused to the quinolinyl moiety represented by the structure of Formula 4 so as to form an acridinyl moiety;

$R^a$, $R^b$, $R^c$, $R^d$, $R^8$, $R^9$, and $R^{10}$ are each independently alkyl, cycloalkyl, aryl, heterocyclyl, heteroaryl, alkylcycloalkyl, alkylaryl, alkylheterocyclyl, or alkylheteroaryl;

$Y^a$ is a monoanionic ligand, such as halogen, —$OCOR^d$, —$OCOCF_3$, —$OSO_2R^d$, —$OSO_2CF_3$, —CN, —OH, —$OR^d$, and —$NR^d_2$; or a neutral solvent molecule, such as $NH_3$, $NR_3$, and $R^d_2NSO_2R^d$, wherein $R^d$ is defined above; and when $Y^a$ is neutral, the whole molecule carries a positive charge;

$X^a$ represents one, two, three, four, five, six, or seven substituents positioned at any carbon atom on the acridinyl moiety (in the case where $R^6$ and $R^7$ together with the carbons to which they are attached represent a phenyl ring which is fused to the quinolinyl moiety represented by the structure of Formula 4); or one, two, three, four, or five substituents positioned on any carbon atom on the quinolinyl moiety (in the case where $R^6$ and $R^7$ are each hydrogen), and is selected from the group consisting of hydrogen, alkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support (e.g., silica), and a polymeric moiety (e.g., polystyrene); and with the proviso that the sum of any combination of $m_1$ and p is 1, 2, 3, 4, 5, 6, 7, 8, 9, 10, 11, 12, 13, 14, 15, 16, 17, 18, 19, or 20.

The invention also relates to a process for synthesizing an amino acid or an amino acid derivative represented by the structure of Formula 1, comprising:

(a) subjecting an olefinic substrate represented by the structure of Formula 2 to a cross metathesis reaction with a cross metathesis substrate represented by the structure of formula

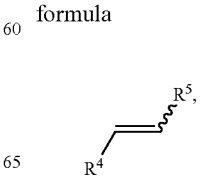

in the presence of at least one metal carbene olefin metathesis catalyst, to form an unsaturated protected alcohol intermediate represented by the structure of Formula 2a;

(b) subjecting the unsaturated protected alcohol intermediate represented by the structure of Formula 2a to hydrolysis in basic conditions to yield an unsaturated alcohol represented by the structure of Formula 3; and (c) converting the unsaturated alcohol represented by the structure of Formula 3, to an amino acid or to an amino acid derivative represented by the structure of Formula 1, by subjecting the unsaturated alcohol represented by the structure of Formula 3 to a tandem amination-reduction, wherein the tandem amination-reduction is carried out in the presence of a Ruthenium pincer complex represented by the structure of Formula 4;

wherein:

R is —H, optionally substituted $C_1$-$C_{12}$ alkyl, optionally substituted $C_6$-$C_{10}$ aryl, optionally substituted heterocycle, or optionally substituted $C_5$-$C_{10}$ cycloalkyl;

$R^1$ is —H, —$CH_3$, or —COOR;

$R^2$ is —$OR^3$;

$R^3$ is optionally substituted —CO($C_1$-$C_{12}$ alkyl), optionally substituted —CO($C_5$-$C_{10}$ cycloalkyl), optionally substituted —CO($C_6$-$C_{10}$ aryl), or optionally substituted —CO($C_5$-$C_{10}$ heterocycle);

$R^4$ is —H or —$(CH_2)_{m1}OR^3$;

$R^5$ is —$(CH_2)_{m1}OR^3$;

a is 3, 4, 5, 6, 7, 8, 9, 10, 11, 12, 13, 14, 15, 16, 17, 18, 19, 20, 21, or 22;

m is 0, 1, 2, 3, 4, 5, 6, 7, 8, 9, 10, 11, 12, 13, 14, 15, 16, 17, 18, or 19;

$m_1$ is 1, 2, 3, 4, 5, 6, 7, 8, 9, 10, 11, 12, 13, 14, 15, 16, 17, 18, or 19;

p is 0, 1, 2, 3, 4, 5, 6, 7, 8, 9, 10, 11, 12, 13, 14, 15, 16, 17, 18, or 19;

$L^4$ and $L^5$ are each independently selected from the group consisting of phosphine ($PR^aR^b$), amine ($NR^aR^b$), imine, sulfide ($SR^d$), thiol (SH), sulfoxide ($S(=O)R^d$), heteroaryl containing at least one heteroatom selected from nitrogen and sulfur; arsine ($AsR^aR^b$), stibine ($SbR^aR^b$), and an N-heterocyclic carbene represented by the structures:

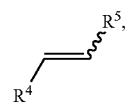

$L^6$ is a mono-dentate two-electron donor, such as CO, $PR^aR^bR^c$, $NO^+$, $AsR^aR^bR^c$, $SbR^aR^bR^c$, $SR^aR^b$, nitrile ($R^dCN$), isonitrile ($R^dNC$), $N_2$, $PF_3$, CS, heteroaryl (e.g., pyridine, thiophene), tetrahydrothiophene, and N-heterocyclic carbene;

$R^6$ and $R^7$ are either each hydrogen or together with the carbons to which they are attached represent a phenyl ring which is fused to the quinolinyl moiety represented by the structure of Formula 4 so as to form an acridinyl moiety;

$R^a$, $R^b$, $R^c$, $R^d$, $R^8$, $R^9$, and $R^{10}$ are each independently alkyl, cycloalkyl, aryl, heterocyclyl, heteroaryl, alkylcycloalkyl, alkylaryl, alkylheterocyclyl, or alkylheteroaryl;

$Y_a$ is a monoanionic ligand, such as halogen, —$OCOR^d$, —$OCOCF_3$, —$OSO_2R^d$, —$OSO_2CF_3$, —CN, —OH, —$OR^d$, and —$NR^d_2$; or a neutral solvent molecule, such as $NH_3$, $NR_3$, and $R^d_2NSO_2R^d$, wherein $R^d$ is defined above; and when $Y_a$ is neutral, the whole molecule carries a positive charge;

$X_a$ represents one, two, three, four, five, six, or seven substituents positioned at any carbon atom on the acridinyl moiety (in the case where $R^6$ and $R^7$ together with the carbons to which they are attached represent a phenyl ring which is fused to the quinolinyl moiety represented by the structure of Formula 4); or one, two, three, four, or five substituents positioned on any carbon atom on the quinolinyl moiety (in the case where $R^6$ and $R^7$ are each hydrogen), and is selected from the group consisting of hydrogen, alkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support (e.g., silica), and a polymeric moiety (e.g., polystyrene); and with the proviso that the sum of any combination of $m_1$ and p is 1, 2, 3, 4, 5, 6, 7, 8, 9, 10, 11, 12, 13, 14, 15, 16, 17, 18, 19, or 20.

The invention also relates to a process for synthesizing an amino acid or an amino acid derivative represented by the structure of Formula 1, comprising:

(a) subjecting an olefinic substrate represented by the structure of Formula 2 to a cross metathesis reaction with a cross metathesis substrate represented by the structure of formula

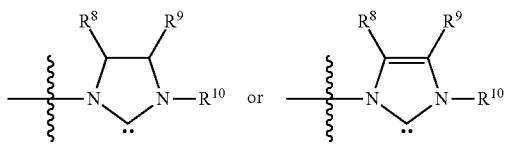

in the presence of at least one metal carbene olefin metathesis catalyst, to form an unsaturated protected alcohol intermediate represented by the structure of Formula 2a;

(b) subjecting the unsaturated protected alcohol intermediate represented by the structure of Formula 2a to hydrolysis in basic conditions to yield an unsaturated alcohol represented by the structure of Formula 3; and (c) converting the unsaturated alcohol represented by the structure of Formula 3, to an amino acid or an amino acid derivative represented by the structure of Formula 1, by subjecting the unsaturated alcohol represented by the structure of Formula 3 to a tandem amination-reduction, wherein the tandem amination-reduction is carried out in the presence of catalyst Chlorocarbonylhydrido[4,5-bis-(di-cyclohexylphosphinomethyl)acridine] Ruthenium (II); wherein:

R is —H, optionally substituted $C_1$-$C_{12}$ alkyl, optionally substituted $C_6$-$C_{10}$ aryl, optionally substituted heterocycle, or optionally substituted $C_5$-$C_{10}$ cycloalkyl;

$R^1$ is —H, —$CH_3$, or —COOR;

$R^2$ is —$OR^3$;

$R^3$ is optionally substituted —CO($C_1$-$C_{12}$ alkyl), optionally substituted —CO($C_5$-$C_{10}$ cycloalkyl), optionally substituted —CO($C_6$-$C_{10}$ aryl), or optionally substituted —CO($C_5$-$C_{10}$ heterocycle);

$R^4$ is —H or —$(CH_2)_{m1}OR^3$;

$R^5$ is —$(CH_2)_{m1}OR^3$;

a is 3, 4, 5, 6, 7, 8, 9, 10, 11, 12, 13, 14, 15, 16, 17, 18, 19, 20, 21, or 22;

m is 0, 1, 2, 3, 4, 5, 6, 7, 8, 9, 10, 11, 12, 13, 14, 15, 16, 17, 18, or 19;

$m_1$ is 1, 2, 3, 4, 5, 6, 7, 8, 9, 10, 11, 12, 13, 14, 15, 16, 17, 18, or 19;

p is 0, 1, 2, 3, 4, 5, 6, 7, 8, 9, 10, 11, 12, 13, 14, 15, 16, 17, 18, or 19; and with the proviso that the sum of any combination of $m_1$ and p is 1, 2, 3, 4, 5, 6, 7, 8, 9, 10, 11, 12, 13, 14, 15, 16, 17, 18, 19, or 20.

The invention also relates to a process for synthesizing an amino acid or an amino acid derivative represented by the structure of Formula 1, comprising:

(a) subjecting an olefinic substrate represented by the structure of Formula 2 to a cross metathesis reaction with a cross metathesis substrate represented by the structure of formula

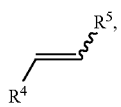

in the presence of at least one metal carbene olefin metathesis catalyst, to form an unsaturated protected alcohol intermediate represented by the structure of Formula 2a;

(b) subjecting the unsaturated protected alcohol intermediate represented by the structure of Formula 2a to hydrolysis in basic conditions to yield an unsaturated alcohol represented by the structure of Formula 3; and (c) converting the unsaturated alcohol represented by the structure of Formula 3, to an amino acid or amino acid derivative represented by the structure of Formula 1, by subjecting the unsaturated alcohol represented by the structure of Formula 3 to a tandem amination-reduction, wherein the tandem amination-reduction is carried out in the presence of catalyst Chlorocarbonylhydrido[4,5-bis-(di-i-propylphosphinomethyl)acridine] Ruthenium (II);

wherein:

R is —H, optionally substituted $C_1$-$C_{12}$ alkyl, optionally substituted $C_6$-$C_{10}$ aryl, optionally substituted heterocycle, or optionally substituted $C_5$-$C_{10}$ cycloalkyl;

$R^1$ is —H, —$CH_3$, or —COOR;

$R^2$ is —$OR^3$;

$R^3$ is optionally substituted —CO($C_1$-$C_{12}$ alkyl), optionally substituted —CO($C_5$-$C_{10}$ cycloalkyl), optionally substituted —CO($C_6$-$C_{10}$ aryl), or optionally substituted —CO($C_5$-$C_{10}$ heterocycle);

$R^4$ is —H or —$(CH_2)_{m1}OR^3$;

$R^5$ is —$(CH_2)_{m1}OR^3$;

a is 3, 4, 5, 6, 7, 8, 9, 10, 11, 12, 13, 14, 15, 16, 17, 18, 19, 20, 21, or 22;

m is 0, 1, 2, 3, 4, 5, 6, 7, 8, 9, 10, 11, 12, 13, 14, 15, 16, 17, 18, or 19;

$m_1$ is 1, 2, 3, 4, 5, 6, 7, 8, 9, 10, 11, 12, 13, 14, 15, 16, 17, 18, or 19;

p is 0, 1, 2, 3, 4, 5, 6, 7, 8, 9, 10, 11, 12, 13, 14, 15, 16, 17, 18, or 19; and with the proviso that the sum of any combination of $m_1$ and p is 1, 2, 3, 4, 5, 6, 7, 8, 9, 10, 11, 12, 13, 14, 15, 16, 17, 18, 19, or 20.

The invention also relates to a process for synthesizing an amino acid or an amino acid derivative represented by the structure of Formula 1, comprising:

(a) subjecting an olefinic substrate represented by the structure of Formula 2 to a cross metathesis reaction with a cross metathesis substrate represented by the structure of formula

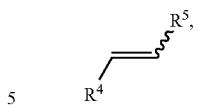

in the presence of at least one metal carbene olefin metathesis catalyst, to form an unsaturated protected alcohol intermediate represented by the structure of Formula 2a;

(b) subjecting the unsaturated protected alcohol intermediate represented by the structure of Formula 2a to hydrolysis in basic conditions to yield an unsaturated alcohol represented by the structure of Formula 3; and (c) converting the unsaturated alcohol represented by the structure of Formula 3, to an amino acid or an amino acid derivative represented by the structure of Formula 1, by subjecting the unsaturated alcohol represented by the structure of Formula 3 to a tandem amination-reduction, wherein the tandem amination-reduction is carried out in the presence of a Ruthenium pincer complex represented by the structure of Formula 4;

wherein:

R is —H, optionally substituted $C_1$-$C_6$ alkyl, optionally substituted $C_6$ aryl, or optionally substituted $C_5$-$C_{10}$ cycloalkyl;

$R^1$ is —H, —$CH_3$, or —COOR;

$R^2$ is —$OR^3$;

$R^3$ is optionally substituted —CO($C_1$-$C_6$ alkyl), optionally substituted —CO($C_5$-$C_{10}$ cycloalkyl), or optionally substituted —CO($C_6$ aryl);

$R^4$ is —H or —$(CH_2)_{m1}OR^3$;

$R^5$ is —$(CH_2)_{m1}OR^3$;

a is 6, 7, 8, 9, 10, 11, 12, 13, 14, 15, 16, or 17;

m is 0, 1, 2, 3, 4, 5, 6, or 7;

$m_1$ is 1, 2, or 3;

p is 3, 4, 5, 6, 7, 8, 9, 10, 11, or 12;

$L^4$ and $L^5$ are each independently selected from the group consisting of phosphine ($PR^aR^b$), amine ($NR^aR^b$), imine, sulfide ($SR^d$), thiol (SH), sulfoxide ($S(\!=\!O)R^d$), heteroaryl containing at least one heteroatom selected from nitrogen and sulfur; arsine ($AsR^aR^b$), stibine ($SbR^aR^b$), and an N-heterocyclic carbene represented by the structures:

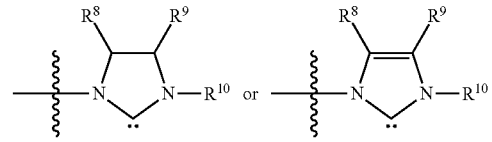

$L^6$ is a mono-dentate two-electron donor, such as CO, $PR^aR^bR^c$, $NO^+$, $AsR^aR^bR^c$, $SbR^aR^bR^c$, $SR^aR^b$, nitrile ($R^dCN$), isonitrile ($R^dNC$), $N_2$, $PF_3$, CS, heteroaryl (e.g., pyridine, thiophene), tetrahydrothiophene, and N-heterocyclic carbene;

$R^6$ and $R^7$ are either each hydrogen or together with the carbons to which they are attached represent a phenyl ring which is fused to the quinolinyl moiety represented by the structure of Formula 4 so as to form an acridinyl moiety;

$R^a$, $R^b$, $R^c$, $R^d$, $R^8$, $R^9$, and $R^{10}$ are each independently alkyl, cycloalkyl, aryl, heterocyclyl, heteroaryl, alkylcycloalkyl, alkylaryl, alkylheterocyclyl, or alkylheteroaryl;

$Y_a$ is a monoanionic ligand, such as halogen, —$OCOR^d$, —$OCOCF_3$, —$OSO_2R^d$, —$OSO_2CF_3$, —CN, —OH, —$OR^d$, and —$NR^d_2$; or a neutral solvent molecule, such as $NH_3$, $NR_3$, and $R^d{}_2NSO_2R^d$, wherein $R^d$ is defined above; and when $Y_a$ is neutral, the whole molecule carries a positive charge;

$X_a$ represents one, two, three, four, five, six, or seven substituents positioned at any carbon atom on the acridinyl moiety (in the case where $R^6$ and $R^7$ together with the carbons to which they are attached represent a phenyl ring which is fused to the quinolinyl moiety represented by the structure of Formula 4); or one, two, three, four, or five substituents positioned on any carbon atom on the quinolinyl moiety (in the case where $R^6$ and $R^7$ are each hydrogen), and is selected from the group consisting of hydrogen, alkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support (e.g., silica), and a polymeric moiety (e.g., polystyrene); and with the proviso that the sum of any combination of $m_1$ and p is 4, 5, 6, 7, 8, 9, 10, 11, 12, 13, 14, or 15.

The invention also relates to a process for synthesizing an amino acid or an amino acid derivative represented by the structure of Formula 1, comprising:

(a) subjecting an olefinic substrate represented by the structure of Formula 2 to a cross metathesis reaction with a cross metathesis substrate represented by the structure of formula

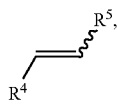

in the presence of at least one metal carbene olefin metathesis catalyst, to form an unsaturated protected alcohol intermediate represented by the structure of Formula 2a;

(b) subjecting the unsaturated protected alcohol intermediate represented by the structure of Formula 2a to hydrolysis in basic conditions to yield an unsaturated alcohol represented by the structure of Formula 3; and (c) converting the unsaturated alcohol represented by the structure of Formula 3, to an amino acid or an amino acid derivative represented by the structure of Formula 1, by subjecting the unsaturated alcohol represented by the structure of Formula 3 to a tandem amination-reduction, wherein the tandem amination-reduction is carried out in the presence of a Ruthenium pincer complex represented by the structure of Formula 4;

wherein:
R is —H or optionally substituted $C_1$-$C_3$ alkyl;
$R^1$ is —H, —$CH_3$, or —COOR;
$R^2$ is —$OR^3$;
$R^3$ is optionally substituted —CO($C_1$-$C_3$ alkyl);
$R^4$ is —H or —$(CH_2)_{m1}OR^3$;
$R^5$ is —$(CH_2)_{m1}OR^3$;
a is 9, 10, 11, or 12;
m is 0, 1, 2, 3, 4, 5, 6, or 7;
$m_1$ is 1 or 2;
p is 6, 7, or 8;
$L^4$ and $L^5$ are each independently selected from the group consisting of phosphine ($PR^aR^b$), amine ($NR^aR^b$), imine, sulfide ($SR^d$), thiol (SH), sulfoxide ($S(=O)R^d$), heteroaryl containing at least one heteroatom selected from nitrogen and sulfur; arsine ($AsR^aR^b$), stibine ($SbR^aR^b$), and an N-heterocyclic carbene represented by the structures:

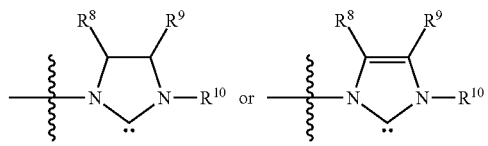

$L^6$ is a mono-dentate two-electron donor, such as CO, $PR^aR^bR^c$, $NO^+$, $AsR^aR^bR^c$, $SbR^aR^bR^c$, $SR^aR^b$, nitrile ($R^dCN$), isonitrile ($R^dNC$), $N_2$, $PF_3$, CS, heteroaryl (e.g., pyridine, thiophene), tetrahydrothiophene, and N-heterocyclic carbene;

$R^6$ and $R^7$ are either each hydrogen or together with the carbons to which they are attached represent a phenyl ring which is fused to the quinolinyl moiety represented by the structure of Formula 4 so as to form an acridinyl moiety;

$R^a$, $R^b$, $R^c$, $R^d$, $R^8$, $R^9$, and $R^{10}$ are each independently alkyl, cycloalkyl, aryl, heterocyclyl, heteroaryl, alkylcycloalkyl, alkylaryl, alkylheterocyclyl, or alkylheteroaryl;

$Y_a$ is a monoanionic ligand, such as halogen, —$OCOR^d$, —$OCOCF_3$, —$OSO_2R^d$, —$OSO_2CF_3$, —CN, —OH, —$OR^d$, and —$NR^d{}_2$; or a neutral solvent molecule, such as $NH_3$, $NR_3$, and $R^d{}_2NSO_2R^d$, wherein $R^d$ is defined above; and when $Y_a$ is neutral, the whole molecule carries a positive charge; and $X_a$ represents one, two, three, four, five, six, or seven substituents positioned at any carbon atom on the acridinyl moiety (in the case where $R^6$ and $R^7$ together with the carbons to which they are attached represent a phenyl ring which is fused to the quinolinyl moiety represented by the structure of Formula 4); or one, two, three, four, or five substituents positioned on any carbon atom on the quinolinyl moiety (in the case where $R^6$ and $R^7$ are each hydrogen), and is selected from the group consisting of hydrogen, alkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support (e.g., silica), and a polymeric moiety (e.g., polystyrene).

The invention relates to a process for synthesizing an amino acid or an amino acid derivative represented by the structure of Formula 1, comprising:

(a) subjecting an olefinic substrate represented by the structure of Formula 2 to a cross metathesis reaction with a cross metathesis substrate represented by the structure of formula

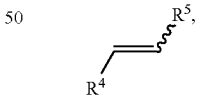

in the presence of at least one metal carbene olefin metathesis catalyst, to form an unsaturated protected alcohol intermediate represented by the structure of Formula 2a;

(b) subjecting the unsaturated protected alcohol intermediate represented by the structure of Formula 2a to hydrolysis in basic conditions to yield an unsaturated alcohol represented by the structure of Formula 3; and (c) converting the unsaturated alcohol represented by the structure of Formula 3, to an amino acid or an amino acid derivative represented by the structure of Formula 1, by subjecting the unsaturated alcohol represented by the structure of Formula 3 to a tandem amination-reduction, wherein the tandem amination-reduction is carried out in the presence catalyst Chlorocarbonylhydrido[4,5-bis-(di-cyclohexylphosphinomethyl)acridine] Ruthenium (II); wherein:
R is —H or optionally substituted $C_1$-$C_3$ alkyl;
$R^1$ is —H, —$CH_3$, or —COOR;
$R^2$ is —$OR^3$;
$R^3$ is optionally substituted —CO($C_1$-$C_3$ alkyl);
$R^4$ is —H or —$(CH_2)_{m1}OR^3$;
$R^5$ is —$(CH_2)_{m1}OR^3$;
a is 9, 10, 11, or 12;
m is 0, 1, 2, 3, 4, 5, 6, or 7;
$m_1$ is 1 or 2; and
p is 6, 7, or 8.

The invention relates to a process for synthesizing an amino acid or an amino acid derivative represented by the structure of Formula 1, comprising:

(a) subjecting an olefinic substrate represented by the structure of Formula 2 to a cross metathesis reaction with a cross metathesis substrate represented by the structure of formula

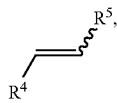

in the presence of at least one metal carbene olefin metathesis catalyst, to form an unsaturated protected alcohol intermediate represented by the structure of Formula 2a;

(b) subjecting the unsaturated protected alcohol intermediate represented by the structure of Formula 2a to hydrolysis in basic conditions to yield an unsaturated alcohol represented by the structure of Formula 3; and (c) converting the unsaturated alcohol represented by the structure of Formula 3, to an amino acid or an amino acid derivative represented by the structure of Formula 1, by subjecting the unsaturated alcohol represented by the structure of Formula 3 to a tandem amination-reduction, wherein the tandem amination-reduction is carried out in the presence of catalyst Chlorocarbonylhydrido[4,5-bis-(di-i-propylphosphinomethyl)acridine] Ruthenium (II); wherein:
R is —H or optionally substituted $C_1$-$C_3$ alkyl;
$R^1$ is —H, —$CH_3$, or —COOR;
$R^2$ is —$OR^3$;
$R^3$ is optionally substituted —CO($C_1$-$C_3$ alkyl);
$R^4$ is —H or —$(CH_2)_{m1}OR^3$;
$R^5$ is —$(CH_2)_{m1}OR^3$;
a is 9, 10, 11, or 12;
m is 0, 1, 2, 3, 4, 5, 6, or 7;
$m_1$ is 1 or 2; and
p is 6, 7, or 8.

In another aspect the invention relates to a process for synthesizing an amino acid represented by the structure of Formula 1, comprising:

(a) subjecting an olefinic substrate represented by the structure of Formula 2 to a cross metathesis reaction, in the presence of at least one metal carbene olefin metathesis catalyst, with 1,4-diacetoxy-2-butene to form an unsaturated intermediate represented by the structure of Formula 2a;

(b) subjecting the unsaturated intermediate represented by the structure of Formula 2a to hydrolysis in basic conditions to yield an unsaturated alcohol represented by the structure of Formula 3; and (c) converting the unsaturated alcohol represented by the structure of Formula 3 to an amino acid derivative represented by the structure of Formula 1 by subjecting the unsaturated alcohol represented by the structure of Formula 3 to a tandem amination-reduction, wherein the tandem amination-reduction is carried out in the presence of a Ruthenium pincer complex represented by the structure of Formula 4;

wherein:
R is —H;
$R^1$ is —H, —$CH_3$, or —COOR;
$R^2$ is —$OR^3$;
$R^3$ is $CH_3(CO)$—;
a is 9, 10, 11, or 12;
m is 0, 1, 2, 3, 4, 5, 6, or 7;
$m_1$ is 1 or 2;
p is 6, 7, or 8;
$L^4$ and $L^5$ are each independently selected from the group consisting of phosphine ($PR^aR^b$), amine ($NR^aR^b$), imine, sulfide ($SR^d$), thiol (SH), sulfoxide (S(=O)$R^d$), heteroaryl containing at least one heteroatom selected from nitrogen and sulfur; arsine ($AsR^aR^b$), stibine ($SbR^aR^b$), and an N-heterocyclic carbene represented by the structures:

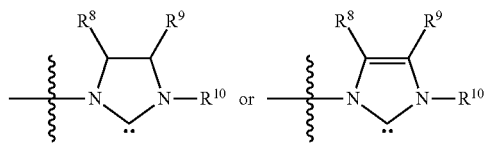

$L^6$ is a mono-dentate two-electron donor, such as CO, $PR^aR^bR^c$, $NO^+$, $AsR^aR^bR^c$, $SbR^aR^bR^c$, $SR^aR^b$, nitrile ($R^dCN$), isonitrile ($R^dNC$), $N_2$, $PF_3$, CS, heteroaryl (e.g., pyridine, thiophene), tetrahydrothiophene, and N-heterocyclic carbene;

$R^6$ and $R^7$ are either each hydrogen or together with the carbons to which they are attached represent a phenyl ring which is fused to the quinolinyl moiety represented by the structure of Formula 4 so as to form an acridinyl moiety;

$R^a$, $R^b$, $R^c$, $R^d$, $R^8$, $R^9$, and $R^{10}$ are each independently alkyl, cycloalkyl, aryl, heterocyclyl, heteroaryl, alkylcycloalkyl, alkylaryl, alkylheterocyclyl, or alkylheteroaryl;

$Y_a$ is a monoanionic ligand, such as halogen, —$OCOR^d$, —$OCOCF_3$, —$OSO_2R^d$, —$OSO_2CF_3$, —CN, —OH, —$OR^d$, and —$NR^d{}_2$; or a neutral solvent molecule, such as $NH_3$, $NR_3$, and $R^d{}_2NSO_2R^d$, wherein $R^d$ is defined above; and when $Y_a$ is neutral, the whole molecule carries a positive charge; and $X_a$ represents one, two, three, four, five, six, or seven substituents positioned at any carbon atom on the acridinyl moiety (in the case where $R^6$ and $R^7$ together with the carbons to which they are attached represent a phenyl ring which is fused to the quinolinyl moiety represented by the structure of Formula 4); or one, two, three, four, or five substituents positioned on any carbon atom on the quinolinyl moiety (in the case where $R^6$ and $R^7$ are each hydrogen), and is selected from the group consisting of hydrogen, alkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support (e.g., silica), and a polymeric moiety (e.g., polystyrene).

In another aspect the invention relates to a process for synthesizing an amino acid derivative represented by the structure of Formula 1, comprising:

(a) subjecting an olefinic substrate represented by the structure of Formula 2 to a cross metathesis reaction, wherein the cross metathesis reaction is carried out in the presence of at least one metal carbene olefin metathesis catalyst, with 1,4-diacetoxy-2-butene to form an unsaturated intermediate represented by the structure of Formula 2a;

(b) subjecting the unsaturated intermediate represented by the structure of Formula 2a to hydrolysis in basic conditions to yield an unsaturated alcohol represented by the structure of Formula 3; and (c) converting the unsaturated alcohol represented by the structure of Formula 3 to an amino acid derivative represented by the structure of Formula 1 by subjecting the unsaturated alcohol represented by the structure of Formula 3 to a tandem amination-reduction, wherein the tandem amination-reduction is carried out in the presence of a Ruthenium pincer complex represented by the structure of Formula 4;

wherein:
R is —$CH_3$;
$R^1$ is —H, —$CH_3$, or —COOR;
$R^2$ is —$OR^3$;
$R^3$ is $CH_3(CO)$—;
a is 9, 10, 11, or 12;
m is 0, 1, 2, 3, 4, 5, 6, or 7;
$m_1$ is 1 or 2;
p is 6, 7, or 8;
$L^4$ and $L^5$ are each independently selected from the group consisting of phosphine ($PR^aR^b$), amine ($NR^aR^b$), imine, sulfide ($SR^d$), thiol (SH), sulfoxide ($S(=O)R^d$), heteroaryl containing at least one heteroatom selected from nitrogen and sulfur; arsine ($AsR^aR^b$), stibine ($SbR^aR^b$), and an N-heterocyclic carbene represented by the structures:

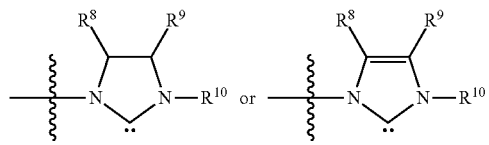

$L^6$ is a mono-dentate two-electron donor, such as CO, $PR^aR^bR^c$, $NO^+$, $AsR^aR^bR^c$, $SbR^aR^bR^c$, $SR^aR^b$, nitrile ($R^dCN$), isonitrile ($R^dNC$), $N_2$, $PF_3$, CS, heteroaryl (e.g., pyridine, thiophene), tetrahydrothiophene, and N-heterocyclic carbene;

$R^6$ and $R^7$ are either each hydrogen or together with the carbons to which they are attached represent a phenyl ring which is fused to the quinolinyl moiety represented by the structure of Formula 4 so as to form an acridinyl moiety;

$R^a$, $R^b$, $R^c$, $R^d$, $R^8$, $R^9$, and $R^{10}$ are each independently alkyl, cycloalkyl, aryl, heterocyclyl, heteroaryl, alkylcycloalkyl, alkylaryl, alkylheterocyclyl, or alkylheteroaryl;

$Y_a$ is a monoanionic ligand, such as halogen, —$OCOR^d$, —$OCOCF_3$, —$OSO_2R^d$, —$OSO_2CF_3$, —CN, —OH, —$OR^d$, and —$NR^d{}_2$; or a neutral solvent molecule, such as $NH_3$, $NR_3$, and $R^d{}_2NSO_2R^d$, wherein $R^d$ is defined above; and when $Y_a$ is neutral, the whole molecule carries a positive charge; and $X_a$ represents one, two, three, four, five, six, or seven substituents positioned at any carbon atom on the acridinyl moiety (in the case where $R^6$ and $R^7$ together with the carbons to which they are attached represent a phenyl ring which is fused to the quinolinyl moiety represented by the structure of Formula 4; or one, two, three, four, or five substituents positioned on any carbon atom on the quinolinyl moiety (in the case where $R^6$ and $R^7$ are each hydrogen), and is selected from the group consisting of hydrogen, alkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support (e.g., silica), and a polymeric moiety (e.g., polystyrene).

In another aspect the invention relates to a process for synthesizing an amino acid represented by the structure of Formula 1, comprising:

(a) subjecting an olefinic substrate represented by the structure of Formula 2 to a cross metathesis reaction, in the presence of at least one metal carbene olefin metathesis catalyst with 1,4-diacetoxy-2-butene to form an unsaturated intermediate represented by the structure of Formula 2a;

(b) subjecting the unsaturated intermediate represented by the structure of Formula 2a to hydrolysis in basic conditions to yield an unsaturated alcohol represented by the structure of Formula 3; and (c) converting the unsaturated alcohol represented by the structure of Formula 3 to an amino acid derivative represented by the structure of Formula 1 by subjecting the unsaturated alcohol represented by the structure of Formula 3 to a tandem amination-reduction, wherein the tandem amination-reduction is carried out in the presence of catalyst [RuHCl(A-iPr-PNP)(CO)]; wherein:

R is —H;
$R^1$ is —H, —$CH_3$, or —COOR;
$R^2$ is —$OR^3$;
$R^3$ is $CH_3(CO)$—;
a is 9, 10, 11, or 12;
m is 0, 1, 2, 3, 4, 5, 6, or 7;
$m_1$ is 1 or 2; and
p is 6, 7, or 8.

In another aspect the invention relates to a process for synthesizing an amino acid represented by the structure of Formula 1, comprising:

(a) subjecting an olefinic substrate represented by the structure of Formula 2 to a cross metathesis reaction, in the presence of at least one metal carbene olefin metathesis catalyst with 1,4-diacetoxy-2-butene to form an unsaturated intermediate represented by the structure of Formula 2a;

(b) subjecting the unsaturated intermediate represented by the structure of Formula 2a to hydrolysis in basic conditions to yield an unsaturated alcohol represented by the structure of Formula 3; and (c) converting the unsaturated alcohol represented by the structure of Formula 3 to an amino acid derivative represented by the structure of Formula 1 by subjecting the unsaturated alcohol represented by the structure of Formula 3 to a tandem amination-reduction, wherein the tandem amination-reduction is carried out in the presence of catalyst [RuHCl(A-Cy-PNP)(CO)];

wherein:
R is —H;
$R^1$ is —H, —$CH_3$, or —COOR;
$R^2$ is —$OR^3$;
$R^3$ is $CH_3(CO)$—;
a is 9, 10, 11, or 12;
m is 0, 1, 2, 3, 4, 5, 6, or 7;
$m_1$ is 1 or 2; and
p is 6, 7, or 8.

In another aspect the invention relates to a process for synthesizing an amino acid derivative represented by the structure of Formula 1, comprising:

(a) subjecting an olefinic substrate represented by the structure of Formula 2 to a cross metathesis reaction, in the presence of at least one metal carbene olefin metathesis catalyst with 1,4-diacetoxy-2-butene to form an unsaturated intermediate represented by the structure of Formula 2a;

(b) subjecting the unsaturated intermediate represented by the structure of Formula 2a to hydrolysis in basic conditions to yield an unsaturated alcohol represented by the structure of Formula 3; and (c) converting the unsaturated alcohol represented by the structure of Formula 3 to an amino acid derivative represented by the structure of Formula 1 by subjecting the unsaturated alcohol represented by the structure of Formula 3 to a tandem amination-reduction, wherein the tandem amination-reduction is carried out in the presence of catalyst [RuHCl(A-Cy-PNP)(CO)];

wherein:
R is —$CH_3$;
$R^1$ is —H, —$CH_3$, or —COOR;
$R^2$ is —$OR^3$;
$R^3$ is $CH_3(CO)$—;
a is 9, 10, 11, or 12;
m is 0, 1, 2, 3, 4, 5, 6, or 7;
$m_1$ is 1 or 2; and
p is 6, 7, or 8.

In another aspect the invention relates to a process for synthesizing an amino acid derivative represented by the structure of Formula 1, comprising:

(a) subjecting an olefinic substrate represented by the structure of Formula 2 to a cross metathesis reaction, in the presence of at least one metal carbene olefin metathesis catalyst with 1,4-diacetoxy-2-butene to form an unsaturated intermediate represented by the structure of Formula 2a;

(b) subjecting the unsaturated intermediate represented by the structure of Formula 2a to hydrolysis in basic conditions to yield an unsaturated alcohol represented by the structure of Formula 3; and (c) converting the unsaturated alcohol represented by the structure of Formula 3 to an amino acid derivative represented by the structure of Formula 1 by subjecting the unsaturated alcohol represented by the structure of Formula 3 to a tandem amination-reduction, wherein the tandem amination-reduction is carried out in the presence of catalyst [RuHCl(A-iPr-PNP)(CO)];

wherein:
R is —$CH_3$;
$R^1$ is —H, —$CH_3$, or —COOR;
$R^2$ is —$OR^3$;
$R^3$ is $CH_3(CO)$—;
a is 9, 10, 11, or 12;
m is 0, 1, 2, 3, 4, 5, 6, or 7;
$m_1$ is 1 or 2; and
p is 6, 7, or 8.

In another aspect the invention relates to a process for synthesizing an amino acid derivative represented by the structure of Formula 1, comprising:

(a) subjecting an olefinic substrate represented by the structure of Formula 2 to a cross metathesis reaction, in the presence of at least one metal carbene olefin metathesis catalyst with 1,4-diacetoxy-2-butene to form an unsaturated intermediate represented by the structure of Formula 2a;

(b) subjecting the unsaturated intermediate represented by the structure of Formula 2a to hydrolysis in basic conditions to yield an unsaturated alcohol represented by the structure of Formula 3; and (c) converting the unsaturated alcohol represented by the structure of Formula 3 to an amino acid derivative represented by the structure of Formula 1 by subjecting the unsaturated alcohol represented by the structure of Formula 3 to a tandem amination-reduction, wherein the tandem amination-reduction is carried out in the presence of catalyst [RuHCl(A-iPr-PNP)(CO)];

wherein:
R is —$CH_3$;
$R^1$ is —H;
$R^2$ is —$OR^3$;
$R^3$ is $CH_3(CO)$—;
a is 10;
m is 0;
$m_1$ is 1; and
p is 7.

In another aspect the invention relates to a process for synthesizing an amino acid derivative represented by the structure of Formula 1, comprising:

(a) subjecting an olefinic substrate represented by the structure of Formula 2 to a cross metathesis reaction, in the presence of at least one metal carbene olefin metathesis catalyst with 1,4-diacetoxy-2-butene to form an unsaturated intermediate represented by the structure of Formula 2a;

(b) subjecting the unsaturated intermediate represented by the structure of Formula 2a to hydrolysis in basic conditions to yield an unsaturated alcohol represented by the structure of Formula 3; and (c) converting the unsaturated alcohol represented by the structure of Formula 3 to an amino acid derivative represented by the structure of Formula 1 by subjecting the unsaturated alcohol represented by the structure of Formula 3 to a tandem amination-reduction, wherein the tandem amination-reduction is carried out in the presence of catalyst [RuHCl(A-iPr-PNP)(CO)];

wherein:
R is —$CH_3$;
$R^1$ is —H;
$R^2$ is —$OR^3$;
$R^3$ is $CH_3(CO)$—;
a is 11;
m is 0;
$m_1$ is 1; and
p is 8.

In another aspect the invention relates to a process for synthesizing an amino acid derivative represented by the structure of Formula 1, comprising:

(a) subjecting an olefinic substrate represented by the structure of Formula 2 to a cross metathesis reaction, in the presence of at least one metal carbene olefin metathesis catalyst with 1,4-diacetoxy-2-butene to form an unsaturated intermediate represented by the structure of Formula 2a;

(b) subjecting the unsaturated intermediate represented by the structure of Formula 2a to hydrolysis in basic conditions to yield an unsaturated alcohol represented by the structure of Formula 3; and (c) converting the unsaturated alcohol represented by the structure of Formula 3 to an amino acid derivative represented by the structure of Formula 1 by subjecting the unsaturated alcohol represented by the structure of Formula 3 to a tandem amination-reduction, wherein the tandem amination-reduction is carried out in the presence of catalyst [RuHCl(A-Cy-PNP)(CO)];

wherein:
R is —$CH_3$;
$R^1$ is —H;
$R^2$ is —$OR^3$;
$R^3$ is $CH_3(CO)$—;
a is 10;
m is 0;
$m_1$ is 1; and
p is 7.

In another aspect the invention relates to a process for synthesizing an amino acid derivative represented by the structure of Formula 1, comprising:
(a) subjecting an olefinic substrate represented by the structure of Formula 2 to a cross metathesis reaction, in the presence of at least one metal carbene olefin metathesis catalyst with 1,4-diacetoxy-2-butene to form an unsaturated intermediate represented by the structure of Formula 2a;
(b) subjecting the unsaturated intermediate represented by the structure of Formula 2a to hydrolysis in basic conditions to yield an unsaturated alcohol represented by the structure of Formula 3; and
(c) converting the unsaturated alcohol represented by the structure of Formula 3 to an amino acid derivative represented by the structure of Formula 1 by subjecting the unsaturated alcohol represented by the structure of Formula 3 to a tandem amination-reduction, wherein the tandem amination-reduction is carried out in the presence of catalyst [RuHCl(A-Cy-PNP)(CO)];
wherein:
R is —$CH_3$;
$R^1$ is —H;
$R^2$ is —$OR^3$;
$R^3$ is $CH_3(CO)$—;
a is 11;
m is 0;
$m_1$ is 1; and
p is 8.

In another aspect the invention relates to a process for synthesizing an amino acid derivative of Formula 1, comprising:
(a) subjecting an olefinic substrate represented by the structure of Formula 2 to a cross metathesis reaction, in the presence of at least one metal carbene olefin metathesis catalyst with 1,4-diacetoxy-2-butene to form an unsaturated intermediate represented by the structure of Formula 2a;
(b) subjecting the unsaturated intermediate represented by the structure of Formula 2a to hydrolysis in basic conditions to yield an unsaturated alcohol represented by the structure of Formula 3; and
(c) converting the unsaturated alcohol represented by the structure of Formula 3 to an amino acid derivative represented by the structure of Formula 1 by subjecting the unsaturated alcohol represented by the structure of Formula 3 to a tandem amination-reduction, wherein the tandem amination-reduction is carried out in the presence of catalyst [RuHCl(A-iPr-PNP)(CO)];
wherein:
R is —$CH_3$;
$R^1$ is —H;
$R^2$ is —$OR^3$;
$R^3$ is $CH_3(CO)$—;
a is 10;
m is 2;
$m_1$ is 1; and
p is 7.

In another aspect the invention relates to a process for synthesizing an amino acid derivative represented by the structure of Formula 1, comprising:
(a) subjecting an olefinic substrate of Formula 2 to a cross metathesis reaction, in the presence of at least one metal carbene olefin metathesis catalyst with 1,4-diacetoxy-2-butene to form an unsaturated intermediate represented by the structure of Formula 2a;
(b) subjecting the unsaturated intermediate of Formula 2a to hydrolysis in basic conditions to yield an unsaturated alcohol represented by the structure of Formula 3; and
(c) converting the unsaturated alcohol represented by the structure of Formula 3 to an amino acid derivative represented by the structure of Formula 1 by subjecting the unsaturated alcohol represented by the structure of Formula 3 to a tandem amination-reduction, wherein the tandem amination-reduction is carried out in the presence of catalyst [RuHCl(A-Cy-PNP)(CO)];
wherein:
R is —$CH_3$;
$R^1$ is —H;
$R^2$ is —$OR^3$;
$R^3$ is $CH_3(CO)$—;
a is 10;
m is 2;
$m_1$ is 1; and
p is 7.

In one aspect, the invention relates to a one pot process for synthesizing methyl 11-cyanoundec-10-enoate comprising the steps of:
(a) subjecting methyl 12-hydroxy-10-dodecenoate to isopropanol and in the presence of a copper catalyst to form methyl 12-oxo-10-dodecenoate; and
(b) subjecting methyl 12-oxo-10-dodecenoate to ammonia and hydrogen peroxide in the presence of CuCl to form methyl 11-cyanoundec-10-enoate.

In another aspect, the invention relates to one pot process for synthesizing methyl 11-cyanoundec-10-enoate comprising the steps of:
(a) subjecting methyl 12-hydroxy-10-dodecenoate to isopropanol in the presence of [(TMEDA)Cu(µ-OH)]$_2$Cl$_2$ to form methyl 12-oxo-10-dodecenoate; and
(b) subjecting methyl 12-oxo-10-dodecenoate to ammonia and hydrogen peroxide in the presence of CuCl to form methyl 11-cyanoundec-10-enoate.

In another aspect, the invention relates to a process for synthesizing methyl 12-amino-dodecanoate comprising the steps of:
(a) subjecting methyl-10-undecenoate and cis-1,4-dichloro-2-butene to a cross metathesis reaction, to afford methyl 12-chloro-10-dodecenoate;
(b) subjecting methyl 12-chloro-10-dodecenoate to ammonia to afford methyl 12-amino-10-dodecenoate; and
(c) subjecting methyl 12-amino-10-dodecenoate to Ni Raney and hydrogen to afford methyl 12-amino-dodecanoate.

In another aspect, the invention relates to a process for synthesizing methyl 12-amino-dodecanoate comprising the steps of:
(a) subjecting methyl-10-undecenoate and cis-1,4-dichloro-2-butene to cross metathesis in the presence of a metal carbene olefin metathesis catalyst to afford methyl 12-chloro-10-dodecenoate;
(b) subjecting methyl 12-chloro-10-dodecenoate to ammonia to afford methyl 12-amino-10-dodecenoate; and
(c) subjecting methyl 12-amino-10-dodecenoate to Ni Raney and hydrogen to afford methyl 12-amino-dodecanoate.

In another aspect, the invention relates to a process for synthesizing methyl 12-amino-dodecanoate comprising the steps of:
(a) subjecting methyl-10-undecenoate and cis-1,4-dichloro-2-butene to a cross metathesis reaction in the presence of a catalyst represented by the structure of Formula (I), to afford methyl 12-chloro-10-dodecenoate;
(b) subjecting methyl 12-chloro-10-dodecenoate to ammonia to afford methyl 12-amino-10-dodecenoate; and (c) subjecting methyl 12-amino-10-dodecenoate to Ni Raney and hydrogen to afford methyl 12-amino-dodecanoate.

The invention provides a method of making amino acids and amino acid derivatives. Amino acids and amino acid derivatives made by the methods described herein may be used as precursors for making polyamides, such as, for example, PA11 and/or PA12. Further, the invention describes a method of making amino acids and amino acid derivatives by cross metathesis of at least one cross metathesis substrate with at least one olefinic substrate in the presence of at least one metal carbene olefin metathesis catalyst, where the at least one cross metathesis substrate is selected from an alkyl 9-decenoate or an alkyl 10-undecenoate. The invention also describes a method of making amino acids and amino acid derivatives by cross metathesis of at least one cross metathesis substrate with at least one olefinic substrate in the presence of at least one metal carbene olefin metathesis catalyst, where the at least one cross metathesis substrate is 1,4-diacetoxy-2-butene.

In another aspect, the invention describes a method of making amino acids and amino acid derivatives by cross metathesis of at least one cross metathesis substrate with at least one olefinic substrate in the presence of at least one metal carbene olefin metathesis catalyst, where the at least one cross metathesis substrate is 1,4-dihydroxy-2-butene, wherein the hydroxyl groups are protected by various acceptable protecting groups, including, but not limited to, formyl, propionyl, butyryl, benzyl, benzoyl, ethyl vinyl ethers, methyl, ethyl, acetyl, acyl, ethylene glycol and methyl ethers of ethylene glycol, sulfate, benzylsulfonate, phosphinates, methoxymethyl ether (MOM), methylthiomethyl ether (MTM), 2-methoxyethoxymethyl ether (MEM), bis-2-chloroethoxy)methyl ether, tetrahydropyranyl ether (THP), tetrahydrothiopyranyl ether, 4-methoxytetrahydropyranyl ether, 4-methoxythiotetrahydropyranyl ether, tetrahydrofuranyl ether, tetrahydrothiofuranyl ether, 1-ethoxyethyl ether, 1-methyl-1-methoxyethyl ether, 2-(phenylselenyl)ethyl ether, ethyl vinyl ether (EVE), tert-butyl ether (tBu), allyl ether, benzyl ether (Bn), ortho-benzyl ether, triphenylmethyl ether, alpha-naphthyldiphenylmethyl ether, para-methoxyphenyldiphenylmethyl ether, 9-(9-phenyl-10-oxo)anthryl ether, trimethylsilyl (TMS), isopropyldimethylsilyl ether, tert-butyldimethylsilyl ether (TBDMS), t-butyldiphenylsilyl ether (TBDPS), tribenzylsilyl ether, triisopropylsilyl ether, formate ester, acetate ester, trichloroacetate ester, phenoxyacetate ester, isobutyrate ester, propionate ester, butyrate ester, pivaloate ester, benzoate ester, adamantoate ester, methyl carbonate, 2,2,2-trichloromethyl carbonate, allyl carbonate, para-nitrophenyl carbonate, benzyl carbonate, para-nitrobenzyl carbonate, or S-benzyl thiocarbonate.

In another aspect, the invention is directed to a process for synthesizing methyl 11-aminoundecanoate comprising the steps of (a) subjecting methyl 9-decenoate and/or methyl 9-dodecenoate to a cross metathesis reaction with 1,4-diacetoxy-2-butene in the presence of [1,3-bis(2,6-di-isopropylphenyl)-2-imidazolidinylidene] dichloro(o-isopropoxyphenylmethylene) Ruthenium(II) to form methyl 11-acetoxy-9-undecenoate

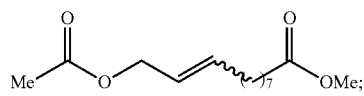

(b) subjecting methyl 11-acetoxy-9-undecenoate to hydrolysis in basic conditions to form methyl 11-hydroxy-undecenoate

and;

(c) subjecting methyl 11-hydroxy-undecenoate to a tandem amination-reduction reaction in the presence of catalyst Chlorocarbonylhydrido[4,5-bis-(di-i-propylphosphinomethyl)acridine] Ruthenium (II) or Chlorocarbonylhydrido[4,5-bis-(di-cyclohexylphosphinomethyl)acridine] Ruthenium (II).

In another aspect, the invention is directed to a process of synthesizing methyl 12-aminododecanoate comprising the steps of (a) subjecting methyl 10-undecenoate to a cross metathesis reaction with 1,4-diacetoxy-2-butene in the presence of [1,3-bis(2,6-di-isopropylphenyl)-2-imidazolidinylidene] dichloro(o-isopropoxyphenylmethylene)Ruthenium(II) to form methyl 12-acetoxy-10-dodecenoate

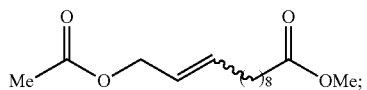

(b) subjecting methyl 12-acetoxy-10-dodecenoate to basic hydrolysis to form methyl 12-hydroxy-10-dodecenoate

and;

(c) subjecting the methyl 12-hydroxy-10-dodecenoate to a tandem amination-reduction reaction in the presence of catalyst Chlorocarbonylhydrido[4,5-bis-(di-i-propylphosphinomethyl)acridine] Ruthenium (II) or Chlorocarbonylhydrido[4,5-bis-(di-cyclohexylphosphinomethyl)acridine] Ruthenium (II).

In another embodiment, the invention is directed to a process for synthesizing methyl 11-aminoundecanoate, comprising: a step of reacting methyl 9-decenoate and/or methyl 9-dodecenoate with 1,4-diacetoxy-2-butene in the presence of at least one metal carbene olefin metathesis catalyst; a step of converting methyl 11-acetoxy-9-undecenoate, obtained in the first step, to methyl 11-hydroxy-9-undecenoate, and a step of converting methyl 11-hydroxy-9-undecenoate to methyl 11-aminoundecanoate, in the presence of a catalyst based on a Ruthenium pincer complex represented by the structure of Formula 4.

In another embodiment, the invention is directed to a process for synthesizing methyl 12-aminoundecanoate, comprising: a step of reacting methyl 10-undecenoate with 1,4-diacetoxy-2-butene in the presence of at least one metal carbene olefin metathesis catalyst; a step of converting methyl 12-acetoxy-10-dodecenoate, obtained in the first step, to methyl 12-hydroxy-10-dodecenoate, and a step of converting methyl 12-hydroxy-10-dodecenoate to methyl 12-aminododecanoate, in the presence of a catalyst based on a Ruthenium pincer complex represented by the structure of Formula 4.

In a further embodiment, the invention relates to a method of synthesizing amino acids or amino acid derivatives (e.g., amino esters) of the formula $NH_2$—$(CH_2)_a$—COOR, in which a is an integer between 3 and 22, and R is H, optionally substituted $C_1$-$C_{12}$ alkyl, optionally substituted $C_6$-$C_{10}$ aryl, optionally substituted heterocycle or optionally substituted $C_5$-$C_{10}$ cycloalkyl; the method to synthesize amino acids or amino acid derivatives (e.g., amino esters), involving a catalytic cross metathesis reaction of a mono-unsaturated fatty acid or fatty ester of the formula $R^1$—$(CH_2)_m$—CH=CH—$(CH_2)_p$—COOR, in which $R^1$ is —H, —$CH_3$, or a —COOR group, m is an integer selected from 0-19, and p is an integer selected from 0-19; with a compound of the formula $R^4$—CH=CH—$R^5$ in which $R^4$ is —H or —$(CH_2)_{m1}OR^3$; $R^5$ is —$(CH_2)_{m1}OR^3$; $m_1$ is an integer selected from 1-19; $R^2$ is —$OR^3$, where $R^3$ is optionally substituted —CO($C_1$-$C_{12}$ alkyl), optionally substituted —CO($C_5$-$C_{10}$ cycloalkyl), optionally substituted —CO($C_6$-$C_{10}$ aryl), or optionally substituted —CO($C_5$-$C_{10}$ heterocycle); to yield a product of formula $R^2$—$(CH_2)_{m1}$—CH=CH—$(CH_2)_p$—COOR; wherein $R^2$ is —$OR^3$, where $R^3$ is removed by hydrolysis to produce a product of formula HO—$(CH_2)_{m1}$—CH=CH—$(CH_2)_p$—COOR which is converted directly by any sequence of hydrogenation and amination steps to yield $NH_2$—$(CH_2)_a$—COOR or by any sequence of oxidization in the presence of ammonia to a nitrile and hydrogenation to yield $NH_2$—$(CH_2)_a$—COOR, as depicted in Scheme 1.

Scheme 1

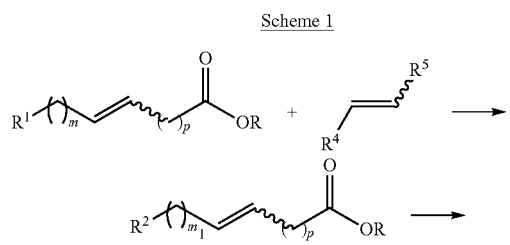

In another aspect the invention relates to the synthesis of amino acid derivatives, as shown in Scheme 2.

Scheme 2

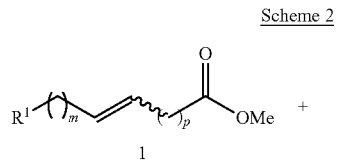

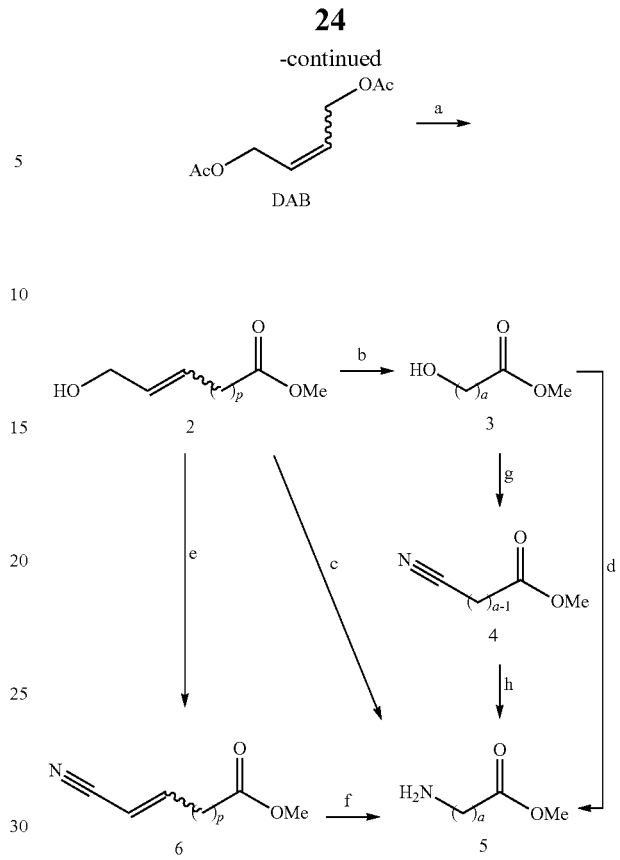

Cross-metathesis of 1 with 1,4-diacetoxy-2-butene (DAB), followed by deprotection, (Step a), yields the allylic alcohol ester 2 which can be hydrogenated (Step b) to hydroxy ester 3, which after amination (Step d) affords the desired amino acid derivative 5. Alternatively, allylic alcohol ester 2 can undergo tandem amination-reduction (Step c) directly affording amino acid derivative 5. Allylic alcohol ester 2 can also be oxidized (Step e) to the corresponding nitrile 6, which after reduction (Step f) gives the desired amino acid derivative 5. In a different setting, hydroxy ester 3 can be oxidized (Step g) to the corresponding nitrile 4, which after reduction (Step h) gives the desired amino acid derivative 5.

In another aspect the invention relates particularly to the synthesis of amino acid derivative 11, as shown in Scheme 3.

Scheme 3

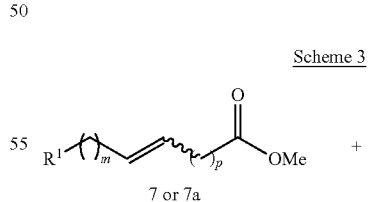

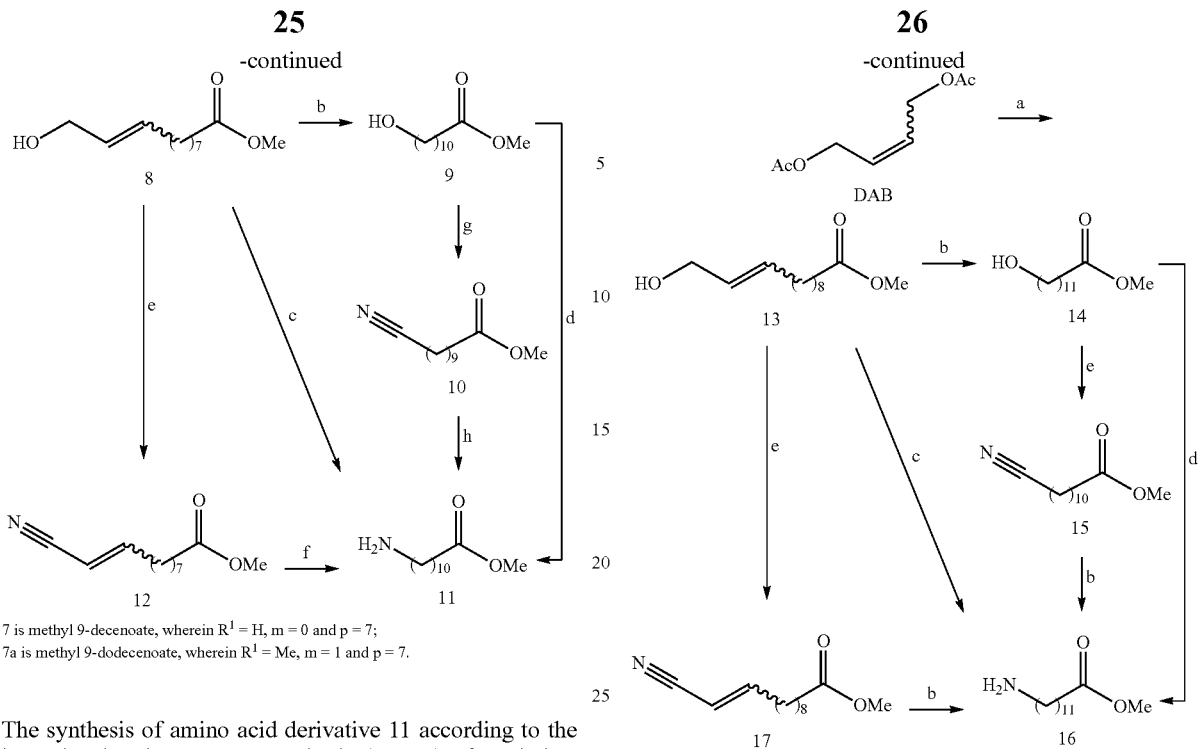

7 is methyl 9-decenoate, wherein $R^1$ = H, m = 0 and p = 7;
7a is methyl 9-dodecenoate, wherein $R^1$ = Me, m = 1 and p = 7.

The synthesis of amino acid derivative 11 according to the invention involves cross metathesis (Step a) of methyl-9-decenoate (7) or methyl 9-dodecenoate (7a) with 1,4-diacetoxy-2-butene (DAB), followed by hydrolysis to yield 8, hydrogenation (Step b) yields 9, subjecting 9 to a Ruthenium pincer complex represented by the structure of Formula 4 under ammonia (Step d) yields amino acid derivative 11. Alternatively, subjecting 8 to hydrogenation (Step b) yields 9, subjecting 9 to Stahl oxidation conditions with ammonia (Step g) yields the nitrile ester 10, hydrogenation (Step h) yields amino acid derivative 11. Additionally, subjecting 8 to Stahl oxidation conditions with ammonia (Step e) yields the unsaturated nitrile ester 12, hydrogenation (Step f) yields amino acid derivative 11. Alternatively, amino acid derivative 11 can be obtained from 8 in the presence of a Ruthenium pincer complex represented by the structure of Formula 4 with ammonia and hydrogen (Step c). One advantage of Stahl's oxidation is nitriles 10 and 12 can be distilled to high purity before hydrogenation to amino acid derivative 11. Reaction conditions: a) (i) C711 (10 ppm), 3 eq 1,4-diacetoxy-2-butene, 60° C. (74% yield), (ii) MeOH/MeONa, b) $PtO_2/H_2$, c) a Ruthenium pincer complex represented by the structure of Formula 4, ammonia, and hydrogen, d) a Ruthenium pincer complex represented by the structure of Formula 4 and ammonia, and e) Stahl oxidation conditions in ammonia, B. L. Ryland; S. S. Stahl, *Angew. Chem. Int. Ed.* (2014), 53, 8824-8838; J. Kim; S. S. Stahl, *ACS Catal.* (2013), 3, 1652-1656.

In another aspect the invention relates particularly to the synthesis of amino acid derivative 16, as shown in Scheme 4.

Scheme 4

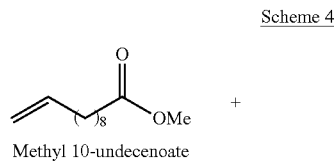

Methyl 10-undecenoate

The synthesis of amino acid derivative 16 according to the invention involves cross metathesis (Step a) of methyl 10-undecenoate with DAB, followed by hydrolysis to yield 13, hydrogenation (Step b) yields 14, subjecting 14 to a Ruthenium pincer complex represented by the structure of Formula 4 under ammonia (Step d) yields amino acid derivative 16. Alternatively, subjecting 14 to Stahl oxidation conditions with ammonia (Step e) yields the nitrile ester 15, hydrogenation (Step b) yields amino acid derivative 16. Additionally, subjecting 13 to Stahl oxidation conditions with ammonia (Step e) yields the unsaturated nitrile ester 17, hydrogenation (Step b) yields amino acid derivative 16. Alternatively, amino acid derivative 16 can be obtained from 13 in the presence of a Ruthenium pincer complex represented by the structure of Formula 4 with ammonia and hydrogen (Step c). One advantage of Stahl's oxidation is nitriles 15 and 17 can be distilled to high purity before hydrogenation to amino acid derivative 16. Reaction conditions: a) (i) C711 (10 ppm), 3 eq 1,4-diacetoxy-2-butene, 60° C., (ii) MeOH/MeONa, b) $PtO_2/H_2$, c) a Ruthenium pincer complex represented by the structure of Formula 4, ammonia, and hydrogen, d) a Ruthenium pincer complex represented by the structure of Formula 4 and ammonia, and e) Stahl oxidation conditions in ammonia.

In another aspect the invention relates to the synthesis of amino acid derivative 11, as shown in Scheme 5.

Scheme 5

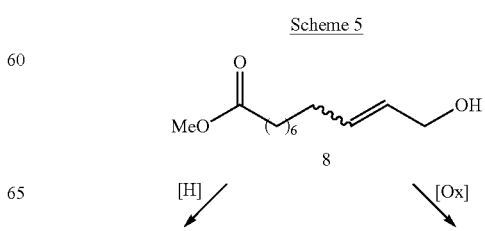

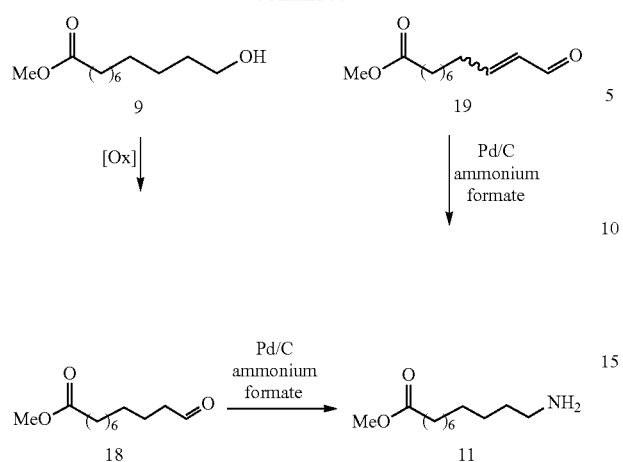

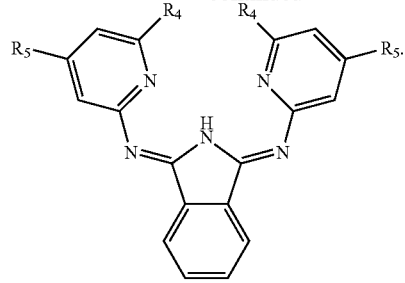

1,3-Bis(arylimino)isoindolines
R_4, R_5 = H
R_4, R_5 = Me
R_4 = H; R_5 = Me
R_4 = Me; R_5 = H
Siegl, W. O.
*J. Org. Chem.* 1977, 42, 1872

Reaction conditions: [H] $PtO_2/H_2$, [Ox] Stahl oxidation conditions.

In another aspect the invention relates to the synthesis of methyl 12-aminodo decenoate, as shown in Scheme 6.

In step (j) methyl 12-oxo-10-dodecenoate can be subjected to ammonia and hypochlorite or to ammonia and CuCl to form methyl 11 1-cyano-10-undecenoate. In step (k) methyl 11-cyano-10-undecenoate gives methyl 12-aminododecanoate in the presence of Raney Ni ($H_2/NH_3$).

In another aspect the invention relates to the synthesis of methyl 12-amino-10-dodecenoate, as shown in Scheme 7.

Scheme 6

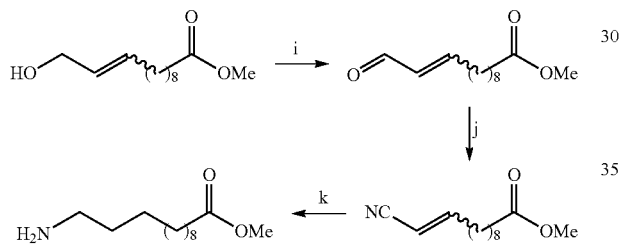

The synthesis of methyl 12-oxo-10-dodecenoate, according to the invention, involves the oxidation of methyl 12-hydroxy-10-dodecenoate (Step i) in the presence of [(TMEDA)Cu(μ-OH)]_2Cl_2. Other Cu catalysts which may be used in step (i) comprise ligands such as β-diketiminates or 1,3-bis(arylimino)isoindolines, selected from, but not limited to:

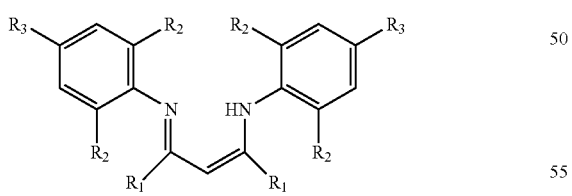

β-Diketiminate
R_1 = Me; R_2, R_3 = Me
R_1 = Me; R_2 = Me; R_3 = H
R_1 = Me; R_2 = $^i$Pr; R_3 = H
R_1 = Me; R_2, R_3 = H
R_1 = $^t$Bu; R_2, R_3 = Me
R_1 = $^t$Bu; R_2 = Me; R_3 = H
R_1 = $^t$Bu; R_2 = $^i$Pr; R_3 = H
Mindiola, D. J.; Warren, T. H.; Holland, P. L.
*Inorganic Syntheses* 2010, 35, 1.

Scheme 7

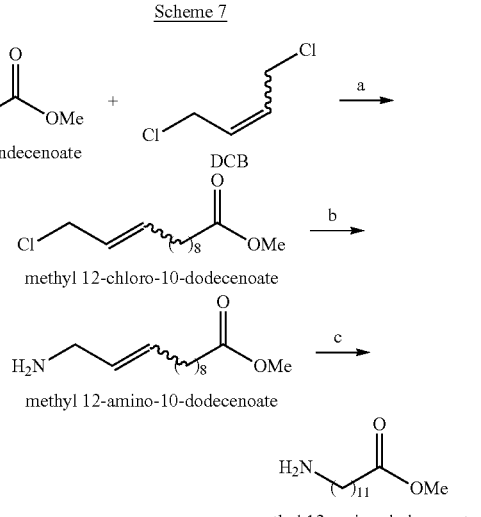

a) C627, 40° C., 4 Torr, 2.5 h (84.4% yield) b) CuCl cat, NH_3 (gas) (78.3% yield) c) Raney Ni, H_2 (99% yield)

The synthesis of methyl 12-chloro-10-dodecenoate, according to Scheme 7, involves the cross-metathesis between methyl 10-undecenoate and DCB in the presence of C627. Further, methyl 12-chloro-10-dodecenoate is converted to the corresponding amine in the presence of CuCl and ammonia, giving methyl 12-amino-10-dodecenoate which is converted to methyl 12-amino-dodecanoate in the presence of Raney Ni and H_2.

Embodiments herein are not meant to be construed in a limiting sense. Various modifications in form and detail of the embodiments of the invention, as well as other aspects and variations of the invention, will be apparent to the skilled artisan in light of the following detailed description and examples.

DETAILED DESCRIPTION OF THE INVENTION

Terminology and Definitions

Unless otherwise indicated, the invention is not limited to specific reactants, substituents, catalysts, reaction conditions, or the like, as such may vary. It is also to be understood that the terminology used herein is for the purpose of describing particular embodiments only and is not to be interpreted as being limiting.

As used in the specification and the appended claims, the singular forms "a," "an," and "the" include plural referents unless the context clearly dictates otherwise. Thus, for example, reference to "an α-olefin" includes a single α-olefin as well as a combination or mixture of two or more α-olefins, reference to "a substituent" encompasses a single substituent as well as two or more substituents, and the like.

As used in the specification and the appended claims, the terms "for example," "for instance," "such as," or "including" are meant to introduce examples that further clarify more general subject matter. Unless otherwise specified, these examples are provided only as an aid for understanding the invention, and are not meant to be limiting in any fashion.

One of skill in the art, would recognize that amino acids represented by the structure of Formula 1 generally exist primarily in their zwitterionic form

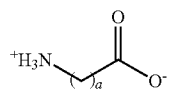

when R=—H. For simplicity, applicants represent all compounds represented by the structure of Formula 1 by the following structure

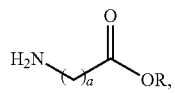

with the recognition that some may also have zwitterionic tautomers.

The geometry of the olefins described in this patent application may be of (E) conformation, or of (Z) conformation, or of a mixture of (E) and (Z) conformations. Applicants have represented a mixture of double-bond isomers by using a squiggly bond "⌇." For example, as represented herein, structure

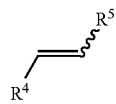

exemplifies either the (E) conformation

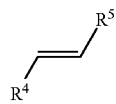

or the (Z) conformation

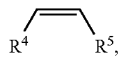

or can represent a mixture of (E) and (Z) conformations.

In this specification and in the claims that follow, reference will be made to a number of terms, which shall be defined to have the following meanings:

The term tandem amination-reduction reaction refers to a consecutive series of organic reactions, which take place one chemical transformation at a time. The reactions do not require workup or isolation of the intermediates. As described and used herein, the tandem amination-reduction reaction is a process in which a compound, containing at least one carbon-carbon double bond (—CH=CH—), which can be in the (E) conformation or in the (Z) conformation or in a mixture of (E) and (Z) conformations, and at least one hydroxyl group (—OH) is contacted with a Ruthenium pincer complex represented by the structure of Formula 4 in the presence of ammonia ($NH_3$) and molecular hydrogen ($H_2$), wherein the at least one carbon-carbon double bond (—CH=CH—) is hydrogenated to a carbon-carbon single bond (—$CH_2$—$CH_2$—) and the at least one hydroxyl group (—OH) is converted to an amino group (—$NH_2$).

A hydrogenation reaction as used herein, is a chemical reaction between molecular hydrogen ($H_2$) and another compound, typically in the presence of a catalyst. This reaction type is also referred to as a reduction of organic compounds. Hydrogenation reduces double bonds. For example, carbon-carbon double bonds (—CH=CH—) can be hydrogenated or reduced to carbon-carbon single bonds (—$CH_2$—$CH_2$—) via treatment with ($H_2$), typically in the presence of a catalyst (e.g., a hydrogenation catalyst). The terms "hydrogenation" and "reduction" are used interchangeably herein.

The term "pincer" refers to specific types of transition metal ligands (pincer ligands), and are so named due to the manner in which they bind to transition metals to provide pincer complexes. Generally, pincer ligands bind to transition metals at three adjacent coplanar sites. For example, in one embodiment, a pincer ligand may be a tridentate ligand that is coordinated to the transition metal in the following arrangement,

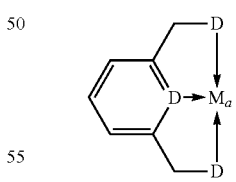

wherein: $M_a$ is a transition metal (e.g., Pd, Ru, Rh, Ni, Ir), and D is a donor atom (e.g., independently selected from C, O, S, N, and P). Examples of pincer ligands and pincer complexes are known in the art and are generally described in the literature, for example in Morales-Morales, David and Jensen, Craig M., *The Chemistry of Pincer Compounds*, Amsterdam, Elsevier (2007) and Gunanathan, C., and Milstein, D., *Chem. Rev.* (2014), 114, 12024-12087.

The term "alkyl" as used herein refers to a linear, branched, or cyclic saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups, such as cyclopentyl, cyclohexyl, and the like. Generally, although not necessarily, alkyl groups herein contain 1 to about 12 carbon atoms. The term "lower alkyl" refers to an alkyl group of 1 to 6 carbon atoms, and the specific term "cycloalkyl" refers to a cyclic alkyl group, typically having 4 to 8, or 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. In another aspect, alkenyl groups herein contain 2 to about 12 carbon atoms. The term "lower alkenyl" refers to an alkenyl group of 2 to 6 carbon atoms, and the specific term "cycloalkenyl" refers to a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24, or 2 to about 12, carbon atoms containing at least one triple bond, such as ethynyl, n-propynyl, and the like. The term "lower alkynyl" refers to an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein refers to an alkyl group bound through a single, terminal ether linkage; that is, an "alkoxy" group may be represented as —O-alkyl where alkyl is as defined above. A "lower alkoxy" group refers to an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Aryl groups contain 5 to 24 carbon atoms, or 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Aryloxy groups contain 5 to 24 carbon atoms, or 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Alkaryl and aralkyl groups contain 6 to 24 carbon atoms, or 6 to 16 carbon atoms. Alkaryl groups include, without limitation, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclo hexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, —(CO)-aralkyl, —(CO)-alkaryl, —(CO)-alkenyl, or —(CO)-alkynyl, and the term "acyloxy" refers to substituents having the formula —O(CO)-alkyl, —O(CO)-aryl, —O(CO)-aralkyl, —O(CO)-alkaryl, —O(CO)-alkenyl, —O(CO)-alkynyl wherein "alkyl," "aryl," "aralkyl," "alkaryl," "alkenyl," and "alkynyl" are as defined above.

The terms "cyclic" and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic, or polycyclic.

The terms "halo" and "halogen" are used in the conventional sense to refer to a chloro, bromo, fluoro, or iodo substituent.

"Hydrocarbyl" refers to univalent hydrocarbyl radicals containing 1 to about 30 carbon atoms, or 1 to about 24 carbon atoms, or 1 to about 12 carbon atoms, including linear, branched, cyclic, saturated, and unsaturated species, such as alkyl groups, alkenyl groups, alkynyl groups, aryl groups, and the like. The term "lower hydrocarbyl" intends a hydrocarbyl group of 1 to 6 carbon atoms, or 1 to 4 carbon atoms, and the term "hydrocarbylene" refers to a divalent hydrocarbyl moiety containing 1 to about 30 carbon atoms, or 1 to about 24 carbon atoms, or 1 to about 12 carbon atoms, including linear, branched, cyclic, saturated, and unsaturated species. The term "lower hydrocarbylene" refers to a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and heteroatom-containing hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus, or silicon, typically nitrogen, oxygen, or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include without limitation alkoxyaryl, alkylsulfanyl-substituted alkyl, N-alkylated amino alkyl, and the like. Examples of heteroaryl substituents include without limitation pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups include without limitation pyrrolidino, morpholino, piperazino, piperidino, etc.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups referred to herein as "Fn," such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO—), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ haloalkyl)), di-($C_1$-$C_{24}$ haloalkyl)-substituted carbamoyl (—(CO)—N($C_1$-$C_{24}$ haloalkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl (—(CO)—N($C_1$-$C_{24}$ alkyl) ($C_5$-$C_{24}$ aryl), thiocarbamoyl (—(CS)—NH$_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)$_2$), di-N—($C_1$-$C_{24}$ alkyl), N—($C_5$-$C_{24}$ aryl)-substituted thiocarbamoyl (—(CS)—N($C_1$-$C_{24}$ alkyl)($C_5$-$C_{24}$ aryl), carbamido (—NH—(CO)—NH$_2$), cyano (—C≡N), cyanato (—O—C≡N), thiocyanato (—S—C≡N), isocyanate (—N=C=O), thioisocyanate (—N=C=S), formyl (—(CO)—H), thioformyl (—(CS)—H), amino (—NH$_2$), mono-($C_1$-$C_{24}$ alkyl)-substituted amino (—NH($C_1$-$C_{24}$ alkyl), di-($C_1$-$C_{24}$ alkyl)-substituted amino (—N($C_1$-$C_{24}$ alkyl)$_2$), mono-($C_5$-$C_{24}$ aryl)-substituted amino (—NH($C_5$-$C_{24}$ aryl), di-($C_5$-$C_{24}$ aryl)-substituted amino (—N($C_5$-$C_{24}$ aryl)$_2$), $C_2$-$C_{24}$ alkylamido (—NH—(CO)-alkyl), $C_6$-$C_{24}$ arylamido (—NH—(CO)-aryl), imino (—CR=NH where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R includes without limitation hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O—), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_1$-$C_{24}$ monoalkylaminosulfonyl (—SO$_2$—N(H) alkyl), $C_1$-$C_{24}$ dialkylaminosulfonyl (—SO$_2$—N(alkyl)$_2$), $C_5$-$C_{24}$ arylsulfonyl (—SO$_2$-aryl), boryl (—BH$_2$), borono (—B(OH)$_2$), boronato (—B(OR)$_2$ where R includes without limitation alkyl or other hydrocarbyl), phosphono (—P(O)(OH)$_2$), phosphonato (—P(O)(O—)$_2$), phosphinato (—P(O)(O$^-$)), phospho (—PO$_2$), and phosphino (—PH$_2$); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

By "functionalized" as in "functionalized hydrocarbyl," "functionalized alkyl," "functionalized olefin," "functionalized cyclic olefin," and the like, is meant that in the hydrocarbyl, alkyl, olefin, cyclic olefin, or other moiety, at least one hydrogen atom bound to a carbon (or other) atom is replaced with one or more functional groups, such as those described hereinabove. The term "functional group" is meant to include any functional species that is suitable for the uses described herein.

In addition, the aforementioned functional groups may, if a particular group permits, be further substituted with one or more additional functional groups or with one or more hydrocarbyl moieties, such as those specifically mentioned above. Analogously, the above-mentioned hydrocarbyl moieties may be further substituted with one or more functional groups or additional hydrocarbyl moieties as noted above.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

For the purposes of this invention, an unsaturated fatty acid ester shall be defined as the ester product of an unsaturated fatty acid and an alcohol. The alcohol can be any monohydric, dihydric, or polyhydric alcohol that is capable of condensing with the unsaturated fatty acid to form the corresponding unsaturated fatty acid ester. Typically, the alcohol contains at least one carbon atom. Typically, the alcohol contains less than about 20 carbon atoms, less than about 12 carbon atoms, and less than about 8 carbon atoms. The carbon atoms may be arranged in a straight-chain or branched structure, and may be substituted with a variety of substituents, such as those previously disclosed hereinabove in connection with the fatty acid, including the aforementioned alkyl, cycloalkyl, monocyclic aromatic, arylalkyl, alkylaryl, hydroxyl, halogen, ether, ester, aldehyde and keto substituents. The alcohol is a straight-chain or branched $C_{1-12}$ alkanol. An alcohol is the trihydric alcohol glycerol, the fatty acid esters of which are known as "glycerides." Other alcohols include methanol and ethanol.

Non-limiting examples of suitable unsaturated fatty acids include 3-hexenoic (hydro sorbic), trans-2-heptenoic, 2-octenoic, 2-nonenoic, cis- and trans-4-decenoic, 9-decenoic (caproleic), 10-undecenoic (undecylenic), cis-5-dodecenoic, cis-4-dodecenoic (linderic), tridecenoic, cis-9-tetradeceonic (myristoleic), cis-5-tetradeceonic, cis-4-tetradeceonic, pentadecenoic, cis-9-hexadecenoic (cis-9-palmitoelic), trans-9-hexadecenoic (trans-9-palmitoleic), 9-heptadecenoic, cis-6-octadecenoic (petroselinic), trans-6-octadecenoic (petroselaidic), cis-9-octadecenoic (oleic), trans-9-octadecenoic (elaidic), cis-11-octadecenoic, trans-11-octadecenoic, cis-5-eicosenoic, cis-9-eicosenoic (gadoleic), cis-11-docosenoic (cetoleic), cis-13-docosenoic (erucic), trans-13-docosenoic (brassidic), cis-15-tetracosenoic (selacholeic), cis-17-hexacosenoic (ximenic), and cis-21-triacontenoic (lumequeic) acids, as well as 2,4-hexadienoic (sorbic), cis-9-cis-12-octadecadienoic (linoleic), cis-9-cis-12-cis-15-octadecatrienoic (linolenic), eleostearic, 12-hydroxy-cis-9-octadecenoic (ricinoleic), 14-hydroxy-cis-11-eicosenoic (lesquerolic) and like acids. Unsaturated fatty acids can be obtained commercially or synthesized by saponifying fatty acid esters, this method being known to those skilled in the art.

Cyclic Olefin Metathesis Catalysts

Cyclic olefin metathesis catalysts, that may be used in the invention, are preferably Group 8 transition metal complexes, represented by the structure of Formula (I):

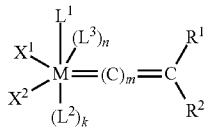

Formula (I)

wherein:
M is a Group 8 transition metal;
$L^1$, $L^2$, and $L^3$ are neutral electron donor ligands;
n is 0 or 1, such that $L^3$ may or may not be present;
m is 0, 1, or 2;
k is 0 or 1;
$X^1$ and $X^2$ are anionic ligands; and $R^1$ and $R^2$ are independently selected from hydrogen, hydrocarbyl, substituted hydrocarbyl, heteroatom-containing hydrocarbyl, substituted heteroatom-containing hydrocarbyl, and functional groups, wherein any two or more of $X^1$, $X^2$, $L^1$, $L^2$, $L^3$, $R^1$, and $R^2$ can be taken together to form one or more cyclic groups, and further wherein any one or more of $X^1$, $X^2$, $L^1$, $L^2$, $L^3$, $R^1$, and $R^2$ may optionally be attached to a support.

Additionally, in Formula (I), one or both of $R^1$ and $R^2$ may have the structure $-(W)_n-U^+V^-$, in which W is selected from hydrocarbylene, substituted hydrocarbylene, heteroatom-containing hydrocarbylene, or substituted heteroatom-containing hydrocarbylene; U is a positively charged Group 15 or Group 16 element substituted with hydrogen, hydrocarbyl, substituted hydrocarbyl, heteroatom-containing hydrocarbyl, or substituted heteroatom-containing hydrocarbyl; V is a negatively charged counterion; and n is zero or 1. Furthermore, $R^1$ and $R^2$ may be taken together to form an indenylidene moiety, preferably phenylindenylidene. Preferred cyclic olefin metathesis catalysts contain Ru or Os as the Group 8 transition metal, with Ru particularly preferred.

A first group of cyclic olefin metathesis catalysts, commonly referred to as First Generation Grubbs-type catalysts, are represented by the structure of Formula (I). For the first group of cyclic olefin metathesis catalysts, M is a Group 8 transition metal, m is 0, 1, or 2, and n, $X^1$, $X^2$, $L^1$, $L^2$, $L^3$, $R^1$, and $R^2$ are described as follows. For the first group of cyclic olefin metathesis catalysts, n is 0, and $L^1$ and $L^2$ are independently selected from phosphine, sulfonated phosphine, phosphite, phosphinite, phosphonite, arsine, stibine, ether (including cyclic ethers), amine, amide, imine, sulfoxide, carboxyl, nitrosyl, pyridine, substituted pyridine, imidazole, substituted imidazole, pyrazine, substituted pyrazine and thioether. Exemplary ligands are trisubstituted phosphines. Preferred trisubstituted phosphines are of the formula $PR^{H1}R^{H2}R^{H3}$, where $R^{H1}$, $R^{H2}$, and $R^{H3}$ are each independently substituted or unsubstituted aryl or $C_1$-$C_{10}$ alkyl, particularly primary alkyl, secondary alkyl, or cycloalkyl. In the most preferred, $L^1$ and $L^2$ are independently selected from the group consisting of trimethylphosphine ($PMe_3$), triethylphosphine ($PEt_3$), tri-n-butylphosphine ($PBu_3$), tri(ortho-tolyl)phosphine (P-o-$tolyl_3$), tri-tert-butylphosphine (P-tert-$Bu_3$), tricyclopentylphosphine ($PCyclopentyl_3$), tricyclohexylphosphine ($PCy_3$), triisopropylphosphine (P-i-$Pr_3$), trioctylphosphine ($POct_3$), triisobutylphosphine, (P-i-$Bu_3$), triphenylphosphine ($PPh_3$), tri(pentafluorophenyl)phosphine ($P(C_6F_5)_3$), methyldiphenylphosphine ($PMePh_2$), dimethylphenylphosphine ($PMe_2Ph$), and diethylphenylphosphine ($PEt_2Ph$). Alternatively, $L^1$ and $L^2$ may be independently selected from phosphabicycloalkane (e.g., monosubstituted 9-phosphabicyclo-[3.3.1] nonane, or monosubstituted 9-phosphabicyclo [4.2.1]nonane], such as cyclohexylphoban, isopropylphoban, ethylphoban, methylphoban, butylphoban, pentylphoban, and the like). $X^1$ and $X^2$ are anionic ligands, and may be the same or different, or are linked together to form a cyclic group, typically, although not necessarily, a five- to eight-membered ring. In preferred embodiments, $X^1$ and $X^2$ are each independently hydrogen, halide, or one of the following groups: $C_1$-$C_{20}$ alkyl, $C_5$-$C_{24}$ aryl, $C_1$-$C_{20}$ alkoxy, $C_5$-$C_{24}$ aryloxy, $C_2$-$C_{20}$ alkoxycarbonyl, $C_6$-$C_{24}$ aryloxycarbonyl, $C_2$-$C_{24}$ acyl, $C_2$-$C_{24}$ acyloxy, $C_1$-$C_{20}$ alkylsulfonato, $C_5$-$C_{24}$ arylsulfonato, $C_1$-$C_{20}$ alkylsulfanyl, $C_5$-$C_{24}$ arylsulfanyl, $C_1$-$C_{20}$ alkylsulfinyl, $NO_3$, $-N=C=O$, $-N=C=S$, or $C_5$-$C_{24}$ arylsulfinyl. Optionally, $X^1$ and $X^2$ may be substituted with one or more moieties selected from $C_1$-$C_{12}$ alkyl, $C_1$-$C_{12}$ alkoxy, $C_5$-$C_{24}$ aryl, and halide, which may, in turn, with the exception of halide, be further substituted with one or more groups selected from halide, $C_1$-$C_6$ alkyl, $C_1$-$C_6$ alkoxy, and phenyl. In more preferred embodiments, $X^1$ and $X^2$ are halide, benzoate, $C_2$-$C_6$ acyl, $C_2$-$C_6$ alkoxycarbonyl, $C_1$-$C_6$ alkyl, phenoxy, $C_1$-$C_6$ alkoxy, $C_1$-$C_6$ alkylsulfanyl, aryl, or $C_1$-$C_6$ alkylsulfonyl. In even more preferred embodiments, $X^1$ and $X^2$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethanesulfonate. In the most preferred embodiments, $X^1$ and $X^2$ are each chloride. $R^1$ and $R^2$ are independently selected from hydrogen, hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), heteroatom-containing hydrocarbyl (e.g., heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and substituted heteroatom-containing hydrocarbyl (e.g., substituted heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and functional groups. $R^1$ and $R^2$ may also be linked to form a cyclic group, which may be aliphatic or aromatic, and may contain substituents and/or heteroatoms. Generally, such a cyclic group will contain 4 to 12, preferably 5, 6, 7, or 8 ring atoms.

In preferred cyclic olefin metathesis catalysts, $R^1$ is hydrogen and $R^2$ is selected from $C_1$-$C_{20}$ alkyl, $C_2$-$C_{20}$ alkenyl, and $C_5$-$C_{24}$ aryl, more preferably $C_1$-$C_6$ alkyl, $C_2$-$C_6$ alkenyl, and $C_5$-$C_{14}$ aryl. Still more preferably, $R^2$ is phenyl, vinyl, methyl, isopropyl, or t-butyl, optionally substituted with one or more moieties selected from $C_1$-$C_6$ alkyl, $C_1$-$C_6$ alkoxy, phenyl, and a functional group Fn as defined earlier herein. Most preferably, $R^2$ is phenyl or vinyl substituted with one or more moieties selected from methyl, ethyl, chloro, bromo, iodo, fluoro, nitro, dimethylamino, methyl, methoxy, and phenyl. Optimally, $R^2$ is phenyl or —CH=C(CH$_3$)$_2$.

Any two or more (typically two, three, or four) of $X^1$, $X^2$, $L^1$, $L^2$, $L^3$, $R^1$, and $R^2$ can be taken together to form a cyclic group, including bidentate or multidentate ligands, as disclosed, for example, in U.S. Pat. No. 5,312,940. When any of $X^1$, $X^2$, $L^1$, $L^2$, $L^3$, $R^1$, and $R^2$ are linked to form cyclic groups, those cyclic groups may contain 4 to 12, preferably 4, 5, 6, 7, or 8 atoms, or may comprise two or three of such rings, which may be either fused or linked. The cyclic groups may be aliphatic or aromatic, and may be heteroatom-containing and/or substituted. The cyclic group may, in some cases, form a bidentate ligand or a tridentate ligand. Examples of bidentate ligands include, but are not limited to, bisphosphines, dialkoxides, alkyldiketonates, and aryldiketonates.

A second group of cyclic olefin metathesis catalysts, commonly referred to as Second Generation Grubbs-type catalysts, wherein $L^1$ is a carbene ligand, are represented by the structure of Formula (II):

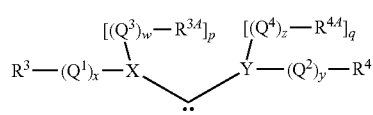

Formula (II)

such that the complex may be represented by the structure of Formula (III):

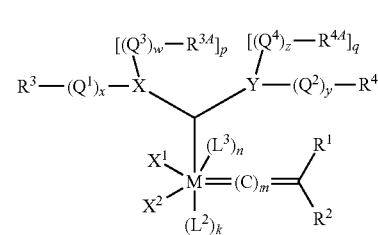

Formula (III)

wherein: M, m, n, $X^1$, $X^2$, $L^2$, $L^3$, $R^1$, and $R^2$ are as defined for the first group of cyclic olefin metathesis catalysts, and the remaining substituents are as follows;

X and Y are heteroatoms typically selected from N, O, S, and P. Since O and S are divalent, p is necessarily zero when X is O or S, q is necessarily zero when Y is O or S, and k is zero or 1. However, when X is N or P, then p is 1, and when Y is N or P, then q is 1.

In a preferred embodiment, both X and Y are N; $Q^1$, $Q^2$, $Q^3$, and $Q^4$ are linkers, e.g., hydrocarbylene (including substituted hydrocarbylene, heteroatom-containing hydrocarbylene, and substituted heteroatom-containing hydrocarbylene, such as substituted and/or heteroatom-containing alkylene) or —(CO)—; and w, x, y, and z are independently zero or 1, meaning that each linker is optional. Preferably, w, x, y, and z are all zero. Further, two or more substituents on adjacent atoms within $Q^1$, $Q^2$, $Q^3$, and $Q^4$ may be linked to form an additional cyclic group; and $R^3$, $R^{3A}$, $R^4$, and $R^{4A}$ are independently selected from hydrogen, hydrocarbyl, substituted hydrocarbyl, heteroatom-containing hydrocarbyl, and substituted heteroatom-containing hydrocarbyl. In addition, X and Y may be independently selected from carbon and one of the heteroatoms mentioned above, preferably no more than one of X or Y is carbon. Also, $L^2$ and $L^3$ may be taken together to form a single bidentate electron-donating heterocyclic ligand. Furthermore, $R^1$ and $R^2$ may be taken together to form an indenylidene moiety, preferably phenylindenylidene. Moreover, $X^1$, $X^2$, $L^2$, $L^3$, X, and Y may be further coordinated to boron or to a carboxylate.

In addition, any two or more of $X^1$, $X^2$, $L^1$, $L^2$, $L^3$, $R^1$, $R^2$, $R^3$, $R^{3A}$, $R^4$, $R^{4A}$, $Q^1$, $Q^2$, $Q^3$ and $Q^4$ can be taken together to form a cyclic group, and any one or more of $X^1$, $X^2$, $L^2$, $L^3$, $Q^1$, $Q^2$, $Q^3$, $Q^4$, $R^1$, $R^2$, $R^3$, $R^{3A}$, $R^4$, and $R^{4A}$ may optionally be attached to a support. Any two or more of $X^1$, $X^2$, $L^1$, $L^2$, $L^3$, $R^1$, $R^2$, $R^3$, $R^{3A}$, $R^4$, and $R^{4A}$ can also be taken to be -A-Fn, wherein "A" is a divalent hydrocarbon moiety selected from alkylene and arylalkylene, wherein the alkyl portion of the alkylene and arylalkylene groups can be linear or branched, saturated or unsaturated, cyclic or acyclic, and substituted or unsubstituted, wherein the aryl portion of the of arylalkylene can be substituted or unsubstituted, and wherein hetero atoms and/or functional groups may be present in either the aryl or the alkyl portions of the alkylene and arylalkylene groups, and Fn is a functional group, or together to form a cyclic group, and any one or more of $X^1$, $X^2$, $L^2$, $L^3$, $Q^1$, $Q^2$, $Q^3$, $Q^4$, $R^1$, $R^2$, $R^3$, $R^{3A}$, $R^4$, and $R^{4A}$ may optionally be attached to a support.

A particular class of carbene ligands represented by the structure of Formula (II), where $R^{3A}$ and $R^{4A}$ are linked to form a cyclic group and at least one of X or Y is a nitrogen, or at least one of $Q^3$ or $Q^4$ is a heteroatom-containing hydrocarbylene or substituted heteroatom-containing hydrocarbylene, where at least one heteroatom is a nitrogen, are commonly referred to as N-heterocyclic carbene (NHC)

ligands. Preferably, $R^{3A}$ and $R^{4A}$ are linked to form a cyclic group so that the carbene ligand is represented by the structure of Formula (IV):

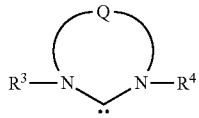

Formula (IV)

wherein: $R^3$ and $R^4$ are as defined for the second group of cyclic olefin metathesis catalysts above, with preferably at least one of $R^3$ and $R^4$, and more preferably both $R^3$ and $R^4$, being alicyclic or aromatic of one to about five rings, and optionally containing one or more heteroatoms and/or substituents. Q is a linker, typically a hydrocarbylene linker, including substituted hydrocarbylene, heteroatom-containing hydrocarbylene, and substituted heteroatom-containing hydrocarbylene linkers, wherein two or more substituents on adjacent atoms within Q may also be linked to form an additional cyclic structure, which may be similarly substituted to provide a fused polycyclic structure of two to about five cyclic groups. Q is often, although not necessarily, a two-atom linkage or a three-atom linkage.

Examples of N-heterocyclic carbene (NHC) ligands and acyclic diaminocarbene ligands suitable as $L^1$ thus include, but are not limited to, the following where DIPP or DiPP is diisopropylphenyl and Mes is 2,4,6-trimethylphenyl.

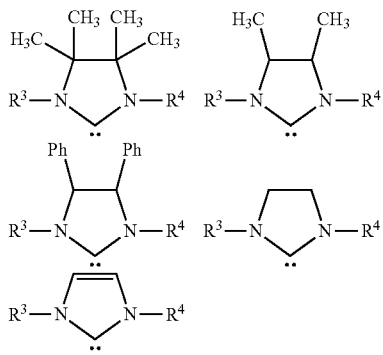

Additional examples of N-heterocyclic carbene (NHC) ligands and acyclic diaminocarbene ligands suitable as $L^1$ thus include, but are not limited to the following:

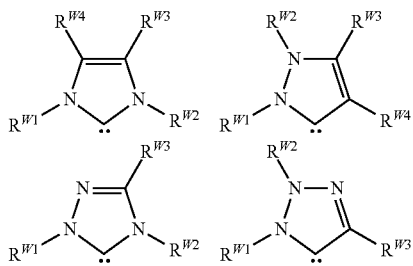

wherein: $R^{W1}$, $R^{W2}$, $R^{W3}$, $R^{W4}$ are independently hydrogen, unsubstituted hydrocarbyl, substituted hydrocarbyl, or heteroatom containing hydrocarbyl, and where one or both of $R^{W3}$ and $R^{W4}$ may be in independently selected from halo-gen, nitro, amido, carboxyl, alkoxy, aryloxy, sulfonyl, carbonyl, thio, or nitroso groups. Additional Examples of N-heterocyclic carbene (NHC) ligands suitable as $L^1$ are further described in U.S. Pat. Nos. 7,378,528; 7,652,145; 7,294,717; 6,787,620; 6,635,768; and 6,552,139. Additionally, thermally activated N-Heterocyclic Carbene Precursors as disclosed in U.S. Pat. No. 6,838,489 may also be used with the present invention.

When M is Ruthenium, then, the preferred complexes are represented by the structure of Formula (V):

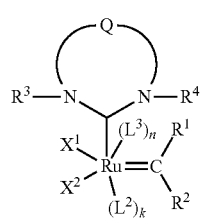

Formula (V)

In a more preferred embodiment, Q is a two-atom linkage having the structure —$CR^{11}R^{12}$—$CR^{13}R^{14}$— or —$CR^{11}$=$CR^{13}$—, preferably —$CR^{11}R^{12}$—$CR^{13}R^{14}$—, wherein $R^{11}$, $R^{12}$, $R^{13}$, and $R^{14}$ are independently selected from hydrogen, hydrocarbyl, substituted hydrocarbyl, heteroatom-containing hydrocarbyl, substituted heteroatom-containing hydrocarbyl, and functional groups. Examples of functional groups here include without limitation carboxyl, $C_1$-$C_{20}$ alkoxy, $C_5$-$C_{24}$ aryloxy, $C_2$-$C_{20}$ alkoxycarbonyl, $C_5$-$C_{24}$ alkoxycarbonyl, $C_2$-$C_{24}$ acyloxy, $C_1$-$C_{20}$ alkylthio, $C_5$-$C_{24}$ arylthio, $C_1$-$C_{20}$ alkylsulfonyl, and $C_1$-$C_{20}$ alkylsulfinyl, optionally substituted with one or more moieties selected from $C_1$-$C_{12}$ alkyl, $C_1$-$C_{12}$ alkoxy, $C_5$-$C_{14}$ aryl, hydroxyl, sulfhydryl, formyl, and halide. $R^{11}$, $R^{12}$, $R^{13}$, and $R^{14}$ are preferably independently selected from hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, phenyl, and substituted phenyl. Alternatively, any two of $R^{11}$, $R^{12}$, $R^{13}$, and $R^{14}$ may be linked together to form a substituted or unsubstituted, saturated or unsaturated ring structure, e.g., a $C_4$-$C_{12}$ alicyclic group or a $C_5$ or $C_6$ aryl group, which may itself be substituted, e.g., with linked or fused alicyclic or aromatic groups, or with other substituents.

In one further aspect, any one or more of $R^{11}$, $R^{12}$, $R^{13}$, and $R^{14}$ comprises one or more of the linkers. Additionally, $R^3$ and $R^4$ may be unsubstituted phenyl or phenyl substituted with one or more substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide. Furthermore, $X^1$ and $X^2$ may be halogen. When $R^3$ and $R^4$ are aromatic, they are typically although not necessarily composed of one or two aromatic rings, which may or may not be substituted, e.g., $R^3$ and $R^4$ may be phenyl, substituted phenyl, biphenyl, substituted biphenyl, or the like. In one preferred embodiment, $R^3$ and $R^4$ are the same and are each unsubstituted phenyl or phenyl substituted with up to three substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide. Preferably, any substituents present are hydrogen, $C_1$-$C_{12}$ alkyl, $C_1$-$C_{12}$ alkoxy, $C_5$-$C_{14}$ aryl, substituted $C_5$-$C_{14}$ aryl, or halide. As an example, $R^3$ and $R^4$ are mesityl (i.e., Mes as defined herein).

In a third group of cyclic olefin metathesis catalysts represented by the structure of Formula (I), M, m, n, $X^1$, $X^2$, $R^1$, and $R^2$ are as defined for the first group of cyclic olefin metathesis catalysts, $L^1$ is a strongly coordinating neutral electron donor ligand such as any of those described for the first and second group of cyclic olefin metathesis catalysts, and $L^2$ and $L^3$ are weakly coordinating neutral electron donor ligands in the form of optionally substituted heterocyclic groups. Again, n is zero or 1, such that $L^3$ may or may not be present. Generally, in the third group of cyclic olefin metathesis catalysts, $L^2$ and $L^3$ are optionally substituted five- or six-membered monocyclic groups containing 1 to 4, preferably 1 to 3, most preferably 1 to 2 heteroatoms, or are optionally substituted bicyclic or polycyclic structures composed of 2 to 5 such five- or six-membered monocyclic groups. If the heterocyclic group is substituted, it should not be substituted on a coordinating heteroatom, and any one cyclic moiety within a heterocyclic group will generally not be substituted with more than 3 substituents.

For the third group of cyclic olefin metathesis catalysts, examples of $L^2$ and $L^3$ include, without limitation, heterocycles containing nitrogen, sulfur, oxygen, or a mixture thereof.

Examples of nitrogen-containing heterocycles appropriate for $L^2$ and $L^3$ include pyridine, bipyridine, pyridazine, pyrimidine, bipyridamine, pyrazine, 1,3,5-triazine, 1,2,4-triazine, 1,2,3-triazine, pyrrole, 2H-pyrrole, 3H-pyrrole, pyrazole, 2H-imidazole, 1,2,3-triazole, 1,2,4-triazole, indole, 3H-indole, 1H-isoindole, cyclopenta(b)pyridine, indazole, quinoline, bisquinoline, isoquinoline, bisisoquinoline, cinnoline, quinazoline, naphthyridine, piperidine, piperazine, pyrrolidine, pyrazolidine, quinuclidine, imidazolidine, picolylimine, purine, benzimidazole, bisimidazole, phenazine, acridine, and carbazole. Additionally, the nitrogen-containing heterocycles may be optionally substituted on a non-coordinating heteroatom with a non-hydrogen substituent.

Examples of sulfur-containing heterocycles appropriate for $L^2$ and $L^3$ include thiophene, 1,2-dithiole, 1,3-dithiole, thiepin, benzo(b)thiophene, benzo(c)thiophene, thionaphthene, dibenzothiophene, 2H-thiopyran, 4H-thiopyran, and thioanthrene.

Examples of oxygen-containing heterocycles appropriate for $L^2$ and $L^3$ include 2H-pyran, 4H-pyran, 2-pyrone, 4-pyrone, 1,2-dioxin, 1,3-dioxin, oxepin, furan, 2H-1-benzopyran, coumarin, coumarone, chromene, chroman-4-one, isochromen-1-one, isochromen-3-one, xanthene, tetrahydrofuran, 1,4-dioxan, and dibenzofuran.

Examples of mixed heterocycles appropriate for $L^2$ and $L^3$ include isoxazole, oxazole, thiazole, isothiazole, 1,2,3-oxadiazole, 1,2,4-oxadiazole, 1,3,4-oxadiazole, 1,2,3,4-oxatriazole, 1,2,3,5-oxatriazole, 3H-1,2,3-dioxazole, 3H-1,2-oxathiole, 1,3-oxathiole, 4H-1,2-oxazine, 2H-1,3-oxazine, 1,4-oxazine, 1,2,5-oxathiazine, o-isooxazine, phenoxazine, phenothiazine, pyrano[3,4-b]pyrrole, indoxazine, benzoxazole, anthranil, and morpholine. Preferred $L^2$ and $L^3$ ligands are aromatic nitrogen-containing and oxygen-containing heterocycles, and particularly preferred $L^2$ and $L^3$ ligands are monocyclic N-heteroaryl ligands that are optionally substituted with 1 to 3, preferably 1 or 2, substituents. Specific examples of particularly preferred $L^2$ and $L^3$ ligands are pyridine and substituted pyridines, such as 3-bromopyridine, 4-bromopyridine, 3,5-dibromopyridine, 2,4,6-tribromopyridine, 2,6-dibromopyridine, 3-chloropyridine, 4-chloropyridine, 3,5-dichloropyridine, 2,4,6-trichloropyridine, 2,6-dichloropyridine, 4-iodopyridine, 3,5-diiodopyridine, 3,5-dibromo-4-methylpyridine, 3,5-dichloro-4-methylpyridine, 3,5-dimethyl-4-bromopyridine, 3,5-dimethylpyridine, 4-methylpyridine, 3,5-diisopropylpyridine, 2,4,6-trimethylpyridine, 2,4,6-triisopropylpyridine, 4-(tert-butyl)pyridine, 4-phenylpyridine, 3,5-diphenylpyridine, 3,5-dichloro-4-phenylpyridine, and the like.

In general, any substituents present on $L^2$ and/or $L^3$ are selected from halo, $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, substituted $C_5$-$C_{24}$ heteroaryl, $C_6$-$C_{24}$ alkaryl, substituted $C_6$-$C_{24}$ alkaryl, $C_6$-$C_{24}$ heteroalkaryl, substituted $C_6$-$C_{24}$ heteroalkaryl, $C_6$-$C_{24}$ aralkyl, substituted $C_6$-$C_{24}$ aralkyl, $C_6$-$C_{24}$ heteroaralkyl, substituted $C_6$-$C_{24}$ heteroaralkyl, and functional groups, with suitable functional groups including, without limitation, $C_1$-$C_{20}$ alkoxy, $C_5$-$C_{24}$ aryloxy, $C_2$-$C_{20}$ alkylcarbonyl, $C_6$-$C_{24}$ arylcarbonyl, $C_2$-$C_{20}$ alkylcarbonyloxy, $C_6$-$C_{24}$ arylcarbonyloxy, $C_2$-$C_{20}$ alkoxycarbonyl, $C_6$-$C_{24}$ aryloxycarbonyl, halocarbonyl, $C_2$-$C_{20}$ alkylcarbonato, $C_6$-$C_{24}$ arylcarbonato, carboxy, carboxylato, carbamoyl, mono-($C_1$-$C_{20}$ alkyl)-substituted carbamoyl, di-($C_1$-$C_{20}$ alkyl)-substituted carbamoyl, di-N—($C_1$-$C_{20}$ alkyl), N—($C_5$-$C_{24}$ aryl)-substituted carbamoyl, mono-($C_5$-$C_{24}$ aryl)-substituted carbamoyl, di-($C_6$-$C_{24}$ aryl)-substituted carbamoyl, thiocarbamoyl, mono-($C_1$-$C_{20}$ alkyl)-substituted thiocarbamoyl, di-($C_1$-$C_{20}$ alkyl)-substituted thiocarbamoyl, di-N—($C_1$-$C_{20}$ alkyl)-N—($C_6$-$C_{24}$ aryl)-substituted thiocarbamoyl, mono-($C_6$-$C_{24}$ aryl)-substituted thiocarbamoyl, di-($C_6$-$C_{24}$ aryl)-substituted thiocarbamoyl, carbamido, formyl, thioformyl, amino, mono-($C_1$-$C_{20}$ alkyl)-substituted amino, di-($C_1$-$C_{20}$ alkyl)-substituted amino, mono-($C_5$-$C_{24}$ aryl)-substituted amino, di-($C_5$-$C_{24}$ aryl)-substituted amino, di-N—($C_1$-$C_{20}$ alkyl), N—($C_5$-$C_{24}$ aryl)-substituted amino, $C_2$-$C_{20}$ alkylamido, $C_6$-$C_{24}$ arylamido, imino, $C_1$-$C_{20}$ alkylimino, $C_5$-$C_{24}$ arylimino, nitro, and nitroso. In addition, two adjacent substituents may be taken together to form a ring, generally a five- or six-membered alicyclic or aryl ring, optionally containing 1 to 3 heteroatoms and 1 to 3 substituents as above.

Preferred substituents on $L^2$ and $L^3$ include, without limitation, halo, $C_1$-$C_{12}$ alkyl, substituted $C_1$-$C_{12}$ alkyl, $C_1$-$C_{12}$ heteroalkyl, substituted $C_1$-$C_{12}$ heteroalkyl, $C_5$-$C_{14}$ aryl, substituted $C_5$-$C_{14}$ aryl, $C_5$-$C_{14}$ heteroaryl, substituted $C_5$-$C_{14}$ heteroaryl, $C_6$-$C_{16}$ alkaryl, substituted $C_6$-$C_{16}$ alkaryl, $C_6$-$C_{16}$ heteroalkaryl, substituted $C_6$-$C_{16}$ heteroalkaryl, $C_6$-$C_{16}$ aralkyl, substituted $C_6$-$C_{16}$ aralkyl, $C_6$-$C_{16}$ heteroaralkyl, substituted $C_6$-$C_{16}$ heteroaralkyl, $C_1$-$C_{12}$ alkoxy, $C_5$-$C_{14}$ aryloxy, $C_2$-$C_{12}$ alkylcarbonyl, $C_6$-$C_{14}$ arylcarbonyl, $C_2$-$C_{12}$ alkylcarbonyloxy, $C_6$-$C_{14}$ arylcarbonyloxy, $C_2$-$C_{12}$ alkoxycarbonyl, $C_6$-$C_{14}$ aryloxycarbonyl, halocarbonyl, formyl, amino, mono-($C_1$-$C_{12}$ alkyl)-substituted amino, di-($C_1$-$C_{12}$ alkyl)-substituted amino, mono-($C_5$-$C_{14}$ aryl)-substituted amino, di-($C_5$-$C_{14}$ aryl)-substituted amino, and nitro.

Of the foregoing, the most preferred substituents are halo, $C_1$-$C_6$ alkyl, $C_1$-$C_6$ haloalkyl, $C_1$-$C_6$ alkoxy, phenyl, substituted phenyl, formyl, N,N-di($C_1$-$C_6$ alkyl)amino, nitro, and nitrogen heterocycles as described above (including, for example, pyrrolidine, piperidine, piperazine, pyrazine, pyrimidine, pyridine, pyridazine, etc.).

In certain embodiments, $L^2$ and $L^3$ may also be taken together to form a bidentate or multidentate ligand containing two or more, generally two, coordinating heteroatoms, such as N, O, S, or P, with preferred such ligands being diimine ligands of the Brookhart type. One representative bidentate ligand is represented by the structure of Formula (VI):

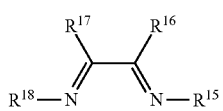

Formula (VI)

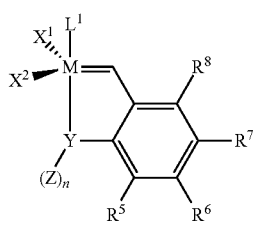

Formula (VII)

wherein: $R^{15}$, $R^{16}$, $R^{17}$, and $R^{18}$ hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, or $C_6$-$C_{24}$ aralkyl), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, or $C_6$-$C_{24}$ aralkyl), heteroatom-containing hydrocarbyl (e.g., $C_1$-$C_{20}$ heteroalkyl, $C_5$-$C_{24}$ heteroaryl, heteroatom-containing $C_6$-$C_{24}$ aralkyl, or heteroatom-containing $C_6$-$C_{24}$ alkaryl), or substituted heteroatom-containing hydrocarbyl (e.g., substituted $C_1$-$C_{20}$ heteroalkyl, $C_5$-$C_{24}$ heteroaryl, heteroatom-containing $C_6$-$C_{24}$ aralkyl, or heteroatom-containing $C_6$-$C_{24}$ alkaryl), or (1) $R^{15}$ and $R^{16}$, (2) $R^{17}$ and $R^{18}$, (3) $R^{16}$ and $R^{17}$, or (4) both $R^{15}$ and $R^{16}$, and $R^{17}$ and $R^{18}$, may be taken together to form a ring, i.e., an N-heterocycle. Preferred cyclic groups in such a case are five- and six-membered rings, typically aromatic rings.

In a fourth group of cyclic olefin metathesis catalysts that are represented by the structure of Formula (I), two of the substituents are taken together to form a bidentate ligand or a tridentate ligand. Examples of bidentate ligands include, but are not limited to, bisphosphines, dialkoxides, alkyldiketonates, and aryldiketonates. Specific examples include —P(Ph)$_2$CH$_2$CH$_2$P(Ph)$_2$-, —As(Ph)$_2$CH$_2$CH$_2$As(Ph$_2$)-, —P(Ph)$_2$CH$_2$CH$_2$C(CF$_3$)$_2$O—, binaphtholate dianions, pinacolate dianions, —P(CH$_3$)$_2$(CH$_2$)$_2$P(CH$_3$)$_2$—, and —OC(CH$_3$)$_2$(CH$_3$)$_2$CO—. Preferred bidentate ligands are —P(Ph)$_2$CH$_2$CH$_2$P(Ph)$_2$- and —P(CH$_3$)$_2$(CH$_2$)$_2$P(CH$_3$)$_2$—. Tridentate ligands include, but are not limited to, (CH$_3$)$_2$NCH$_2$CH$_2$P(Ph)CH$_2$CH$_2$N(CH$_3$)$_2$. Other preferred tridentate ligands are those in which any three of $X^1$, $X^2$, $L^1$, $L^2$, $L^3$, $R^1$, and $R^2$ (e.g., $X^1$, $L^1$, and $L^2$) are taken together to be cyclopentadienyl, indenyl, or fluorenyl, each optionally substituted with $C_2$-$C_{20}$ alkenyl, $C_2$-$C_{20}$ alkynyl, $C_1$-$C_{20}$ alkyl, $C_5$-$C_{20}$ aryl, $C_1$-$C_{20}$ alkoxy, $C_2$-$C_{20}$ alkenyloxy, $C_2$-$C_{20}$ alkynyloxy, $C_5$-$C_{20}$ aryloxy, $C_2$-$C_{20}$ alkoxycarbonyl, $C_1$-$C_{20}$ alkylthio, $C_1$-$C_{20}$ alkylsulfonyl, or $C_1$-$C_{20}$ alkylsulfinyl, each of which may be further substituted with $C_1$-$C_6$ alkyl, halide, $C_1$-$C_6$ alkoxy, or with a phenyl group optionally substituted with halide, $C_1$-$C_6$ alkyl, or $C_1$-$C_6$ alkoxy. More preferably, in compounds of this type, X, $L^1$, and $L^2$ are taken together to be cyclopentadienyl or indenyl, each optionally substituted with vinyl, $C_1$-$C_{10}$ alkyl, $C_5$-$C_{20}$ aryl, $C_1$-$C_{10}$ carboxylate, $C_2$-$C_{10}$ alkoxycarbonyl, $C_1$-$C_{10}$ alkoxy, or $C_5$-$C_{20}$ aryloxy, each optionally substituted with $C_1$-$C_6$ alkyl, halide, $C_1$-$C_6$ alkoxy, or with a phenyl group optionally substituted with halide, $C_1$-$C_6$ alkyl, or $C_1$-$C_6$ alkoxy. Most preferably, X, $L^1$, and $L^2$ may be taken together to be cyclopentadienyl, optionally substituted with vinyl, hydrogen, methyl, or phenyl. Tetradentate ligands include, but are not limited to O$_2$C(CH$_2$)$_2$P(Ph)(CH$_2$)$_2$P(Ph)(CH$_2$)$_2$CO$_2$, phthalocyanines, and porphyrins.

A fifth group of cyclic olefin metathesis catalysts, commonly called "Grubbs-Hoveyda" catalysts, may be described by the Formula (VII):

wherein: M is a Group 8 transition metal, particularly Ru or Os, or, more particularly, Ru; $X^1$, $X^2$, and $L^1$ are as previously defined herein for the first and second groups of catalysts; Y is a heteroatom selected from N, O, S, and P; preferably Y is O or N; $R^5$, $R^6$, $R^7$, and $R^8$ are each, independently, selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, borate, or -A-Fn, wherein "A" and Fn have been defined above; and any combination of Y, Z, $R^5$, $R^6$, $R^7$, and $R^8$ can be linked to form one or more cyclic groups; n is 0, 1, or 2, such that n is 1 for the divalent heteroatoms O or S, and n is 2 for the trivalent heteroatoms N or P; and Z is a group selected from hydrogen, alkyl, aryl, functionalized alkyl, functionalized aryl where the functional group(s) may independently be one or more or the following: alkoxy, aryloxy, halogen, carboxylic acid, ketone, aldehyde, nitrate, cyano, isocyanate, hydroxyl, ester, ether, amine, imine, amide, trifluoroacetamide, sulfide, disulfide, carbamate, silane, siloxane, phosphine, phosphate, or borate; methyl, isopropyl, sec-butyl, t-butyl, neopentyl, benzyl, phenyl, and trimethylsilyl; and wherein any combination or combinations of $X^1$, $X^2$, $L^1$, Y, Z, $R^5$, $R^6$, $R^7$, and $R^8$ may optionally be linked to a support. Additionally, $R^5$, $R^6$, $R^7$, $R^8$, and Z may independently be thioisocyanate, cyanato, or thiocyanato.

Examples of complexes comprising Grubbs-Hoveyda ligands suitable in the invention include:

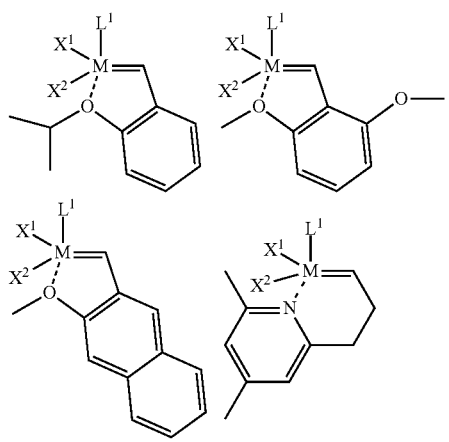

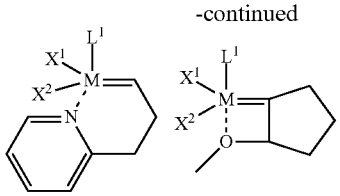

wherein: $L^1$, $X^1$, $X^2$, and M are as described for any of the other groups of catalysts. Suitable chelating carbenes and carbene precursors are further described by Pederson et al. (U.S. Pat. Nos. 7,026,495 and 6,620,955), and Hoveyda et al. (U.S. Pat. No. 6,921,735 and International Patent Application Publication No. WO0214376).

Other useful complexes include structures wherein $L^2$ and $R^2$ according to Formulae (I), (III), or (V) are linked, such as styrenic compounds that also include a functional group for attachment to a support, as described in International Patent Application WO2011069134.

Cyclic olefin metathesis catalysts containing a cationic substituent described in International Patent Application WO2005121158, may also be used in the invention disclosed herein.

Additionally, another group of cyclic olefin metathesis catalysts that may be used in the invention disclosed herein, is a Group 8 transition metal complex represented by the structure of Formula (XIII):

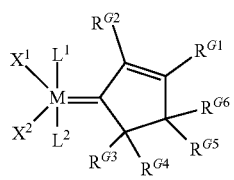

Formula (XIII)

wherein: M is a Group 8 transition metal, particularly Ruthenium or Osmium, or more particularly, Ruthenium; $X^1$, $X^2$, $L^1$, and $L^2$ are as defined for the first and second groups of catalysts defined above; and $R^{G1}$, $R^{G2}$, $R^{G3}$, $R^{G4}$, $R^{G5}$, and $R^{G6}$ are each independently selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, thioisocyanate, cyanato, thiocyanato, hydroxyl, ester, ether, thioether, amine, alkylamine, imine, amide, halogen-substituted amide, trifluoroamide, sulfide, disulfide, sulfonate, carbamate, silane, siloxane, phosphine, phosphate, borate, or -A-Fn, wherein "A" is a divalent hydrocarbon moiety selected from alkylene and arylalkylene, wherein the alkyl portion of the alkylene and arylalkylene groups can be linear or branched, saturated or unsaturated, cyclic or acyclic, and substituted or unsubstituted, wherein the aryl portion of the arylalkylene can be substituted or unsubstituted, and wherein hetero atoms and/or functional groups may be present in either the aryl or the alkyl portions of the alkylene and arylalkylene groups, and Fn is a functional group, or any one or more of the $R^{G1}$, $R^{G2}$, $R^{G3}$, $R^{G4}$, $R^{G5}$, and $R^{G6}$ may be linked together to form a cyclic group, or any one or more of the $R^{G1}$, $R^{G2}$, $R^{G3}$, $R^{G4}$, $R^{G5}$, and $R^{G6}$ may be attached to a support.

Additionally, one preferred embodiment of the Group 8 transition metal complex of Formula (XIII) is a Group 8 transition metal complex represented by the structure of Formula (XIV):

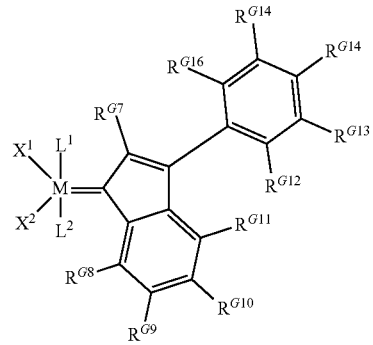

Formula (XIV)

wherein: M, $X^1$, $X^2$, $L^1$, and $L^2$ are as defined above for Group 8 transition metal complex of Formula (XIII); and $R^{G7}$, $R^{G8}$, $R^{G9}$, $R^{G10}$, $R^{G11}$, $R^{G12}$, $R^{G13}$, $R^{G14}$, $R^{G15}$, and $R^{G16}$ are as defined above for $R^{G1}$, $R^{G2}$, $R^{G3}$, $R^{G4}$, $R^{G5}$, and $R^{G6}$ for Group 8 transition metal complex represented by the structure of Formula (XIII) or any one or more of the $R^{G7}$, $R^{G8}$, $R^{G9}$, $R^{G10}$, $R^{G11}$, $R^{G12}$, $R^{G13}$, $R^{G14}$, $R^{G15}$, and $R^{G16}$ may be linked together to form a cyclic group, or any one or more of the $R^{G7}$, $R^{G8}$, $R^{G9}$, $R^{G10}$, $R^{G11}$, $R^{G12}$, $R^{G13}$, $R^{G14}$, $R^{G15}$, and $R^{G16}$ may be attached to a support.

Additionally, another preferred embodiment of the Group 8 transition metal complex represented by the structure of Formula (XIII) is a Group 8 transition metal complex represented by the structure of Formula (XV):

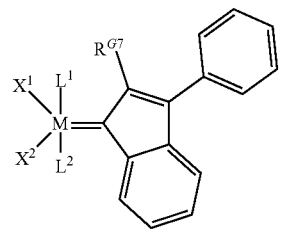

Formula (XV)

wherein: M, $X^1$, $X^2$, $L^1$, and $L^2$ are as defined above for Group 8 transition metal complex represented by the structure of Formula (XIII).

In addition, other examples of catalysts that may be used with the present invention are located in the following disclosures: U.S. Pat. Nos. 7,687,635; 7,671,224; 6,284,852; 6,486,279; and 5,977,393; International Patent Application Publication No. WO2010/037550; and U.S. patent application Ser. Nos. 12/303,615; 10/590,380; 11/465,651 (Publication No.: US 2007/0043188); and Ser. No. 11/465,651 (Publication No.: US 2008/0293905 Corrected Publication); and European Patent Nos. EP1757613B1 and EP1577282B1.

In the foregoing molecular structures and formulae, Ph represents phenyl, Cy represents cyclohexyl, Cp represents cyclopentyl, Me represents methyl, Bu represents n-butyl, t-Bu represents tert-butyl, i-Pr represents isopropyl, py represents pyridine (coordinated through the N atom), Mes represents mesityl (i.e., 2,4,6-trimethylphenyl), DiPP and DIPP represent 2,6-diisopropylphenyl, and MiPP represents 2-isopropylphenyl.

Non-limiting examples of cyclic olefin metathesis catalysts that may be used to prepare ROMP compositions disclosed herein, include the following, some of which for convenience are identified throughout this disclosure by reference to their molecular weight:

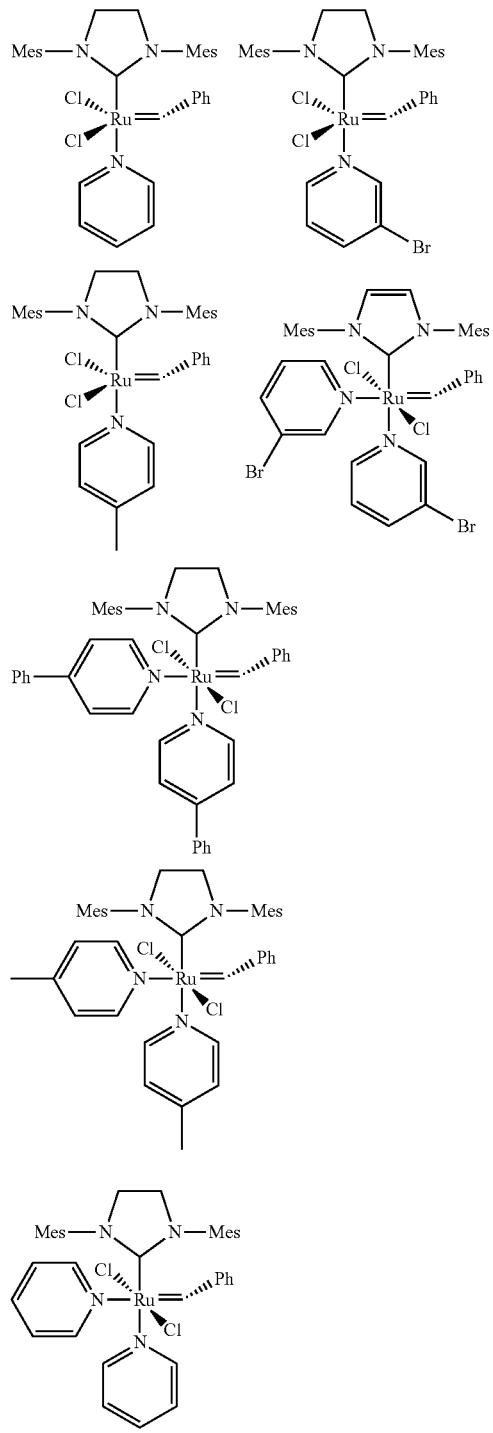

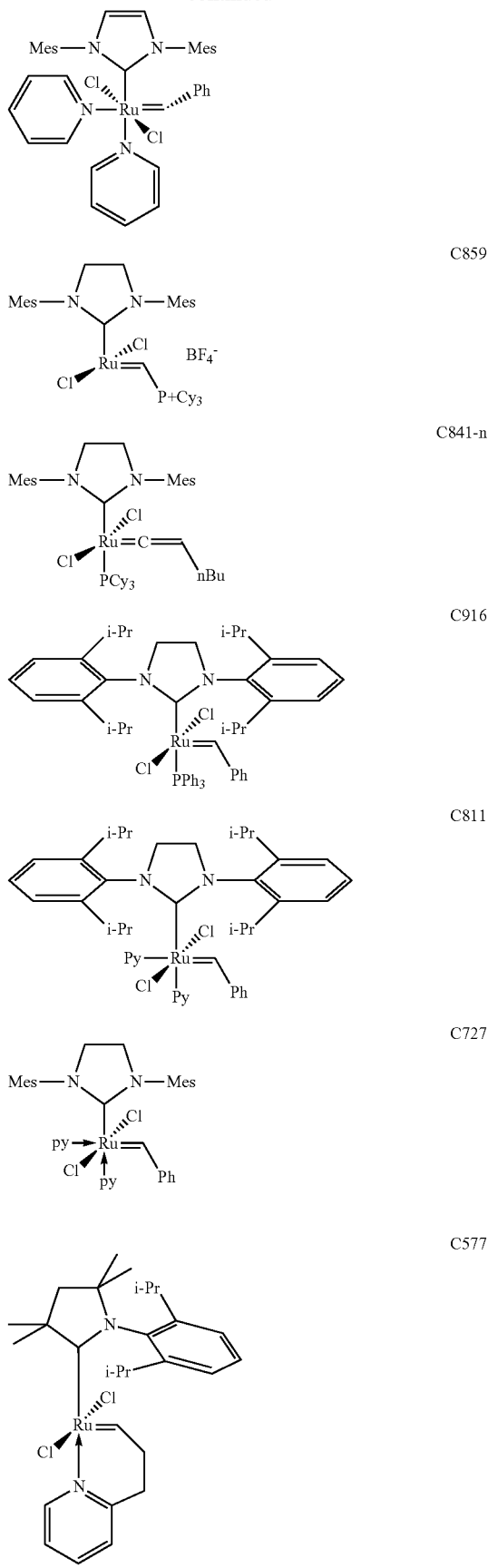

-continued
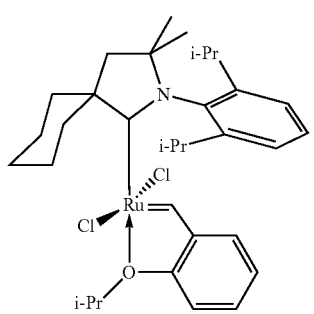
C646
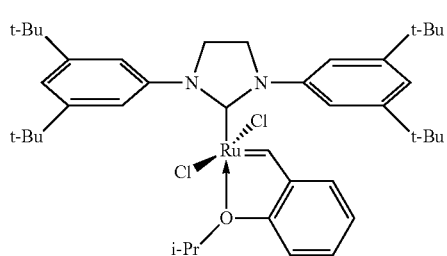
C767-m
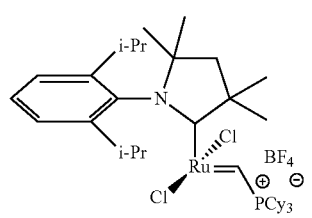
C838
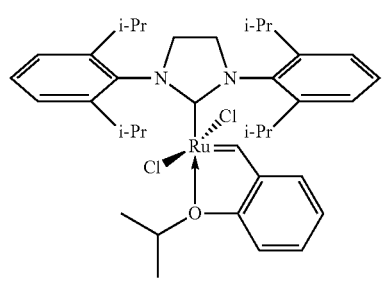
C711
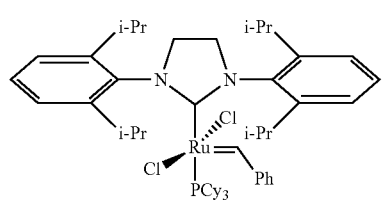
C933
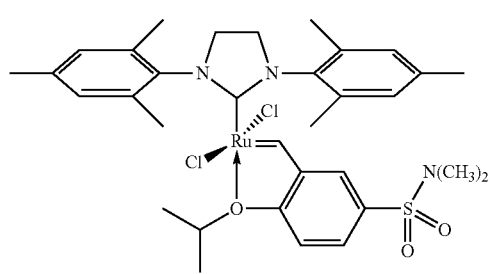
-continued
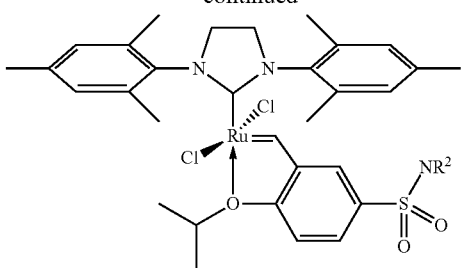
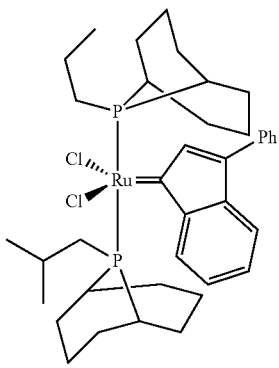
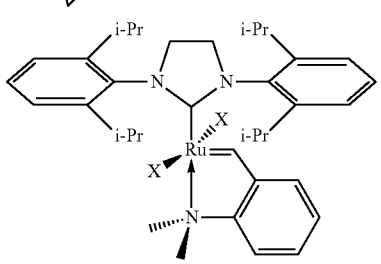
C697 (X = Cl)
C785 (X = Br)
C879 (X = I)
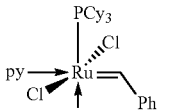
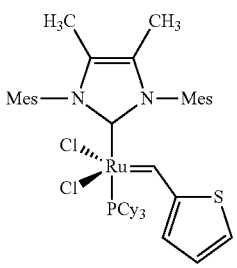
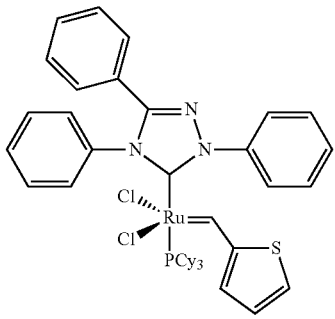
C701

-continued
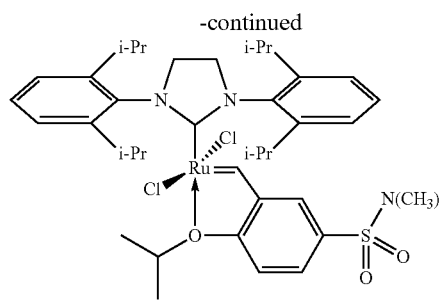
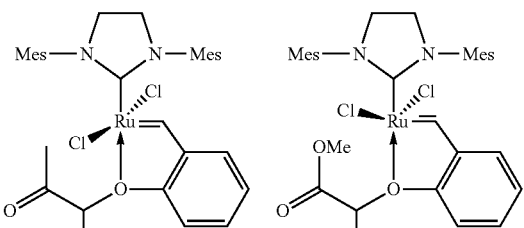
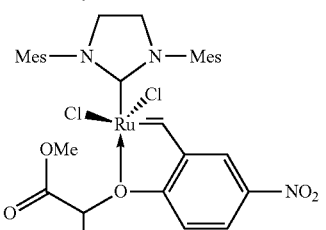
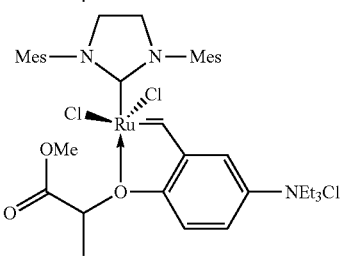
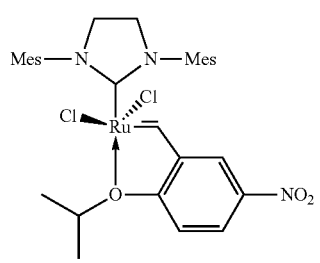
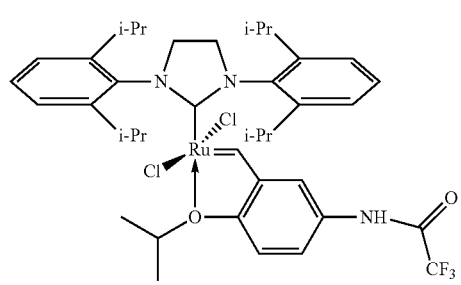
-continued
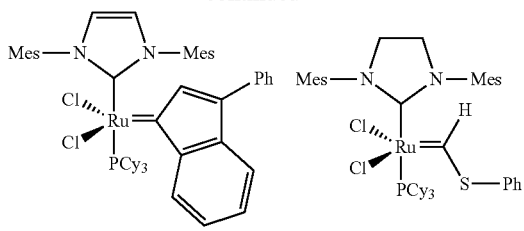
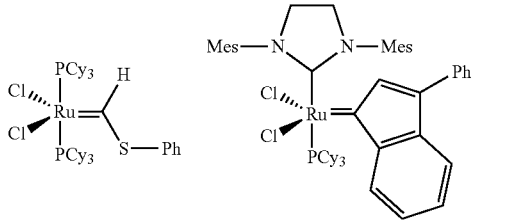
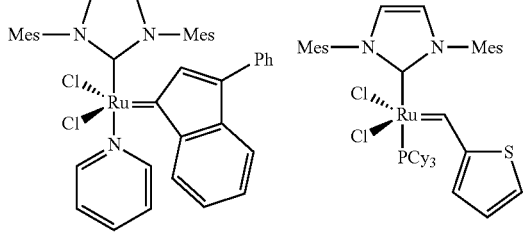
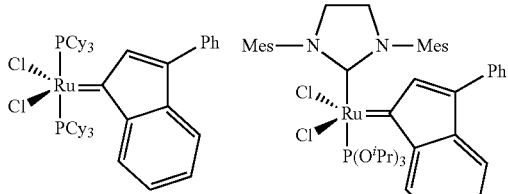
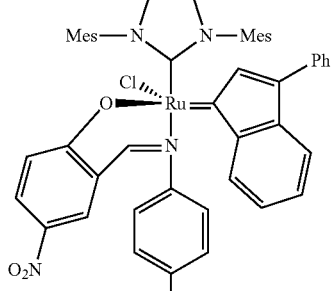
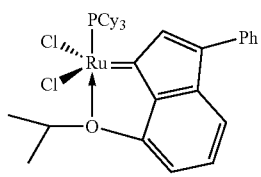
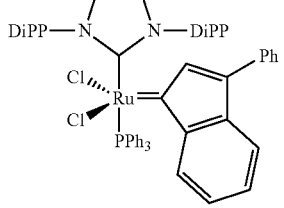

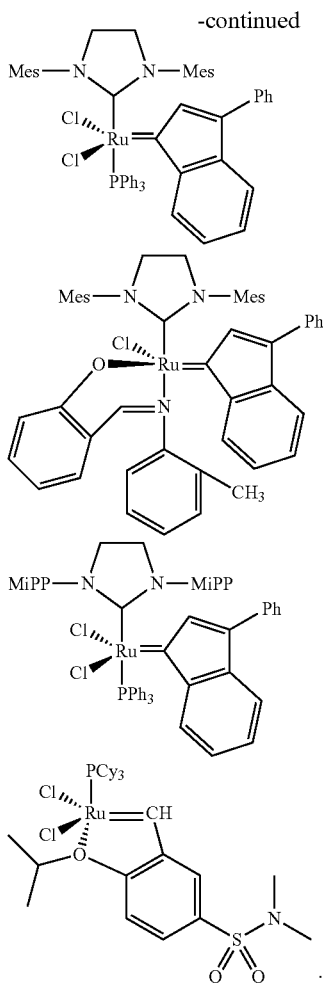

Further non-limiting examples of cyclic olefin metathesis catalysts useful to prepare ROMP compositions disclosed herein, include the following: Ruthenium (II) dichloro (3-methyl-2-butenylidene) bis(tricyclopentylphosphine) (C716); Ruthenium (II) dichloro (3-methyl-2-butenylidene) bis(tricyclohexylphosphine) (C801); Ruthenium (II) dichloro(phenylmethylene) bis(tricyclohexylphosphine) (C823); Ruthenium (II) (1,3-bis-(2,4,6-trimethylphenyl)-2-imidazolidinylidene) dichloro (phenylmethylene) (triphenylphosphine) (C830); Ruthenium (II) dichloro (phenylvinylidene) bis(tricyclohexyl phosphine) (C835); Ruthenium (II) dichloro (tricyclohexylphosphine) (o-isopropoxyphenylmethylene) (C601); Ruthenium (II) (1,3-bis-(2,4,6-trimethylphenyl)-2-imidazolidinylidene) dichloro (phenylmethylene) bis(3-bromopyridine) (C884); [1,3-bis-(2,4,6-trimethylphenyl)-2-imidazolidinylidene]dichloro(o-isopropoxy phenylmethylene)Ruthenium(II) (C627); [1,3-bis-(2,4,6-trimethylphenyl)-2-imidazolidinylidene] dichloro (benzylidene) (triphenylphosphine) Ruthenium(II) (C831); [1,3-bis-(2,4,6-trimethylphenyl)-2-imidazolidinylidene] dichloro (benzylidene) (methyldiphenylphosphine) Ruthenium(II) (C769); [1,3-bis-(2,4,6-trimethylphenyl)-2-imidazolidinylidene]dichloro (benzylidene) (tricyclohexylphosphine) Ruthenium(II) (C848); [1,3-bis-(2,4,6-trimethylphenyl)-2-imidazolidinylidene] dichloro(benzylidene) (diethylphenyl phosphine)Ruthenium(II) (C735); [1,3-bis-(2,4,6-trimethylphenyl)-2-imidazolidinylidene]dichloro (benzylidene) (tri-n-butylphosphine)Ruthenium(II) (C771); [1,3-bis-(2,4,6-trimethylphenyl)-2-imidazolidinylidene]dichloro(3-methyl-2-butenylidene)(triphenylphosphine)Ruthenium(II) (C809); [1,3-bis-(2,4,6-trimethylphenyl)-2-imidazolidinylidene]dichloro(3-methyl-2-butenylidene) (methyl diphenyl phosphine)Ruthenium(II) (C747); [1,3-bis-(2,4,6-trimethylphenyl)-2-imidazolidinylidene]dichloro(3-methyl-2-butenylidene) (tricyclohexylphosphine) Ruthenium(II) (C827); [1,3-bis-(2,4,6-trimethylphenyl)-2-imidazolidinylidene] dichloro(3-methyl-2-butenylidene)(diethyl phenylphosphine)Ruthenium(II) (C713); [1,3-bis-(2,4,6-trimethylphenyl)-2-imidazolidinylidene]dichloro (3-methyl-2-butenylidene) (tri-n-butylphosphine)Ruthenium(II) (C749); [1,3-bis-(2,4,6-trimethylphenyl)-2-imidazolidinylidene] dichloro(phenylindenylidene)(triphenylphosphine) Ruthenium(II) ($C_{931}$); [1,3-bis-(2,4,6-trimethylphenyl)-2-imidazolidinylidene] dichloro (phenylindenylidene) (methylphenylphosphine) Ruthenium(II) (C869); [1,3-bis-(2,4,6-trimethylphenyl)-2-imidazolidinylidene] dichloro (phenylindenylidene) (tricyclohexylphosphine) Ruthenium(II) (C949); [1,3-bis-(2,4,6-trimethylphenyl)-2-imidazolidinylidene]dichloro (phenylindenylidene)(diethylphenyl phosphine) Ruthenium(II) (C835); and [1,3-bis-(2,4,6-trimethylphenyl)-2-imidazolidinylidene] dichloro (phenylindenylidene) (tri-n-butylphosphine) Ruthenium(II) (C871).

In general, the cyclic olefin metathesis catalysts used herein can be prepared by several different methods, such as those described by Schwab et al., *J. Am. Chem. Soc.* (1996), 118, 100-110, Scholl et al., *Org. Lett.* (1999), 6, 953-956, Sanford et al., *J. Am. Chem. Soc.* (2001), 123, 749-750, U.S. Pat. Nos. 5,312,940, and 5,342,909. Also see U.S. Patent Application Publication No. 2003/0055262 to Grubbs et al., International Patent Application Publication No. WO 02/079208, and U.S. Pat. No. 6,613,910 to Grubbs et al. Preferred synthetic methods are described in International Patent Application Publication No. WO03/11455A1 to Grubbs et al.

Examples of preferred cyclic olefin metathesis catalysts are Group 8 transition metal complexes represented by the structure of Formula (I) commonly called "First Generation Grubbs" catalysts, Formula (III) commonly called "Second Generation Grubbs" catalysts, or Formula (VII) commonly called "Grubbs-Hoveyda" catalysts.

Examples of preferred cyclic olefin metathesis catalysts are represented by the structure of Formula (I) wherein: M is a Group 8 transition metal; $L^1$, $L^2$, and $L^3$ are neutral electron donor ligands; n is 0 or 1; m is 0, 1, or 2; k is 0 or 1; $X^1$ and $X^2$ are anionic ligands; $R^1$ and $R^2$ are independently selected from hydrogen, hydrocarbyl, substituted hydrocarbyl, heteroatom-containing hydrocarbyl, substituted heteroatom-containing hydrocarbyl, and functional groups, wherein any two or more of $X^1$, $X^2$, $L^1$, $L^2$, $L^3$, $R^1$, and $R^2$ can be taken together to form one or more cyclic groups, and further wherein any one or more of $X^1$, $X^2$, $L^1$, $L^2$, $L^3$, $R^1$, and $R^2$ may optionally be attached to a support.

Examples of preferred cyclic olefin metathesis catalysts are represented by the structure of Formula (VII) wherein: M is a Group 8 transition metal; $L^1$ is a neutral electron donor ligand; $X^1$ and $X^2$ are anionic ligands; Y is a heteroatom selected from O or N; $R^5$, $R^6$, $R^7$, and $R^8$ are independently selected from hydrogen, hydrocarbyl, substituted hydrocarbyl, heteroatom-containing hydrocarbyl, substituted heteroatom-containing hydrocarbyl, and functional groups; n is 0, 1, or 2; and Z is selected from hydrogen, hydrocarbyl, substituted hydrocarbyl, heteroatom-containing hydrocarbyl, substituted heteroatom-containing hydrocarbyl, and functional groups, wherein any combination of Y, Z, $R^5$, $R^6$, $R^7$, and $R^8$ can be linked to form one or more cyclic groups, and further wherein any combination of $X^1$, $X^2$, $L^1$, Y, Z, $R^5$, $R^6$, $R^7$, and $R^8$ may optionally be attached to a support.

Examples of preferred cyclic olefin metathesis catalysts are represented by the structure of Formula (I) wherein: M is Ruthenium; n is 0; m is 0; k is 1; $L^1$ and $L^2$ are trisubstituted phosphines independently selected from the group consisting of tri-n-butylphosphine (Pn-Bu$_3$), tricyclopentylphosphine (PCp$_3$), tricyclohexylphosphine (PCy$_3$), triisopropylphosphine (P-i-Pr$_3$), triphenylphosphine (PPh$_3$), methyldiphenylphosphine (PMePh$_2$), dimethylphenylphosphine (PMe$_2$Ph), and diethylphenylphosphine (PEt$_2$Ph); or $L^1$ is an N-heterocyclic carbene selected from the group consisting of 1,3-bis(2,4,6-trimethylphenyl)-2-imidazolidinylidene, 1,3-bis(2,4,6-trimethylphenyl)imidazol-2-ylidene, 1,3-bis(2,6-di-isopropylphenyl)-2-imidazolidinylidene, and 1,3-bis(2,6-di-isopropylphenyl)imidazol-2-ylidene and $L^2$ is a trisubstituted phosphine selected from the group consisting of tri-n-butylphosphine (Pn-Bu$_3$), tricyclopentylphosphine (PCp$_3$), tricyclohexylphosphine (PCy$_3$), triisopropylphosphine (P-i-Pr$_3$), triphenylphosphine (PPh$_3$), methyldiphenylphosphine (PMePh$_2$), dimethylphenylphosphine (PMe$_2$Ph), and diethylphenylphosphine (PEt$_2$Ph); $X^1$ and $X^2$ are chloride; $R^1$ is hydrogen and $R^2$ is phenyl, —CH=C(CH$_3$)$_2$, or thienyl; or $R^1$ and $R^2$ are taken together to form phenylindenylidene.

Examples of preferred cyclic olefin metathesis catalysts are represented by the structure of Formula (VII) wherein: M is Ruthenium; $L^1$ is a trisubstituted phosphine selected from the group consisting of tri-n-butylphosphine (Pn-Bu$_3$), tricyclopentylphosphine (PCp$_3$), tricyclohexylphosphine (PCy$_3$), triisopropylphosphine (P-i-Pr$_3$), triphenylphosphine (PPh$_3$), methyldiphenylphosphine (PMePh$_2$), dimethylphenylphosphine (PMe$_2$Ph), and diethylphenylphosphine (PEt$_2$Ph); or $L^1$ is an N-heterocyclic carbene selected from the group consisting of 1,3-bis(2,4,6-trimethylphenyl)-2-imidazolidinylidene, 1,3-bis(2,4,6-trimethylphenyl)imidazol-2-ylidene, 1,3-bis(2,6-di-isopropylphenyl)-2-imidazolidinylidene, and 1,3-bis(2,6-di-isopropylphenyl)imidazol-2-ylidene; $X^1$ and $X^2$ are chloride; Y is oxygen; $R^5$, $R^6$, $R^7$, and $R^8$ are each hydrogen; n is 1; and Z is isopropyl.

Examples of preferred cyclic olefin metathesis catalysts are represented by the structure of Formula (I) wherein: M is Ruthenium; n is 0; m is 0; k is 1; $L^2$ is a trisubstituted phosphine independently selected from the group consisting of tri-n-butylphosphine (Pn-Bu$_3$), tricyclopentylphosphine (PCp$_3$), tricyclohexylphosphine (PCy$_3$), triisopropylphosphine (P-i-Pr$_3$), triphenylphosphine (PPh$_3$), methyldiphenylphosphine (PMePh$_2$), dimethylphenylphosphine (PMe$_2$Ph), and diethylphenylphosphine (PEt$_2$Ph); $L^1$ is an N-heterocyclic carbene selected from the group consisting of 1,3-bis(2,4,6-trimethylphenyl)-2-imidazolidinylidene, and 1,3-bis(2,6-di-isopropylphenyl)-2-imidazolidinylidene; $X^1$ and $X^2$ are chloride; $R^1$ is hydrogen and $R^2$ is phenyl, —CH=C(CH$_3$)$_2$, or thienyl; or $R^1$ and $R^2$ are taken together to form phenylindenylidene.

Examples of preferred cyclic olefin metathesis catalysts are represented by the structure of Formula (I) wherein: M is Ruthenium; n is 0; m is 0; k is 1; $L^2$ is a trisubstituted phosphine independently selected from the group consisting of tri-n-butylphosphine (Pn-Bu$_3$), tricyclopentylphosphine (PCp$_3$), tricyclohexylphosphine (PCy$_3$), triisopropylphosphine (P-i-Pr$_3$), triphenylphosphine (PPh$_3$), methyldiphenylphosphine (PMePh$_2$), dimethylphenylphosphine (PMe$_2$Ph), and diethylphenylphosphine (PEt$_2$Ph); $L^1$ is an N-heterocyclic carbene selected from the group consisting of 1,3-bis(2,4,6-trimethylphenyl)-2-imidazolidinylidene, and 1,3-bis(2,6-di-isopropylphenyl)-2-imidazolidinylidene; $X^1$ and $X^2$ are chloride; $R^1$ is hydrogen and $R^2$ is phenyl or —CH=C(CH$_3$)$_2$; or $R^1$ and $R^2$ are taken together to form phenylindenylidene.

Examples of preferred cyclic olefin metathesis catalysts are represented by the structure of Formula (I) wherein: M is Ruthenium; n is 0; m is 0; k is 1; $L^2$ is a trisubstituted phosphine independently selected from the group consisting of tri-n-butylphosphine (Pn-Bu$_3$), tricyclopentylphosphine (PCp$_3$), tricyclohexylphosphine (PCy$_3$), triisopropylphosphine (P-i-Pr$_3$), triphenylphosphine (PPh$_3$), methyldiphenylphosphine (PMePh$_2$), dimethylphenylphosphine (PMe$_2$Ph), and diethylphenylphosphine (PEt$_2$Ph); $L^1$ is an N-heterocyclic carbene 1,3-bis(2,4,6-trimethylphenyl)-2-imidazolidinylidene; $X^1$ and $X^2$ are chloride; $R^1$ is hydrogen and $R^2$ is phenyl or —CH=C(CH$_3$)$_2$; or $R^1$ and $R^2$ are taken together to form phenylindenylidene.

Examples of preferred cyclic olefin metathesis catalysts are represented by the structure of Formula (I) wherein: M is Ruthenium; n is 0; m is 0; k is 1; $L^2$ is a trisubstituted phosphine independently selected from the group consisting of tri-n-butylphosphine (Pn-Bu$_3$), tricyclopentylphosphine (PCp$_3$), tricyclohexylphosphine (PCy$_3$), triisopropylphosphine (P-i-Pr$_3$), triphenylphosphine (PPh$_3$), methyldiphenylphosphine (PMePh$_2$), dimethylphenylphosphine (PMe$_2$Ph), and diethylphenylphosphine (PEt$_2$Ph); $L^1$ is an N-heterocyclic carbene selected from the group consisting of 1,3-bis(2,4,6-trimethylphenyl)-2-imidazolidinylidene, and 1,3-bis(2,6-di-isopropylphenyl)-2-imidazolidinylidene; $X^1$ and $X^2$ are chloride; $R^1$ is hydrogen and $R^2$ is phenyl or —CH=C(CH$_3$)$_2$.

Examples of preferred cyclic olefin metathesis catalysts are represented by the structure of Formula (I) wherein: M is Ruthenium; n is 0; m is 0; k is 1; $L^2$ is a trisubstituted phosphine independently selected from the group consisting of tri-n-butylphosphine (Pn-Bu$_3$), tricyclopentylphosphine (PCp$_3$), tricyclohexylphosphine (PCy$_3$), triisopropylphosphine (P-i-Pr$_3$), triphenylphosphine (PPh$_3$), methyldiphenylphosphine (PMePh$_2$), dimethylphenylphosphine (PMe$_2$Ph), and diethylphenylphosphine (PEt$_2$Ph); $L^1$ is an N-heterocyclic carbene 1,3-bis(2,4,6-trimethylphenyl)-2-imidazolidinylidene; $X^1$ and $X^2$ are chloride; $R^1$ is hydrogen and $R^2$ is phenyl or —CH=C(CH$_3$)$_2$.

Examples of preferred cyclic olefin metathesis catalysts are represented by the structure of Formula (VII) wherein: M is Ruthenium; $L^1$ is an N-heterocyclic carbene selected from the group consisting of 1,3-bis(2,4,6-trimethylphenyl)-2-imidazolidinylidene, 1,3-bis(2,4,6-trimethylphenyl)imidazol-2-ylidene, 1,3-bis(2,6-di-isopropylphenyl)-2-imidazolidinylidene, and 1,3-bis(2,6-di-isopropylphenyl)imidazol-2-ylidene; $X^1$ and $X^2$ are chloride; Y is oxygen; $R^5$, $R^6$, $R^7$, and $R^8$ are each hydrogen; n is 1; and Z is isopropyl.

Examples of preferred cyclic olefin metathesis catalysts are represented by the structure of Formula (VII) wherein:

M is Ruthenium; $L^1$ is an N-heterocyclic carbene selected from the group consisting of 1,3-bis(2,4,6-trimethylphenyl)-2-imidazolidinylidene, and 1,3-bis(2,6-di-isopropylphenyl)-2-imidazolidinylidene; $X^1$ and $X^2$ are chloride; Y is oxygen; $R^5$, $R^6$, $R^7$, and $R^8$ are each hydrogen; n is 1; and Z is isopropyl.

Suitable supports for any of the metal carbene olefin metathesis catalysts described herein may be of synthetic, semi-synthetic, or naturally occurring materials, which may be organic or inorganic, e.g., polymeric, ceramic, or metallic. Attachment to the support will generally, although not necessarily, be covalent, and the covalent linkage may be direct or indirect. Indirect covalent linkages are typically, though not necessarily, through a functional group on a support surface. Ionic attachments are also suitable, including combinations of one or more anionic groups on the metal complexes coupled with supports containing cationic groups, or combinations of one or more cationic groups on the metal complexes coupled with supports containing anionic groups.

When utilized, suitable supports may be selected from silicas, silicates, aluminas, aluminum oxides, silica-aluminas, aluminosilicates, zeolites, titanias, titanium dioxide, magnetite, magnesium oxides, boron oxides, clays, zirconias, zirconium dioxide, carbon, polymers, cellulose, cellulosic polymers amylose, amylosic polymers, or a combination thereof. The support preferably comprises silica, a silicate, or a combination thereof.

In certain embodiments, it is also possible to use a support that has been treated to include functional groups, inert moieties, and/or excess ligands. Any of the functional groups described herein are suitable for incorporation on the support, and may be generally accomplished through techniques known in the art. Inert moieties may also be incorporated on the support to generally reduce the available attachment sites on the support, e.g., in order to control the placement, or amount, of a complex linked to the support.

At least one metal carbene olefin metathesis catalyst may be utilized in olefin metathesis reactions according to techniques known in the art. The at least one metal carbene olefin metathesis catalyst are typically utilized as a solid, a solution, or as a suspension. When the at least one metal carbene olefin metathesis catalyst is utilized as a suspension, the at least one metal carbene olefin metathesis catalyst is suspended in a dispersing carrier, such as mineral oil, paraffin oil, soybean oil, tri-isopropylbenzene, or any hydrophobic liquid which has a sufficiently high viscosity so as to permit effective dispersion of the catalyst(s), and which is sufficiently inert and which has a sufficiently high boiling point so that is does not act as a low-boiling impurity in the olefin metathesis reaction. It will be appreciated that the amount of catalyst that is used (i.e., the "catalyst loading") in the reaction is dependent upon a variety of factors, such as the identity of the reactants and the reaction conditions that are employed. It is therefore understood that catalyst loading may be optimally and independently chosen for each reaction. In general, however, the catalyst will be present in an amount that ranges from a low of about 0.1 ppm, 1 ppm, or 5 ppm, to a high of about 10 ppm, 15 ppm, 25 ppm, 50 ppm, 100 ppm, 200 ppm, 500 ppm, or 1000 ppm relative to the amount of an olefinic substrate.

The catalyst will generally be present in an amount that ranges from a low of about 0.00001 mol %, 0.0001 mol %, or 0.0005 mol %, to a high of about 0.001 mol %, 0.0015 mol %, 0.0025 mol %, 0.005 mol %, 0.01 mol %, 0.02 mol %, 0.05 mol %, or 0.1 mol % relative to the olefinic substrate.

When expressed as the molar ratio of monomer to catalyst, the catalyst (the "monomer to catalyst ratio"), loading will generally be present in an amount that ranges from a low of about 10,000,000:1, 1,000,000:1, or 200,00:1, to a high of about 100,000:1 66,667:1, 40,000:1, 20,000:1, 10,000:1, 5,000:1, or 1,000:1.

Hydrogenation Catalysts

Hydrogenation catalysts which may be used in the invention include, but are not limited, to: Metal Oxides, such as Platinum, Ruthenium, rhodium, and zinc oxides; Rhodium catalysts, such as: Tris(triphenylphosphine)halorhodium(I) catalysts, Water-soluble complexes of tertiary phosphines and Rhodium(I) as homogeneous catalysts, covalently immobilized ultrafine rhodium particles, Polymer-supported palladium and rhodium hydrogenation catalysts, Rhodium (I) acetylacetonato complexes; or Ruthenium catalysts, such as: Hydrido(phosphine)ruthenates, Ruthenium pillared layered clay, Water-Soluble Ruthenium(II)—N-Heterocyclic Carbene Complexes, Ruthenium(II) catalyst [{RuCl(μ-Cl)(η$^6$-C$_6$Me$_6$)}$_2$]; Pt and Pd catalysts, such as: acidic aq. solns. on Pt and Pd—Ag, Palladium chloride and sodium borohydride, polymer-bound palladium (II) complexes, palladium complexes anchored in montmorillonite, Polymer-supported palladium and platinum species, platinum colloids, Pd(0) Nanoparticle, Peptide-Templated Pd and Pt Nanomaterials; Nickel catalysts, such as: Raney nickel, nickel boride, Aluminum phosphate (AlPO$_4$)-supported nickel catalysts, Nickel(0) Nanoparticles; Iridium catalysts, such as: Cp*IrIII (H$_2$O)$_3$]$^{2+}$ (Cp*=η$^5$-C$_5$Me$_5$) catalysts, Iridium(III) pentamethylcyclo pentadienyl catalyst supported by 6,6'-dihydroxy-2,2'-bipyridine, [Ir(NHC)(h4-cod)(L)]Xn complexes [4-9, 11; NHC=1-butyl-3-methyl-2-imidazolylidene (bmim), 1-ethyl-3-methyl-2-imidazolylidene (emim), L=Cl—, H$_2$O, (3-NaO$_3$SC$_6$H$_4$)PPh$_2$ (mtppms-Na), (3-NaO$_3$SC$_6$H$_4$)$_3$P (mtppts-Na$_3$), 1,3,5-triaza-7-phosphaadamantane (PTA); X=Cl, BF$_4$, n=0, 1]; Silver catalysts.

Catalysts Used During the Tandem Amination-Reduction Process

Catalysts which may be used in the invention during the tandem amination-reduction process are Ruthenium pincer complexes represented by the structure of Formula 4, wherein:

$L^4$ and $L^5$ are each independently selected from the group consisting of phosphine (PR$^a$R$^b$), amine (NR$^a$R$^b$), imine, sulfide (SR$^d$), thiol (SH), sulfoxide (S(=O)R$^d$), heteroaryl containing at least one heteroatom selected from nitrogen and sulfur; arsine (AsR$^a$R$^b$), stibine (SbR$^a$R$^b$), and an N-heterocyclic carbene represented by the structures:

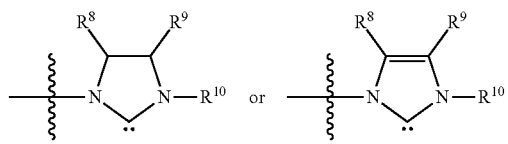

$L^6$ is a mono-dentate two-electron donor, such as CO, PR$^a$R$^b$R$^c$, NO$^+$, AsR$^a$R$^b$R$^c$, SbR$^a$R$^b$R$^c$, SR$^a$R$^b$, nitrile (R$^d$CN), isonitrile (R$^d$NC), N$_2$, PF$_3$, CS, heteroaryl (e.g., pyridine, thiophene), tetrahydrothiophene, and N-heterocyclic carbene;

$R^6$ and $R^7$ are either each hydrogen or together with the carbons to which they are attached represent a phenyl ring which is fused to the quinolinyl moiety represented by the structure of Formula 4 so as to form an acridinyl moiety;

$R^a$, $R^b$, $R^c$, $R^d$, $R^8$, $R^9$, and $R^{10}$ are each independently alkyl, cycloalkyl, aryl, heterocyclyl, heteroaryl, alkylcycloalkyl, alkylaryl, alkylheterocyclyl, or alkylheteroaryl;

$Y_a$ is a monoanionic ligand, such as halogen, —$OCOR^d$, —$OCOCF_3$, —$OSO_2R^d$, —$OSO_2CF_3$, —CN, —OH, —$OR^d$, and —$NR^d_2$; or a neutral solvent molecule, such as $NH_3$, $NR_3$, and $R^d_2NSO_2R^d$, wherein $R^d$ is defined above; and when $Y_a$ is neutral, the whole molecule carries a positive charge; and $X_a$ represents one, two, three, four, five, six, or seven substituents positioned at any carbon atom on the acridinyl moiety (in the case where $R^6$ and $R^7$ together with the carbons to which they are attached represent a phenyl ring which is fused to the quinolinyl moiety represented by the structure of Formula 4); or one, two, three, four, or five substituents positioned on any carbon atom on the quinolinyl moiety (in the case where $R^6$ and $R^7$ are each hydrogen), and is selected from the group consisting of hydrogen, alkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support (e.g., silica), and a polymeric moiety (e.g., polystyrene).

The Ruthenium pincer complexes represented by the structure of Formula 4 are sometimes called Milstein catalysts as described by Milstein et al., *Angew. Chem. Int. Ed.* (2008), 47, 8661-8664 (and Supporting Information), and International Patent Application Publication No. WO 2010/018570.

In one embodiment, the Ruthenium pincer complex represented by the structure of Formula 4 is [RuHCl(A-iPr-PNP)(CO)], Chlorocarbonylhydrido[4,5-bis-(di-i-propylphosphinomethyl)acridine] Ruthenium (II).

In another embodiment, the Ruthenium pincer complex represented by the structure of Formula 4 is [RuHCl(A-Cy-PNP)(CO)], Chlorocarbonylhydrido[4,5-bis-(di-cyclohexylphosphinomethyl)acridine] Ruthenium (II).

Olefinic Substrates

Olefinic substrates that may be used in the invention disclosed herein are represented by the structure of Formula 2, wherein: R is —H, optionally substituted $C_1$-$C_{12}$ alkyl, optionally substituted $C_6$-$C_{10}$ aryl, optionally substituted heterocycle or optionally substituted $C_5$-$C_{10}$ cycloalkyl; $R^1$ is —H, —$CH_3$, or —COOR; m is 0, 1, 2, 3, 4, 5, 6, 7, 8, 9, 10, 11, 12, 13, 14, 15, 16, 17, 18, or 19; and p is 0, 1, 2, 3, 4, 5, 6, 7, 8, 9, 10, 11, 12, 13, 14, 15, 16, 17, 18, or 19.

In another aspect, the olefinic substrates that may be used in the invention are represented by the structure of Formula 2, wherein: R is —H, optionally substituted $C_1$, $C_2$, $C_3$, $C_4$, $C_5$, or $C_6$ alkyl, optionally substituted $C_6$ aryl, optionally substituted heterocycle, or optionally substituted $C_5$, $C_6$, $C_7$, $C_8$, $C_9$, or $C_{10}$ cycloalkyl; $R^1$ is —H, —$CH_3$, or —COOR; m is 0, 1, 2, 3, 4, 5, 6, or 7; and p is 3, 4, 5, 6, 7, 8, 9, 10, 11, or 12.

In a further aspect, the olefinic substrates that may be used in the invention are represented by the structure of Formula 2, wherein: R is —H, optionally substituted $C_1$, $C_2$, or $C_3$ alkyl, optionally substituted $C_6$ aryl, or optionally substituted $C_5$, $C_6$, $C_7$, $C_8$, $C_9$, or $C_{10}$ cycloalkyl; $R^1$ is —H, —$CH_3$, or —COOR; m is 0, 1, 2, 3, 4, 5, 6, or 7; and p is 3, 4, 5, 6, 7, 8, 9, 10, 11, or 12.

In a further aspect, the olefinic substrates that may be used in the invention are represented by the structure of Formula 2, wherein: R is optionally substituted $C_1$, $C_2$, or $C_3$ alkyl; $R^1$ is —H; m is 0; and p is 6, 7, or 8.

In another aspect, the olefinic substrates that may be used in the invention are represented by the structure of Formula 2, wherein: R is $C_1$ alkyl; $R^1$ is —H; m is 0; and p is 7.

Still, in a further aspect, the olefinic substrates that may be used in the invention are represented by the structure of Formula 2, wherein: R is $C_1$ alkyl; $R^1$ is —H; m is 0; and p is 8.

Still, in a further aspect, the olefinic substrates that may be used in the invention are represented by the structure of Formula 2, wherein: R is $C_1$ alkyl; $R^1$ is —H; m is 2; and p is 7.

Cross Metathesis Substrates

Cross metathesis substrates that may be used in the invention disclosed herein are represented by the structure of the formula

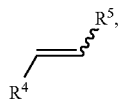

wherein: $R^4$ is —H or —$(CH_2)_{m1}OR^3$; $R^5$ is —$(CH_2)_{m1}OR^3$; $R^3$ is optionally substituted —$CO(C_1$-$C_{12}$ alkyl), optionally substituted —$CO(C_5$-$C_{10}$ cycloalkyl), optionally substituted —$CO(C_6$-$C_{10}$ aryl), or optionally substituted —$CO(C_5$-$C_{10}$ heterocycle); and $m_1$ is 1, 2, 3, 4, 5, 6, 7, 8, 9, 10, 11, 12, 13, 14, 15, 16, 17, 18, or 19.

In another aspect, the cross metathesis substrates that may be used in the invention are represented by the structure of formula

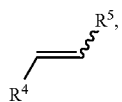

wherein: $R^4$ is —H or —$(CH_2)_{m1}OR^3$; $R^5$ is —$(CH_2)_{m1}OR^3$; $R^3$ is optionally substituted —$CO(C_1$-$C_{12}$ alkyl), optionally substituted —$CO(C_5$-$C_{10}$ cycloalkyl), optionally substituted —$CO(C_6$-$C_{10}$ aryl), or optionally substituted —$CO(C_5$-$C_{10}$ heterocycle); and $m_1$ is 1, 2, or 3.

In a further aspect, the cross metathesis substrates that may be used in the invention are represented by the structure of formula

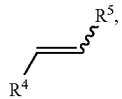

wherein: $R^4$ is —$(CH_2)_{m1}OR^3$; $R^5$ is —$(CH_2)_{m1}OR^3$; $R^3$ is optionally substituted —$CO(C_1$-$C_{12}$ alkyl); and $m_1$ is 1, 2, or 3.

Still a further aspect, the cross metathesis substrates that may be used in the invention $R^5$

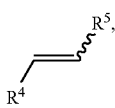

are represented by the structure of formula $R^4$, herein: $R^4$ is —$(CH_2)_{m1}OR^3$; $R^5$ is —$(CH_2)_{m1}OR^3$; $R^3$ is optionally substituted —$CO(C_1, C_2, C_3$ alkyl); and $m_1$ is 1, 2, or 3.

Still a further aspect, the cross metathesis substrates that may be used in the invention are represented by the structure of formula

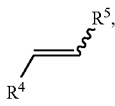

wherein: $R^4$ is —$(CH_2)_{m1}OR^3$; $R^5$ is —$(CH_2)_{m1}OR^3$; $R^3$ is optionally substituted —$CO(C_1$ alkyl); and $m_1$ is 1, 2, or 3.

Still a further aspect, the cross metathesis substrates that may be used in the invention are represented by the structure of formula

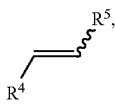

wherein: $R^4$ is —$(CH_2)_{m1}OR^3$; $R^5$ is —$(CH_2)_{m1}OR^3$; $R^3$ is —$CO(C_1$ alkyl); and $m_1$ is 1.

In another embodiment of the invention, cross metathesis substrates that may be used in the invention are represented by the structure of the formula

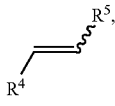

wherein: $R^4$ is —H, —OH, or —$(CH_2)_xPg$; $R^5$ is —$(CH_2)_xPg$; x is 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30; and Pg is an alcohol protecting group independently selected from methoxymethyl ether (MOM), methylthiomethyl ether (MTM), 2-methoxyethoxymethyl ether (MEM), bis-2-chloroethoxy)methyl ether, tetrahydropyranyl ether (THP), tetrahydrothiopyranyl ether, 4-methoxytetrahydropyranyl ether, 4-methoxythiotetrahydropyranyl ether, tetrahydrofuranyl ether, tetrahydrothiofuranyl ether, 1-ethoxyethyl ether, 1-methyl-1-methoxyethyl ether, 2-(phenylselenyl) ethyl ether, ethyl vinyl ether (EVE), tert-butyl ether (tBu), allyl ether, benzyl ether (Bn), ortho-benzyl ether, triphenylmethyl ether, alpha-naphthyldiphenylmethyl ether, para-methoxyphenyldiphenylmethyl ether, 9-(9-phenyl-10-oxo) anthryl ether, trimethylsilyl (TMS), isopropyldimethylsilyl ether, tert-butyldimethylsilyl ether (TBDMS), t-butyldiphenylsilyl ether (TBDPS), tribenzylsilyl ether, triisopropylsilyl ether, formate ester, acetate ester, trichloroacetate ester, phenoxyacetate ester, isobutyrate ester, propionate ester, butyrate ester, pivaloate ester, benzoate ester, adamantoate ester, methyl carbonate, 2,2,2-trichloromethyl carbonate, allyl carbonate, para-nitrophenyl carbonate, benzyl carbonate, para-nitrobenzyl carbonate, or S-benzyl thiocarbonate.

In another embodiment, of the invention, cross metathesis substrates that may be used in the invention are represented by the structure of the formula

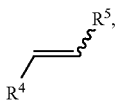

wherein: $R^4$ is —H, —OH, or —$(CH_2)_xPg$; $R^5$ is —$(CH_2)_xPg$; x is 1, 2, 3, 4, 5, or 6; and Pg is an alcohol protecting group independently selected from methoxymethyl ether (MOM), 2-methoxyethoxymethyl ether (MEM), tetrahydropyranyl ether (THP), 4-methoxytetrahydropyranyl ether, tetrahydrofuranyl ether, 1-ethoxyethyl ether, 1-methyl-1-methoxyethyl ether, ethyl vinyl ether (EVE), tert-butyl ether (tBu), allyl ether, benzyl ether (Bn), trimethylsilyl (TMS), isopropyldimethylsilyl ether, tert-butyldimethylsilyl ether (TBDMS), t-butyldiphenylsilyl ether (TBDPS), tribenzylsilyl ether, triisopropylsilyl ether, acetate ester, phenoxyacetate ester, and benzoate ester.

In another embodiment, of the invention, cross metathesis substrates that may be used in the invention are represented by the structure of the formula

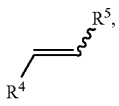

wherein: $R^4$ is —H, —OH, or —$(CH_2)_xPg$; $R^5$ is —$(CH_2)_xPg$; x is 1, 2, 3, or 4; and Pg is an alcohol protecting group independently selected from tetrahydropyranyl ether (THP), ethyl vinyl ether (EVE), tert-butyl ether (tBu), benzyl ether (Bn), trimethylsilyl (TMS), tert-butyldimethylsilyl ether (TBDMS), t-butyldiphenylsilyl ether (TBDPS), acetate ester, and benzoate ester.

In another embodiment, of the invention, cross metathesis substrates that may be used in the invention are represented by the structure of the formula

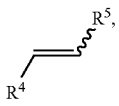

wherein: $R^4$ is —H, —OH, or —$(CH_2)_xPg$; and $R^5$ is —$(CH_2)_xPg$; x is 1 or 2; and Pg is an alcohol protecting group independently selected from tetrahydropyranyl ether (THP), benzyl ether (Bn), trimethylsilyl (TMS), tert-butyldimethylsilyl ether (TBDMS), acetate ester, and benzoate ester.

In another embodiment, of the invention, cross metathesis substrates that may be used in the invention are represented by the structure of the formula

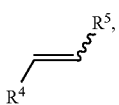

wherein: $R^4$ is —H, —OH, or —(CH$_2$)$_x$Pg; and $R^5$ is —(CH$_2$)$_x$Pg; x is 1 or 2; and Pg is an alcohol protecting group independently selected from tetrahydropyranyl ether (THP), benzyl ether (Bn), trimethylsilyl (TMS), and acetate ester.

In another embodiment of the invention, cross metathesis substrates that may be used in the invention are represented by the structure of the formula

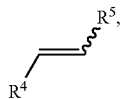

wherein: $R^4$ is —H, —OH, or —(CH$_2$)$_x$Pg; $R^5$ is —(CH$_2$)$_x$Pg; x is 1 or 2; and Pg is acetate ester (CH$_3$C(O)O—).

The cross metathesis substrates that may be used in the invention, of formula

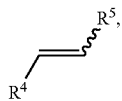

can be an unsaturated alcohol or a protected unsaturated alcohol or an α,ω-unsaturated diol or a protected α,ω-unsaturated diol, or a mixture thereof.

In another aspect of the invention, the cross metathesis substrates that may be used in the invention, represented by the structure of formula

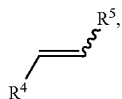

can be allyl acetate, 1,4-diacetoxy-2-butene, 3-butenol, 3-butenyl acetate, 3-pentenol, 3-pentenyl acetate, 3-hexenol, 3-hexenyl acetate, 3-hexene-1,6-diol, or 1,6-diacetoxy-3-hexene.

In a further aspect of the invention the cross metathesis substrates that may be used in the invention, represented by the structure of formula

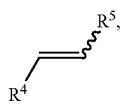

can be 1,4-diacetoxy-2-butene or 1,6-diacetoxy-3-hexene.

Unsaturated Protected Alcohol Intermediate

Unsaturated protected alcohol intermediates that may be used in the invention disclosed herein are represented by the structure of Formula 2a

wherein: R is —H, optionally substituted C$_1$-C$_{12}$ alkyl, optionally substituted C$_6$-C$_{10}$ aryl, optionally substituted heterocycle, or optionally substituted C$_5$-C$_{10}$ cycloalkyl; $R^2$ is —OR$^3$; $R^3$ is optionally substituted —CO(C$_1$-C$_{12}$ alkyl), optionally substituted —CO(C$_5$-C$_{10}$ cycloalkyl), optionally substituted —CO(C$_6$-C$_{10}$ aryl), or optionally substituted —CO(C$_5$-C$_{10}$ heterocycle); $m_1$ is 1, 2, 3, 4, 5, 6, 7, 8, 9, 10, 11, 12, 13, 14, 15, 16, 17, 18, or 19; p is 0, 1, 2, 3, 4, 5, 6, 7, 8, 9, 10, 11, 12, 13, 14, 15, 16, 17, 18, or 19; and with the proviso that the sum of any combination of $m_1$ and p is 1, 2, 3, 4, 5, 6, 7, 8, 9, 10, 11, 12, 13, 14, 15, 16, 17, 18, 19, or 20.

In another aspect, unsaturated protected alcohol intermediates that may be used in the invention are represented by the structure of Formula 2a, wherein: R is —H, optionally substituted C$_1$, C$_2$, C$_3$, C$_4$, C$_5$, or C$_6$ alkyl, optionally substituted C$_6$ aryl, optionally substituted heterocycle or optionally substituted C$_5$, C$_6$, C$_7$, C$_8$, C$_9$, or C$_{10}$ cycloalkyl; $R^2$ is —OR$^3$; $R^3$ is optionally substituted —CO(C$_1$, C$_2$, C$_3$, C$_4$, C$_5$, C$_6$ alkyl), optionally substituted —CO(C$_5$, C$_6$, C$_7$, C$_8$, C$_9$, C$_{10}$ cycloalkyl), optionally substituted —CO(C$_6$ aryl); $m_1$ is 1, 2, 3; p is 3, 4, 5, 6, 7, 8, 9, 10, 11, or 12; and with the proviso that the sum of any combination of $m_1$ and p is 4, 5, 6, 7, 8, 9, 10, 11, 12, 13, 14, or 15.

In another aspect, unsaturated protected alcohol intermediates that may be used in the invention are represented by the structure of Formula 2a, wherein: R is —H, optionally substituted C$_1$, C$_2$, or C$_3$ alkyl; $R^2$ is —OR$^3$; $R^3$ is optionally substituted —CO(C$_1$, C$_2$, C$_3$ alkyl); $m_1$ is 1 or 2; and p is 6, 7, or 8.

In another aspect, unsaturated protected alcohol intermediates that may be used in the invention are represented by the structure of Formula 2a, wherein: R is C$_1$ alkyl; $R^2$ is —OR$^3$; $R^3$ is —CO(C$_1$ alkyl); $m_1$ is 1 or 2; and p is 6, 7, or 8.

In another aspect, unsaturated protected alcohol intermediates that may be used in the invention are represented by the structure of Formula 2a, wherein: R is C$_1$ alkyl; $R^2$ is —OR$^3$; $R^3$ is —CO(C$_1$ alkyl); $m_1$ is 1; and p is 7.

In another aspect, unsaturated protected alcohol intermediates that may be used in the invention are represented by the structure of Formula 2a, wherein: R is C$_1$ alkyl; $R^2$ is —OR$^3$; $R^3$ is —CO(C$_1$ alkyl); $m_1$ is 1; and p is 8.

Unsaturated Alcohol

Unsaturated alcohols that may be used in the invention disclosed herein are represented by the structure of the Formula 3

wherein: R is —H, optionally substituted C$_1$-C$_{12}$ alkyl, optionally substituted C$_6$-C$_{10}$ aryl, optionally substituted heterocycle, or optionally substituted C$_5$-C$_{10}$ cycloalkyl; $m_1$ is 1, 2, 3, 4, 5, 6, 7, 8, 9, 10, 11, 12, 13, 14, 15, 16, 17, 18, or 19; p is 0, 1, 2, 3, 4, 5, 6, 7, 8, 9, 10, 11, 12, 13, 14, 15, 16, 17, 18, or 19; and with the proviso that the sum of any combination of $m_1$ and p is 1, 2, 3, 4, 5, 6, 7, 8, 9, 10, 11, 12, 13, 14, 15, 16, 17, 18, 19, or 20.

In another aspect, unsaturated alcohols that may be used in the invention are represented by the structure of Formula 3, wherein: R is —H, optionally substituted $C_1$, $C_2$, $C_3$, $C_4$, $C_5$, or $C_6$ alkyl, optionally substituted $C_6$ aryl, optionally substituted heterocycle, or optionally substituted $C_5$, $C_6$, $C_7$, $C_8$, $C_9$, or $C_{10}$ cycloalkyl; $m_1$ is 1, 2, or 3; p is 3, 4, 5, 6, 7, 8, 9, 10, 11, or 12; and with the proviso that the sum of any combination of $m_1$ and p is 4, 5, 6, 7, 8, 9, 10, 11, 12, 13, 14, or 15.

In another aspect, unsaturated alcohols intermediates that may be used in the invention are represented by the structure of Formula 3, wherein: R is —H, optionally substituted $C_1$, $C_2$, or $C_3$ alkyl; $m_1$ is 1 or 2; and p is 6, 7, or 8.

In another aspect, unsaturated alcohols that may be used in the invention are represented by the structure of Formula 3, wherein: R is $C_1$ alkyl; $m_1$ is 1 or 2; and p is 6, 7, or 8.

In another aspect, unsaturated alcohols that may be used in the invention are represented by the structure of Formula 3, wherein: R is $C_1$ alkyl; $m_1$ is 1; and p is 7.

In another aspect, unsaturated alcohols that may be used in the invention are represented by the structure of Formula 3, wherein: R is $C_1$ alkyl; $m_1$ is 1; and p is 8.

The terms "optionally substituted" have been defined above in the terminology and definitions section.

It is to be understood that both the foregoing general description and the following detailed description and experimental examples are exemplary and explanatory only and are not restrictive of the invention claimed. As used herein, the use of the singular includes the plural unless specifically stated otherwise.

EXPERIMENTAL

The following examples are for illustrative purposes only and are not intended, nor should they be construed as limiting the invention in any manner. Those skilled in the art will appreciate that variations and modifications of the following examples can be made without exceeding the spirit or scope of the invention.

All reactions involving metal complexes were conducted in oven-dried glassware under an argon or nitrogen atmosphere using standard Schlenk techniques. Chemicals and solvents were obtained from Sigma-Aldrich, Strem, Alfa Aesar, Nexeo, Brenntag, AG Layne and TCI. Commercially available reagents were used as received unless otherwise noted. Silica gel was purchased from Fisher (0.040-0.063 m, EMD Millipore). Catalyst starting materials C711, C627, C705, and C827 were prepared using known methods. Ruthenium pincer complexes Chlorocarbonylhydrido[4,5-bis-(di-i-propyl phosphinomethyl) acridine] Ruthenium (II) (commercially available from Strem) and Chlorocarbonylhydrido[4,5-bis-(di-cyclohexyl phosphinomethyl) acridine] Ruthenium (II) were prepared using known methods.

$^1$H and $^{13}$C NMR spectra were recorded on a Varian 400 MHz spectrometer. Chemical shifts are reported in ppm downfield from $Me_4Si$ by using the residual solvent peak as an internal standard $CDCl_3$—($\delta$ 7.24 ppm); $CD_2Cl_2$—($\delta$ 5.32 ppm). Spectra were analyzed and processed using VnmrJ 4.0 software.

In some cases volatile products were analyzed using an Agilent 6850 gas chromatography (GC) instrument with a flame ionization detector (FID). The following conditions and equipment were used:
Column: HP-5, 30 m×0.25 mm (ID)×0.25 μm film thickness.
  Manufacturer: Agilent
GC conditions: Injector temperature: 250° C.
  Detector temperature: 280° C.
Oven temperature: Starting temperature: 100° C., hold time: 1 minute.
  Ramp rate 10° C./min to 250° C., hold time: 12 minutes.
Carrier gas: Helium
Mean gas velocity: 31.3±3.5% cm/sec (calculated)
Split ratio: ~50:1

In other cases volatile products were analyzed using an Agilent 5890 gas chromatography (GC) instrument with a flame ionization detector (FID). The following conditions and equipment were used:
Column: HP-5, 30 m×0.25 mm (ID)×0.25 μm film thickness.
  Manufacturer: J&W
GC and column conditions: Injector temperature: 300° C.
  Detector temperature: 320° C.
Oven temperature: Starting temperature: 100° C., hold time: 0.5 minute.
  Ramp rate 30° C./min to 320° C., hold time: 10 minutes.
Carrier gas: Helium
Mean gas velocity: 31.3±3.5% cm/sec (calculated)
Split ratio: ~20:1

The products were characterized by comparing peaks with known standards, in conjunction with supporting data from mass spectrum analysis (GCMS-Agilent 5973N). GCMS analysis was accomplished with a second HP-5, 30 m×0.25 mm (ID)×0.25 jam film thickness GC column, using the same method as above.

The following abbreviations are used in the examples:

| | |
|---|---|
| $CH_2Cl_2$ | dichloromethane |
| RT | room temperature |
| KOH | potassium hydroxide |
| MeOH | methanol |
| $MgSO_4$ | magnesium sulfate |
| [RuHCl(A-iPr-PNP)(CO)] | 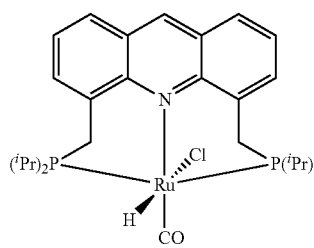 Chlorocarbonylhydrido[4,5-bis-(di-i-propyl phospinomethyl) acridine]Ruthenium (II) [CAS 1101230-25-4] |
| [RuHCl(A-Cy-PNP)(CO)] | 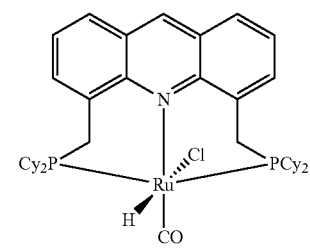 Chlorocarbonylhydrido[4,5-bis-(di-cyclohexyl phospinomethyl) acridine]Ruthenium (II) |
| $NH_3$ | ammonia |
| $H_2$ | hydrogen |
| psi | pound per square inch |
| L | liter |
| mL | milliliter |
| μL | microliter |
| $CDCl_3$ | deuterated chloroform |
| $CD_2Cl_2$ | deuterated dichloromethane |
| mtorr | millitorr |
| h | hour |

| | | |
|---|---|---|
| C711 | 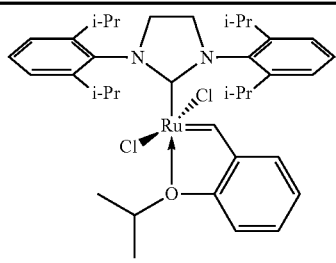 [1,3-bis(2,6-di-isopropylphenyl-2-imidazolidinylidene] dichloro(o-isopropoxyphenylmethylene)Ruthenium(II) CAS [635679-24-2] | |
| PtO$_2$ | platinum oxide | |
| NaHCO$_3$ | sodium hydrogen carbonate | |
| THF | tetrahydrofuran | |
| C627 | 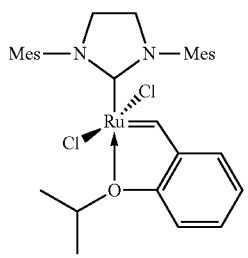 [1,3-bis-(2,4,6-trimethylphenyl)-2-imidazolidinylidene] dichloro(o-isopropoxyphenylmethylene)Ruthenium(II) CAS [301224-40-8] | |
| Mes | 2,4,6-trimethylphenyl | |
| C705 | 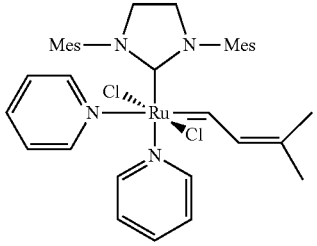 [1,3-bis-(2,4,6-trimethylphenyl)-2-imidazolidinylidene] dichloro(3-methyl-2-butenylidene) bis(pyridene) Ruthenium (II) | |
| Cy | cyclohexyl | |
| TEMPO | (2,2,6,6-tetramethyl-piperidin-1-yl)oxyl | |
| C827 | [1,3-bis-(2,4,6-trimethylphenyl)-2-imidazolidinylidene] dichloro(3-methyl-2-butenylidene) (tricyclohexylphosphine) Ruthenium (II) CAS [253688-91-4] | |
| TMS$_2$O | hexamethyldisiloxane | |
| Bpy | 2,2'-bipyridyl | |
| MeCN | acetonitrile | |
| CuI | copper (I) iodide | |
| CuCl | copper (I) chloride | |
| CuCl$_2$ | copper (II) chloride | |
| CuBr | copper (I) bromide | |
| CuBr$_2$ | copper (II) bromide | |
| CuOAc | copper acetate | |
| Cu(OTf)$_2$ | copper(II) trifluoromethanesulfonate | |
| Cu(OAc)$_2$ | copper (II) acetate | |
| Cu(MeCN)$_4$(OTf) | tetrakis(acetonitrile)copper(I)trifluoromethanesulfonate | |
| AcCl | acetyl chloride | |
| HCl | hydrogen chloride | |
| NaOH | sodium hydroxide | |
| KBr | potassium bromide | |
| NCS | N-chlorosuccinimide | |
| TLC | thin layer chromatography | |
| TMEDA | N,N,N',N'-tetramethylethylenediamine | |
| IPA | iso-propanol | |
| DCB | cis-1,4-dichloro-2-butene | |

The following experimental methods illustrate how compounds according to the invention can be made. Those skilled in the art will be routinely able to modify and/or adapt the following methods to synthesize any compound of the invention.

Step a General Conditions for Screening the Cross-Metathesis of Methyl 10-undecenoate and 1,4-Diacetoxy-2-butene In an argon filled glove box, a 20 mL scintillation vial equipped with a magnetic stir bar, was charged with methyl 10-undecenoate (0.50 g, 2.5 mmol) and 1,4-diacetoxy-2-butene (1.30 g, 7.6 mmol, 3 equiv). Ruthenium catalyst (500 ppm, 0.25 mL of a 0.0050 M solution in dichloromethane) was subsequently added, the vial was sealed, placed under high vacuum and stirred at 45° C. for 4 hours. The reaction was stirred rapidly for 2 hours then diluted with a solution of potassium hydroxide (1.41 g, 25.2 mmol) in methanol (50 mL) and stirred overnight at RT. The reaction mixture was subsequently partitioned between water and dichloromethane (1:1 v/v, 600 mL), the organic phase separated and the aqueous phase extracted with dichloromethane (2×150 mL). The organic extracts were combined, dried over MgSO$_4$, filtered and the solvent was evaporated under reduced pressure. The product was purified by column chromatography to afford Methyl 12-hydroxydodec-10-enoate as shown below.

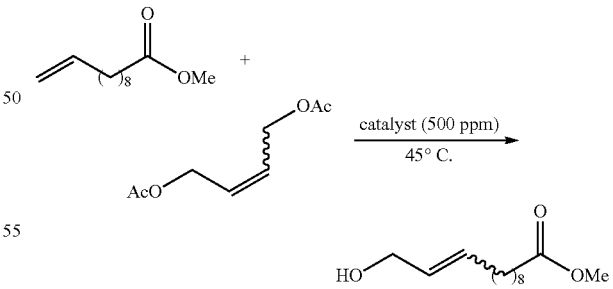

| entry | catalyst | % conv | % yield |
|---|---|---|---|
| 1 | C627 | 57.8 | 54.0 |
| 2 | C705 | 14.2 | 13.5 |
| 3 | C711 | 95.5 | 94.0 |
| 4 | C827 | 93.3 | 91.4 |

Step b Preparation of Methyl 12-hydroxydodecanoate

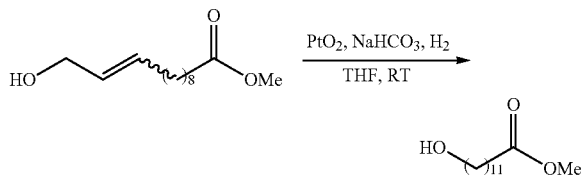

A 250 mL round bottom flask equipped with a magnetic stir bar was charged with methyl 12-hydroxydodec-10-enoate (3.50 g, 15.3 mmol), PtO$_2$ (230 mg, 1.0 mmol), NaHCO$_3$ (4.51 g, 53.7 mmol), and THF (60 mL). The reaction was fitted with a rubber septum, sparged with hydrogen then stirred under an atmosphere of hydrogen overnight. The reaction was then filtered through celite and the solvent was evaporated under reduced pressure. The resulting residue was purified by column chromatography to afford methyl 12-hydroxydodecanoate (2.83 g, 80.0% yield, >98% pure).

$^1$H NMR (400 MHz, CDCl$_3$) δ 1.19-1.38 (m, 14H), 1.42 (br s, 1H), 1.50-1.68 (m, 4H), 2.30 (t, J=7.5 Hz, 2H), 3.63 (t, J=6.6 Hz, 2H), 3.66 (s, 3H).

$^{13}$C NMR (101 MHz, CDCl$_3$) δ 25.1, 25.9, 29.3, 29.3, 29.5, 29.5, 29.6, 29.7, 32.9, 34.2, 51.6, 63.2, 174.5.

Step c General Conditions for the Tandem Amination-Reduction of Methyl 12-hydroxydodec-10-enoate In an argon filled glove box, a 60 mL Parr reactor equipped with a glass liner and magnetic stir bar, was charged with methyl 12-hydroxydodec-10-enoate (0.250 g, 1.09 mmol), [RuHCl(A-iPr-PNP)(CO)] (1.3 mg, 0.0021 mmol), and toluene (3 mL). The reactor was sealed, purged, and pressurized with ammonia (100 psi). The reactor was subsequently pressurized with hydrogen (75-150 psi) and sealed. The reactor was heated to 155° C. with stirring for 18 h. Product distributions were determined by GC.

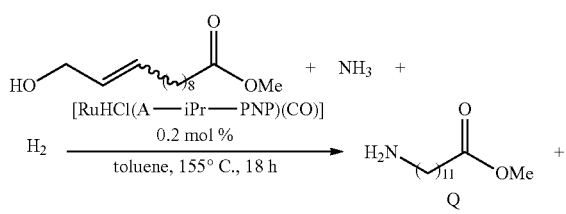

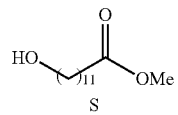

| entry | NH$_3$ (psi[1]) | H$_2$ (psi[1]) | % conv | % Q | % S |
|---|---|---|---|---|---|
| 1 | 100 | 150 | 100 | 74.1 | 12.6 |
| 2 | 100 | 100 | 100 | 77.4 | 11.4 |
| 3 | 100 | 90 | 100 | 73.4 | 14.2 |
| 4 | 100 | 75 | 100 | 69.4 | 9.1 |

[1]psi at 27° C.

Step d General Conditions for the Amination of Methyl 12-hydroxydodecaenoate In an argon filled glovebox, a 60 mL Parr reactor equipped with a glass liner and magnetic stir bar was charged with methyl 12-hydroxydodecanoate (0.20 g, 0.87 mmol), a Ruthenium pincer complex A or B (0.0018 mmol), and solvent (2 mL). The reactor was sealed, purged, and pressurized with ammonia. The reactor was heated to 155° C. with stirring and product distributions were subsequently determined by GC.

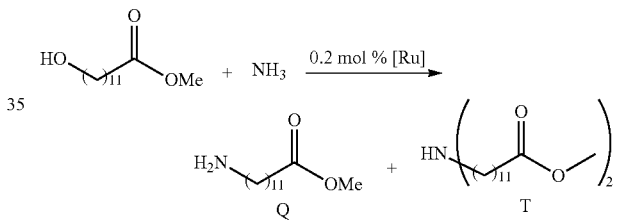

| entry | [Ru][1] | NH$_3$ (psi[3], equiv) | solvent | temp (° C.) | time (h) | % conv | % Q | % T |
|---|---|---|---|---|---|---|---|---|
| 1 | A | 200 (~75) | dioxane | 135 | 18 | 0 | — | — |
| 2 | B | 80 (~15) | toluene | 155 | 18 | 97.6 | 95.9 | ND[2] |
| 3 | A | 80 (~15) | toluene | 155 | 15 | 100 | 96.6 | 2.5 |

[1]A: [RuHCl(A—iPr-PNP)(CO)] B: [RuHCl(A-Cy-PNP)(CO)]
[2]not detected
[3]psi at 27° C.

Step e General Conditions for the Oxidation of Methyl 12-hydroxydodec-10-enoate with Ammonium Hydroxide to Methyl 11-cyanoundec-10-enoate A 60 mL Parr reactor equipped with a glass liner and magnetic stir bar was charged with copper catalyst (0.0218 mmol), 2,2'-bipyridyl (3.4 mg, 0.0218 mmol), TEMPO (3.4 mg, 0.0218 mmol), acetonitrile (1.4 mL), ammonium hydroxide (0.066 mL, 0.870 mmol), and methyl 12-hydroxydodec-10-enoate (0.100 g, 0.435 mmol). The reactor was sealed and pressurized with compressed air (110 psi). The reactor was heated to 50° C. with stirring for 24 h. Product distributions were determined by GC.

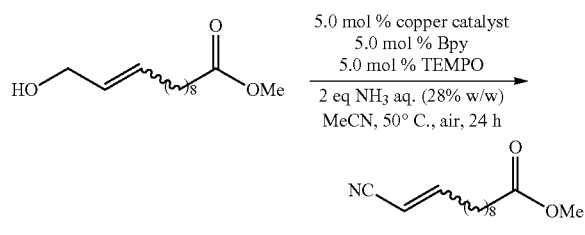

One-Pot synthesis of Methyl 11-cyanoundec-10-enoate

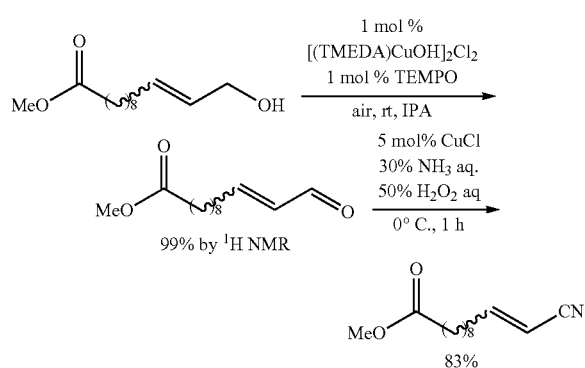

In air, to a 40 mL scintillation vial equipped with a stirring bar was charged TEMPO (4.00 mg, 0.022 mmol), [(TMEDA)Cu(μ-OH)]$_2$Cl$_2$ (500 mg, 0.022 mmol), methyl 12-hydroxy-10-dodecenoate (500 mg, 2.20 mmol), and iso-propanol (4 mL). The reaction was sparged with air via a needle. After 15 h, the reaction mixture was analyzed by $^1$H NMR spectroscopy to quantify methyl 12-oxo-10-dodecenoate. To the crude reaction mixture was added CuCl (11 mg, 0.11 mmol) as a solid and 30% ammonia aq. (528 mg, 2.20 mmol). To this reaction was carefully and slowly added 50% hydrogen peroxide aq. (1.05 g, 7.70 mmol) over a period of 15 minutes. The addition of hydrogen peroxide leads to an exothermic reaction with gas evolution. After complete addition of hydrogen peroxide, the reaction was allowed to stir at room temperature for 30 minutes. A second equivalent of 30% ammonia aq. and another 3.5 equivalent of 50% hydrogen peroxide aq. was added to the reaction and allowed to proceed in the same manner. The distribution of products were analyzed by gas chromatography.

| entry | copper catalyst | % yield |
|---|---|---|
| 1[1] | Cu(MeCN)$_4$(OTf) | 100 |
| 2 | CuI | 51.8 |
| 3 | CuCl | 69.1 |
| 4 | CuCl$_2$ | 6.0 |
| 5 | CuBr | 45.0 |
| 6 | CuBr$_2$ | 18.6 |
| 7 | CuOAc | 48.4 |
| 8 | Cu(OTf)$_2$ | 62.8 |
| 9 | Cu(MeCN)$_4$(OTf) | 73.8 |
| 10 | Cu(OAc)$_2$ | 25.8 |

[1] 10 mol % catalyst loading

To work up the reaction, iso-propanol was removed on the rotary evaporator. The resulting aqueous layer was carefully decanted to leave behind an oily residue. The crude product was taken up into diethyl ethyl and filtered through a tall silica pad to remove copper species. The filtrate was concentrated to dryness to give a yellow oil. $^1$H NMR (400 MHz, CDCl$_3$, trans): δ 6.75-6.67 (m, 1H), 5.31 (d, J=16 Hz, 1H), 3.66 (s, 3H), 2.32-2.28 (t, J=7.2 Hz, 2H), 2.24-2.18 (m, 2H), 1.63-1.59 (m, 2H), 1.44-1.41 (m, 1H), 1.29 (br s, 9H). $^{13}$C NMR (101 MHz, CDCl$_3$, trans): δ 173.7, 155.8, 117.3, 99.5, 51.1, 33.7, 33.0, 28.9, 28.8, 28.7, 28.6, 27.4, 24.6.

Synthesis of methyl 11-cyano-10-undecenoate from methyl 12-oxo-10-dodecenoate

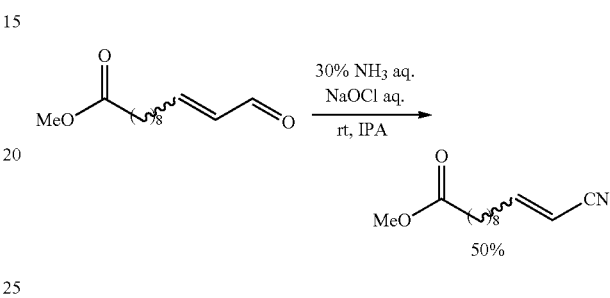

Procedure 1: In air, to a 40 mL vial equipped with a stirring bar was charged methyl 12-oxo-10-dodecenoate (250 mg, 1.10 mmol), 30% ammonia aq. (300 μL, 2.20 mmol), and iso-propanol (2 mL). To the reaction mixture was added 1.1 M sodium hypochlorite (2.00 mL, 2.20 mmol) over 5 minutes. The reaction mixture was stirred at room temperature for 0.5 h. The distribution of products were analyzed by gas chromatography.

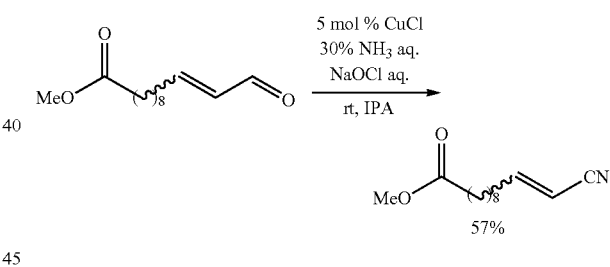

Procedure 2: In air, to a 40 mL scintillation vial equipped with a stirring bar was charged CuCl (5.00 mg, 0.11 mmol), methyl 12-oxo-10-dodecenoate (250 mg, 1.10 mmol), 30% ammonia aq. (300 μL, 2.20 mmol), and iso-propanol (2 mL). To this reaction mixture was added 1.1 M sodium hypochlorite (4.00 mL, 4.40 mmol) dropwise over 10 minutes. The reaction mixture was stirred at room temperature for 0.5 h. The distribution of products were analyzed by gas chromatography.

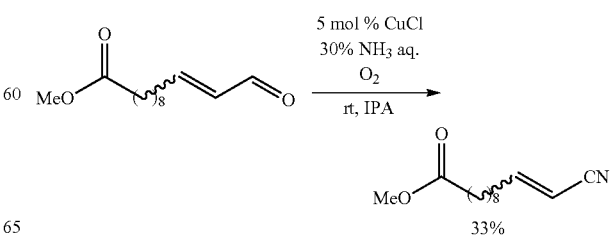

Procedure 3: In air, a 60 mL Parr reactor equipped with a stirring bar was charged methyl 12-oxo-10-dodecenoate (250 mg, 1.10 mmol), 30% ammonia aq. (300 µL, 2.20 mmol), and iso-propanol (2 mL). The reactor was sealed and pressurized with oxygen (100 psi). The reactor was heated to 75° C. for 6 h. The distribution of products were analyzed by gas chromatography.

Step f Preparation of Methyl 12-aminododecanoate from Methyl 11-cyano-10-undecenoate

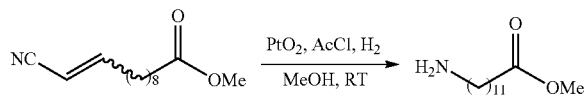

A 60 mL Parr reactor equipped with a glass liner and magnetic stir bar was charged with methyl 11-cyano-10-undecenoate (0.100 g, 0.448 mmol), PtO$_2$ (15.2 mg, 0.066 mmol), acetyl chloride (0.031 mL, 0.448 mmol), and methanol (13 mL). The reactor was sealed and pressurized with hydrogen (20 bar). The reaction was stirred for 24 h at RT. The reaction mixture was subsequently filtered through celite and the solvent was evaporated under reduced pressure. Product distributions were determined by GC (98.7 mg, 96.1% yield, >98% pure).

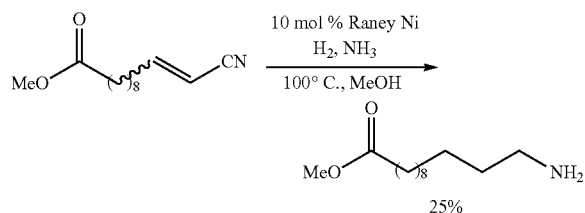

In an argon filled glovebox, a 60 mL Parr reactor equipped with a glass magnetic stir bar was charged Raney Ni (12 mg, 0.18 mmol), methyl 11-cyano-10-undecenoate (410 mg, 1.80 mmol), and methanol (3 mL). The reactor was removed from the glovebox and 500 µL NH$_3$ (7 N in methanol) was added to the reactor. The reactor was sealed, purged, and pressurized with hydrogen (120 psi). The reactor was heated to 100° C. with stirring for 24 h. The distribution of products were analyzed by gas chromatography.

Step g General Conditions for the Oxidation of Methyl 12-hydroxydodecanoate with Ammonium Hydroxide to Methyl 11-cyanoundecanoate

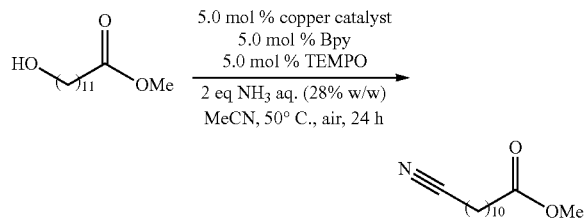

A 60 mL Parr reactor equipped with a glass liner and magnetic stir bar was charged with copper catalyst (0.022 mmol), 2,2'-bipyridyl (3.4 mg, 0.022 mmol), TEMPO (3.4 mg, 0.022 mmol), acetonitrile (1.4 mL), ammonium hydroxide (0.066 mL, 0.87 mmol), and methyl 12-hydroxydodecanoate (0.100 g, 0.435 mmol). The reactor was sealed, pressurized with compressed air (110 psi), and subsequently heated to 50° C. with stirring for 24 h. Product distributions were determined by GC.

| entry | copper catalyst | % yield |
|---|---|---|
| 1 | CuI | 100 |
| 2 | CuCl | 25.7 |
| 3 | CuCl$_2$ | 0.0 |
| 4 | CuBr | 71.3 |
| 5 | CuBr$_2$ | 4.6 |
| 6 | CuOAc | 29.6 |
| 7 | Cu(OTf)$_2$ | 16.6 |
| 8 | Cu(OAc)$_2$ | 3.3 |
| 9 | Cu(MeCN)$_4$(OTf) | 71.2 |
| 10[1] | CuCl$_2$ | 7.7 |

[1]reaction conducted at 120° C.

Step h Preparation of Methyl 12-aminododecanoate from Methyl 11-cyanoundec-10-enoate

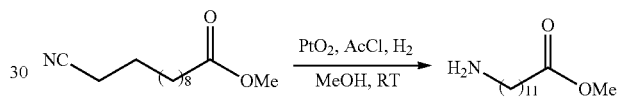

A 60 mL Parr reactor equipped with a glass liner and magnetic stir bar was charged with methyl 11-cyanoundec-10-enoate (0.100 g, 0.444 mmol), PtO$_2$ (15.2 mg, 0.066 mmol), acetyl chloride (0.031 mL, 0.444 mmol), and methanol (13 mL). The reactor was sealed and pressurized with hydrogen (20 bar). The reaction was stirred for 24 h at RT. The reaction mixture was subsequently filtered through celite and the solvent was evaporated under reduced pressure. No further purification was required (0.101 g, >99.9%, >98% pure).

Synthesis of Methyl 12-hydroxydodec-10-enoate

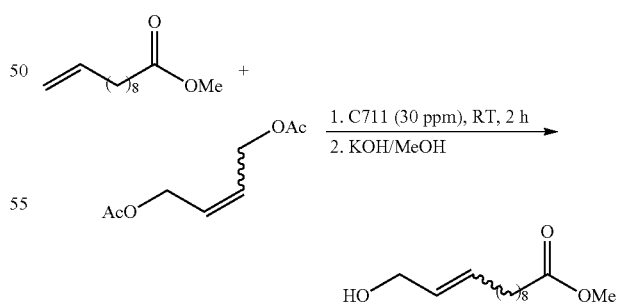

An oven-dried two-neck 500 mL round bottom flask equipped with a magnetic stir bar was charged with methyl 10-undecenoate (25.0 g, 126 mmol) and 1,4-diacetoxy-2-butene (65.9 g, 189 mmol). The flask was fitted with a vacuum adapter and a rubber septum then placed under high vacuum before C711 (2.7 mg, 0.0038 mmol, dissolved 0.25 mL dichloromethane) was added by syringe. The reaction was subjected to hydrolysis in basic conditions, by stirred rapidly for 2 hours then diluted with a solution of potassium hydroxide (1.41 g, 25.2 mmol) in methanol (50 mL) and stirred overnight at room temperature. The reaction mixture was subsequently partitioned between water and dichloromethane (1:1 v/v, 600 mL), the organic phase separated and the aqueous phase extracted with dichloromethane (2×150 mL). The organic extracts were combined, dried over MgSO$_4$, filtered and the solvent was evaporated under reduced pressure. The product was purified by column chromatography to afford methyl 12-hydroxydodec-10-enoate (18.0 g, 62.4% yield, 82.9% trans, >98% pure).

$^1$H NMR (400 MHz, CDCl$_3$, trans) δ 1.16-1.41 (m, 10H), 1.50-1.65 (m, 2H), 1.76 (br s, 1H), 1.92-2.09 (m, 2H), 2.27 (t, J=7.5 Hz, 2H), 3.63 (s, 3H), 4.04 (d, J=5.2 Hz, 2H), 4.15 (for the cis isomer, d, J=6.3 Hz), 5.42-5.74 (m, 2H).

$^{13}$C NMR (101 MHz, CDCl$_3$, trans) δ 25.0, 29.1, 29.2, 29.2, 29.2, 29.3, 32.2, 34.2, 51.5, 63.8, 129.0, 133.3, 174.4.

$^{13}$C NMR (101 MHz, CDCl$_3$, cis, selected resonances) δ 58.6, 128.6, 133.0.

Synthesis of [(TMEDA)Cu(μ-OH)]$_2$Cl$_2$ (Di-μ-hydroxo-bis[(N,N,N',N'-tetramethylethylenediamine)copper]chloride)

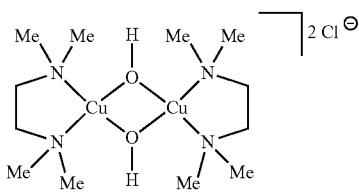

[(TMEDA)Cu(μ-OH)]$_2$Cl$_2$ was synthesized according to published procedure: Collman, J. P.; Zhong, M.; Zhang, C.; Costanzo, S. *J. Org. Chem.* (2001), 66, 7892. [(TMEDA)Cu(μ-OH)]$_2$Cl$_2$ can also be synthesized in acetone or iso-propanol following the published protocol.

Synthesis of 10-Dodecenoic Acid, 12-Oxo-, Methyl Ester

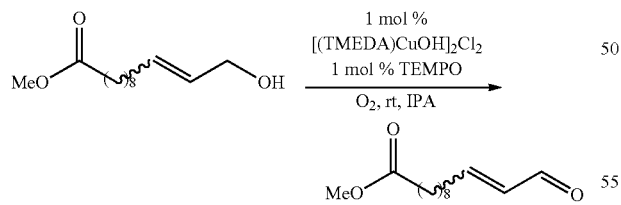

Procedure 1:

A 60 mL Parr reactor equipped with a stirring bar was charged [(TMEDA)Cu(μ-OH)]$_2$Cl$_2$ (2.5 mg, 0.0055 mmol), TEMPO (2.0 mg, 0.011 mmol), methyl 12-hydroxy-10-dodecenoate (250 mg, 1.10 mmol), and iso-propanol (3 mL). The reactor was sealed and pressurized with oxygen gas (80 psi). The reactor was stirred at room temperature for 8 h. The product (99%) was determined by $^1$H NMR spectroscopy. methyl 12-oxo-10-dodecenoate was isolated by column chromatography using hexanes and 10% ethyl acetate. $^1$H NMR (400 MHz, CDCl$_3$, trans): δ 9.50 (d, J=7.6 Hz, 1H), 6.87-6.83 (m, 1H), 6.15-6.10 (m, 1H), 3.67 (s, 3H), 2.34-2.29 (m, 4H), 1.62-1.59 (m, 2H), 1.51-1.49 (m, 1H), 1.31 (br s, 9H).

Procedure 2

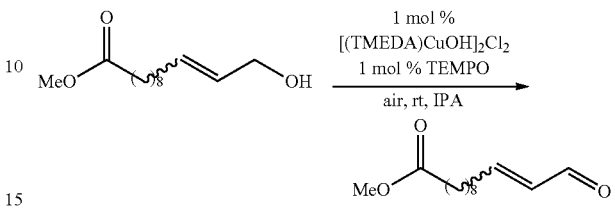

A 40 mL scintillation vial equipped with a stirring bar was charged [(TMEDA)Cu(μ-OH)]$_2$Cl$_2$ (5.0 mg, 0.011 mmol), TEMPO (4.0 mg, 0.022 mmol), methyl 12-hydroxy-10-dodecenoate (500 mg, 2.20 mmol), and iso-propanol (3 mL). The reaction mixture was sparged with air via a needle. The reaction was stirred at room temperature for 15 h. The product (99%) was determined by $^1$H NMR spectroscopy.

Synthesis of cis-1,4-dichloro-2-butene

The preparation of cis-1,4-dichloro-2-butene from cis-2-butene-1,4-diol was adapted from the procedure for the conversion of alcohols to chlorides (Snyder, D. C. *J. Org. Chem.* 1995, 60, 2638). Inside an argon-filled glovebox, to an oven-dried 500 mL round-bottom flask equipped with a large magnetic stirring bar was added trimethylsilyl chloride (129 g, 150 mL, 1.18 mol). The reaction was capped with a rubber septum and removed from the glovebox. The flask was placed in a water ice bath. To the reaction mixture was added cis-2-butene-1,4-diol (50.0 g, 46.4 mL, 0.565 mol) via syringe. After 15 minutes of stirring, to the reaction mixture was added 10 mol % of DMSO (8.20 mL, 0.237 mol) with respect to trimethylsilyl chloride. After 1 h of vigorous stirring, the reaction mixture was allowed to settle leading to a biphasic system. The top layer containing TMS$_2$O was decanted from the viscous oil. Product distributions were analyzed by gas chromatography and were compared to authentic sample of cis-1,4-dichloro-2-butene.

Methyl, 12-chloro-10-dodecenoate

In an argon filled glovebox, a solution of methyl-10-undecenoate (20.0 g; 101 mmol) and DCB (15.9 mL; 151 mmol) in a scintillation vial was added C627 (3.2 mg; 5.0 μmole). The reaction was allowed to proceed at 40° C. and 4 torr of vacuum for 2.5 hours. Then, the reaction was cooled to room temperature, vacuum removed and the product was purified by chromatography to afford methyl, 12-chloro-10- dodecenoate (21.0 g; 85.1 mmol; 84.4% yield). $^1$H NMR (400 MHz, CDCl$_3$) δ 1.23-1.32 (br s, 8H), 1.32-1.41 (m, 2H), 1.56-1.66 (m, 2H), 2.04 (q, J=7.0 Hz, 2H) [cis 2.10 (q, J=6.5 Hz)], 2.30 (t, J=7.5 Hz, 2H), 3.66 (s, 3H), 4.03 (d, J=7.0 Hz, 2H) [cis 4.09 (d, J=5.3 Hz)], 5.54-5.65 (m, 1H), 5.71-5.81 (m, 1H);

$^{13}$C NMR (101 MHz, CDCl$_3$) δ 24.9, 28.8, 29.0, 29.1, 29.1, 29.2, 32.0, 34.1, 45.5, 51.4, 125.8, 136.2, 174.3.

Methyl, 12-amino-10-dodecenoate

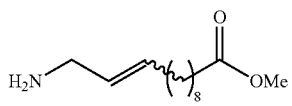

In an argon filled glovebox, a glass liner equipped with a magnetic stir bar and Parr reactor was added copper (I) chloride (5.0 mg; 0.051 mmol), methanol (100 mL) and 12-chloro-10-dodecenoate (5.00 g; 20.3 mmol). The reactor was removed from the glovebox, attached to an ammonia source, sparged with ammonia 3 times, and then pressurized to 100 psig with ammonia. The reaction mixture was stirred at 60° C. for 2 hours, cooled to room temperature, and the ammonia gas completely vented. The reaction mixture was partitioned between water and dichloromethane (1:1 v/v 300 mL) and the organic phase was separated. The aqueous phase was extracted with dichloromethane (2×70 mL). The combined organics were washed with brine and then dried with sodium sulfate. The organic phase was filtered through a fritted funnel and the organic solvent was evaporated under reduced pressure. The crude material was dissolved in diethyl ether (150 mL) and 10.1 mL of HCl (2M in diethyl ether) was added slowly to reaction mixture. The reaction mixture was stirred for 30 minutes, the precipitate filtered, and the precipitate was washed with diethyl ether (2×50 mL). The precipitate was re-dissolved in dichloromethane (150 mL) and stirred in saturated aqueous sodium bicarbonate solution. The organic phase was separated and the aqueous was extracted with dichloromethane (2×60 mL). The combined organic phase was washed with brine once and then dried with sodium sulfate. The organic was filtered and the solvent was evaporated to dryness to afford methyl, 12-amino-10-dodecenoate (3.6 g; 15.8 mmol; 78.3% yield). $^1$H NMR (400 MHz, CDCl$_3$) δ 1.16-1.28 (br s, 8H), 1.24-1.36 (m, 2H), 1.44 (s, 2H), 1.52-1.64 (m, 2H), 1.91-2.04 (m, 2H), 2.27 (t, J=7.5 Hz, 2H), 3.13-3.29 (m, 2H), 3.63 (s, 3H), 5.32-5.64 (m, 2H);

$^{13}$C NMR (101 MHz, CDCl$_3$) δ 24.9, 29.0, 29.0, 29.1, 29.2, 29.2, 32.2, 34.0, 44.0, 51.4, 130.8, 130.9, 174.2.

Methyl, 12-amino dodecanoate

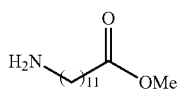

In an argon filled glovebox, a 40 mL glass liner equipped with a stir bar and Parr reactor was added 12-amino-10-dodecenoate (0.50 g, 2.2 mmol), Raney Nickel (6.2 mg; 0.22 mmol) and methanol (9.0 mL). The reaction mixture was sparged with hydrogen 3 times and then pressurized with hydrogen to 60 psig. The reaction was allowed to proceed at 60° C. for 9 hour. The reaction mixture was cooled to room temperature, the hydrogen completely vented, the reactor flushed with argon, and the crude was filtered through a plug of celite. The celite cake was washed with methanol (2×10 mL) and dichloromethane (2×5 mL). The combined organic layer was evaporated under reduced pressure to afford methyl, 12-amino-dodecanoate (500 mg; 2.18 mmol; 99% yield). $^1$H NMR (400 MHz, CDCl$_3$) δ 1.09-1.24 (br, 14H), 1.26-1.36 (m, 2H), 1.34 (s, 2H), 1.42-1.54 (m, 2H), 2.17 (t, J=7.5 Hz, 2H), 2.55 (t, J=7.0 Hz, 2H), 3.52 (s, 3H);

$^{13}$C NMR (101 MHz, CDCl$_3$) δ 24.6, 26.6, 28.8, 29.0, 29.1, 29.2, 29.2, 29.3, 33.4, 33.8, 41.9, 51.1, 173.9.

Synthesis of Dodecanoic Acid, 12-Oxo-, Methyl Ester

12-Hydroxydodecanoate compound is dissolved in buffered dichloromethane (0.2 M). Tetrabutylammonium bromide (0.05 eq), TEMPO (0.1 eq) and NCS (1.6 eq) are added portion wise. The reaction is monitored by TLC until complete. Brine is added and the organic layer is separated, dried with MgSO$_4$, concentrated and purified by column chromatography.

Synthesis of Dodecanoic Acid, 12-Amino-, Methyl Ester

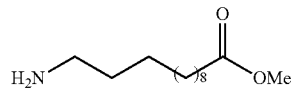

10-Dodecenoic acid-12-oxo-methyl ester or Dodecanoic acid-12-oxo-methyl ester in MeOH (0.4 M) is treated, with vigorous stirring, with ammonium formate (9 eq). After complete dissolution, 10% Pd/C (5.1 g, 4.8 mmol) is added and the reaction mixture is stirred overnight at room temperature. Upon completion of the reaction, the catalyst is filtered off on Celite and the solution is concentrated under reduced pressure. Product distributions are determined by GC.

Synthesis of 9-Dodecen-1-ol

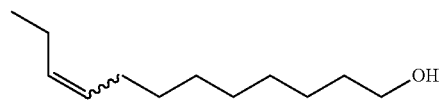

9-Dodecenyl acetate is added to a solution of potassium hydroxide (0.2 eq) in methanol (2.5 M) and stirred overnight at room temperature. The reaction mixture is subsequently partitioned between water and dichloromethane, the organic phase is separated and the aqueous phase is extracted with dichloromethane. The organic extracts are combined, dried over MgSO₄, filtered and the solvent is evaporated under reduced pressure providing the title compound.

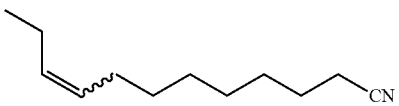

Synthesis of 9-Dodecenenitrile

A 2 L Parr reactor equipped with a glass liner and mechanical stirring is charged with copper catalyst (5.0 mol %), 2,2'-bipyridyl (5.0 mol %), TEMPO (5.0 mol %), acetonitrile (0.5 M), ammonium hydroxide (2 eq) and 9-dodecen-1-ol. The reactor is sealed and pressurized with compressed air (110 psi). The reactor is heated to 50° C. with stirring for 24 h. The reaction mixture is subsequently partitioned between water and hexanes, the organic phase is separated and the aqueous phase is extracted with hexanes. The organic extracts are combined, dried over MgSO₄, filtered and the solvent is evaporated under reduced pressure. 9-dodecenenitrile is purified by fractional distillation.

Synthesis of 2-Decenoic acid, 10-cyano-methyl ester

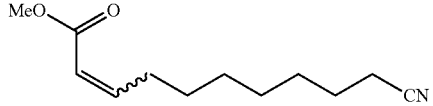 [SMILES: COC(=O)C=CCCCCCCCC#N]

A round bottom flask equipped with a magnetic stir bar is charged with 9-dodecenenitrile and methyl acrylate (1.5 eq) or ethyl crotonate (1.5 eq). The flask is fitted with a vacuum adapter and a rubber septum and placed under high vacuum before a group 8 transition metal complex metathesis catalyst is added by syringe. The reaction is stirred rapidly for 2 hours. The product is purified by column chromatography to afford the title compound.

Synthesis of 11-hydroxyundec-9-enenitrile

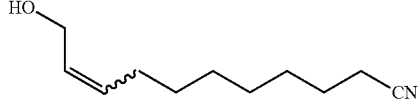 [SMILES: N#CCCCCCCCC=CCO]

An oven-dried round bottom flask equipped with a magnetic stir bar is charged with 9-dodecenenitrile and 1,4-diacetoxy-2-butene (1.5 eq). The flask is fitted with a vacuum adapter and a rubber septum and placed under high vacuum before a group 8 transition metal complex metathesis catalyst is added by syringe. The reaction is stirred rapidly for 2 hours then diluted with a solution of potassium hydroxide (0.2 eq) in methanol (2.5 M) and stirred overnight at room temperature. The reaction mixture is subsequently partitioned between water and dichloromethane, the organic phase separated and the aqueous phase extracted with dichloromethane. The organic extracts are combined, dried over MgSO₄, filtered and the solvent is evaporated under reduced pressure. The product is purified by column chromatography to afford the title compound.

Synthesis of Undecanoic Acid, 11-Amino-,Methyl Ester

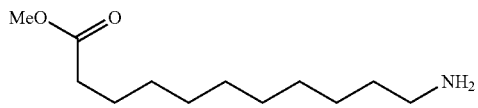 [SMILES: COC(=O)CCCCCCCCCCN]

A 60 mL Parr reactor equipped with a glass liner and magnetic stir bar is charged with methyl 2-Decenoic acid, 10-cyano-methyl ester, PtO₂ (15 mol %), acetyl chloride (1 eq), and methanol (0.05 M). The reactor is sealed and pressurized with hydrogen (20 bar). The reaction is stirred for 24 h at room temperature. Upon completion, the reaction mixture is then filtered through celite and the solvent is evaporated under reduced pressure. No further purification is required.

Synthesis of 11-Amino-1-Undecanol

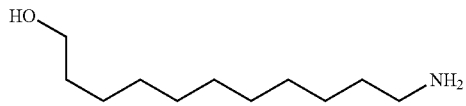 [SMILES: NCCCCCCCCCCCO]

A 60 mL Parr reactor equipped with a glass liner and magnetic stir bar is charged with methyl 2-Decenoic acid, 10-cyano-methyl ester, PtO₂ (15 mol %), acetyl chloride (1 eq), and methanol (0.05 M). The reactor is sealed and pressurized with hydrogen (20 bar). The reaction is stirred for 24 h at room temperature. Upon completion, the reaction mixture is then filtered through celite and the solvent is evaporated under reduced pressure. No further purification is required.

Synthesis of 11-Amino-Undecanoic Acid

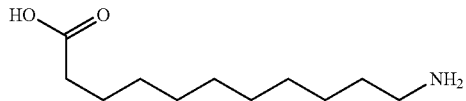 [SMILES: NCCCCCCCCCCC(=O)O]

A solution of amino-alcohol and triethylamine (1 eq) in THF (2.0 M) is cooled to 0° C., and di-tert-butyl dicarbonate (1 eq) is added portion wise. The mixture is stirred for 10 min, warmed to room temperature, and then stirred for 15 hours. The mixture is diluted with water, and extracted with diethyl ether. The organic layers are dried over MgSO₄ and then concentrated to give a crude product that is used without further purification. KBr (4.5 mol %) is dissolved in water. THF, AA-TEMPO (2.5 mol %), and Boc-amino-alcohol are added to the KBr solution with stirring. Sodium hypochlorite (11.5% aq. Solution, 6.5 eq) and NaOH (2 eq) are mixed and added to the reaction solution dropwise over a period of 1.5 h. At completion of the reaction, the mixture is acidified to pH 3.0 by of 1 N HCl. The resulting organic and aqueous are separated. The aqueous layer is extracted with THF and the combined THF layers are then concentrated to dryness to provide the title compound.

What is claimed is:

1. A process for synthesizing an amino acid or an amino acid derivative represented by the structure of Formula 1,

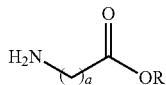

Formula 1 comprising the steps of:
(a) subjecting an olefinic substrate represented by the structure of Formula 2

Formula 2 to a cross metathesis reaction with a cross metathesis substrate represented by the structure of formula

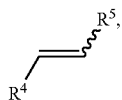

in the presence of at least one metal carbene olefin metathesis catalyst, to form an unsaturated protected alcohol intermediate represented by the structure of Formula 2a

Formula 2a (b) subjecting the unsaturated protected alcohol intermediate represented by the structure of Formula 2a to hydrolysis in basic conditions to yield an unsaturated alcohol represented by the structure of Formula 3

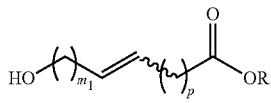

Formula 3 and;
(c) converting the unsaturated alcohol represented by the structure of Formula 3, to an amino acid or an amino acid derivative represented by the structure of Formula 1, by subjecting the unsaturated alcohol represented by the structure of Formula 3 to a tandem amination-reduction, wherein the tandem amination-reduction is carried out in the presence of a Ruthenium pincer complex represented by the structure of Formula 4:

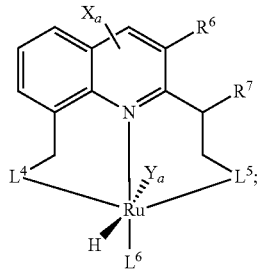

Formula 4 wherein: R is H, optionally substituted $C_1$-$C_{12}$ alkyl, optionally substituted $C_6$-$C_{10}$ aryl, optionally substituted heterocycle or optionally substituted $C_5$-$C_{10}$ cycloalkyl;

$R^1$ is —H, —$CH_3$ or —COOR;

$R^2$ is —$OR^3$;

$R^3$ is optionally substituted $CO(C_1$-$C_{12}$ alkyl), optionally substituted $CO(C_5$-$C_{10}$ cycloalkyl), optionally substituted $CO(C_6$-$C_{10}$ aryl), or optionally substituted $CO(C_5$-$C_{10}$ heterocycle);

$R^4$ is —H or —$(CH_2)_{m1}OR^3$; $R^5$ is —$(CH_2)_{m1}OR^3$;

a is 3, 4, 5, 6, 7, 8, 9, 10, 11, 12, 13, 14, 15, 16, 17, 18, 19, 20, 21, or 22;

m is 0, 1, 2, 3, 4, 5, 6, 7, 8, 9, 10, 11, 12, 13, 14, 15, 16, 17, 18 or 19;

$m_1$ is 1, 2, 3, 4, 5, 6, 7, 8, 9, 10, 11, 12, 13, 14, 15, 16, 17, 18 or 19;

p is 0, 1, 2, 3, 4, 5, 6, 7, 8, 9, 10, 11, 12, 13, 14, 15, 16, 17, 18 or 19;

$L^4$ and $L^5$ are each independently selected from the group consisting of phosphine ($PR^aR^b$), amine ($NR^aR^b$), imine, sulfide ($SR^d$), thiol (SH), sulfoxide ($S(=O)R^d$), heteroaryl containing at least one heteroatom selected from nitrogen and sulfur; arsine ($AsR^aR^b$), stibine ($SbR^aR^b$) and an N-heterocyclic carbene represented by the structures:

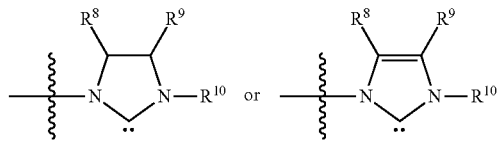

$L^6$ is a mono-dentate two-electron donor selected from the group consisting of CO, $PR^aR^bR^c$, $NO^+$, $AsR^aR^bR^c$, $SbR^aR^bR^c$, $SR^aR^b$, nitrile ($R^dCN$), isonitrile ($R^dNC$), $N_2$, $PF_3$, CS, heteroaryl, tetrahydrothiophene and N-heterocyclic carbene;

$R^6$ and $R^7$ are either each hydrogen or together with the carbons to which they are attached represent a phenyl ring which is fused to the quinolinyl moiety represented by the structure of Formula 4 so as to form an acridinyl moiety;

$R^a$, $R^b$, $R^c$, $R^d$, $R^8$, $R^9$ and $R^{10}$ are each independently alkyl, cycloalkyl, aryl, heterocyclyl, heteroaryl, alkylcycloalkyl, alkylaryl, alkylheterocyclyl or alkylheteroaryl;

$Y_a$ is a monoanionic ligand selected from the group consisting of halogen, $OCOR^d$, $OCOCF_3$, $OSO_2R^d$, $OSO_2CF_3$, CN, OH, $OR^d$, $NR^d_2$; a neutral solvent molecule $NH_3$, $NR_3$ and $R^d_2NSO_2R^d$, and when $Y_a$ is neutral, the whole molecule carries a positive charge;

$X_a$ represents one, two, three, four, five, six or seven substituents positioned at any carbon atom on the acridinyl moiety, or in the case where $R^6$ and $R^7$ together with the carbons to which they are attached represent a phenyl ring which is fused to the quinolinyl moiety represented by the structure of Formula 4; or one, two, three, four or five substituents positioned on any carbon atom on the quinolinyl moiety, or in the case where $R^6$ and $R^7$ are each hydrogen, and is selected from the group consisting of hydrogen, alkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support and a polymeric moiety; and with the proviso that the sum of any combination of $m_1$ and p is 1, 2, 3, 4, 5, 6, 7, 8, 9, 10, 11, 12, 13, 14, 15, 16, 17, 18, 19 or 20.

2. The process according to claim 1, wherein the at least one metal carbene olefin metathesis catalyst is a Group 8 transition metal complex.

3. The process according to claim 1, wherein the tandem amination-reduction is further carried out in the presence of ammonia and hydrogen.

4. The process according to claim 1, wherein the cross metathesis substrate represented by the structure of formula

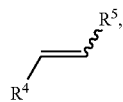

is 1,4-diacetoxy-2-butene.

5. The process according to claim 4, wherein the Ruthenium pincer complex represented by the structure of Formula 4 is Chlorocarbonylhydrido[4,5-bis-(di-i-propylphosphinomethyl)acridine] Ruthenium (II) or Chlorocarbonylhydrido[4,5-bis-(di-cyclohexylphosphinomethyl)acridine] Ruthenium (II).

6. The process according to claim 1, wherein R is H, optionally substituted $C_1$-$C_6$ alkyl, optionally substituted $C_6$ aryl, or optionally substituted $C_5$-$C_{10}$ cycloalkyl; $R^1$ is —H, —$CH_3$ or —COOR; $R^2$ is —$OR^3$; $R^3$ is optionally substituted CO($C_1$-$C_6$ alkyl), optionally substituted CO($C_5$-$C_{10}$ cycloalkyl), optionally substituted CO($C_6$ aryl); $R^4$ is —H or —($CH_2$)$_{m_1}$$OR^3$; $R^5$ is —($CH_2$)$_{m_1}$$OR^3$; a is 6, 7, 8, 9, 10, 11, 12, 13, 14, 15; 16 or 17; m is 0, 1, 2, 3, 4, 5, 6, or 7; $m_1$ is 1, 2, or 3; p is 3, 4, 5, 6, 7, 8, 9, 10, 11 or 12; and with the proviso that the sum of any combination of $m_1$ and p is 4, 5, 6, 7, 8, 9, 10, 11, 12, 13, 14 or 15.

7. The process according to claim 6, wherein R is H, optionally substituted $C_1$-$C_3$ alkyl; $R^1$ is —H, —$CH_3$ or —COOR; $R^2$ is —$OR^3$; $R^3$ is optionally substituted CO($C_1$-$C_3$ alkyl); $R^4$ is —H or —($CH_2$)$_{m_1}$$OR^3$; $R^5$ is —($CH_2$)$_{m_1}$$OR^3$; a is 9, 10, 11 or 12; m is 0, 1, 2, 3, 4, 5, 6 or 7; $m_1$ is 1 or 2; p is 6, 7 or 8.

8. The process according to claim 6, wherein R is $CH_3$; $R^1$ is H, $CH_3$ or COOR; $R^2$ is $OR^3$; $R^3$ is $CH_3$(CO)—; a is 9, 10, 11 or 12; m is 0, 1, 2, 3, 4, 5, 6 or 7; $m_1$ is 1 or 2; p is 6, 7 or 8; and the cross metathesis substrate represented by the structure of formula

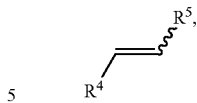

is 1,4-diacetoxy-2-butene.

9. The process according to claim 8, wherein a is 10; m is 0; $m_1$ is 1; and p is 7.

10. The process according to claim 8, wherein a is 11; m is 0; $m_1$ is 1; and p is 8.

11. The process according to claim 1, wherein: the cross metathesis substrate represented by the structure of formula

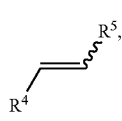

is 1,4-diacetoxy-2-butene; the at least one metal carbene olefin metathesis catalyst is [1,3-bis(2,6-di-isopropylphenyl)-2-imidazolidinylidene] dichloro (o-isopropoxyphenylmethylene)Ruthenium(II), [1,3-bis-(2,4,6-trimethyl phenyl-2-imidazolidinylidene]dichloro(o-isopropoxyphenyl methylene) Ruthenium (II), [1,3-bis-(2,4,6-trimethylphenyl)-2-imidazolidinylidene]dichloro(3-methyl-2-butenylidene) bis(pyridine)Ruthenium(II), or [1,3-bis-(2,4,6-trimethylphenyl)-2-imidazolidinylidene]dichloro(3-methyl-2-butenylidene) (tricyclohexylphosphine) Ruthenium(II); the Ruthenium pincer complex represented by the structure of Formula 4 is Chlorocarbonylhydrido[4,5-bis-(di-i-propylphosphinomethyl)acridine] Ruthenium (II) or Chlorocarbonylhydrido[4,5-bis-(di-cyclohexylphosphinomethyl)acridine] Ruthenium (II); R is $CH_3$; $R^1$ is H, $CH_3$ or COOR; $R^2$ is $OR^3$; $R^3$ is $CH_3$(CO)—; a is 9, 10, 11 or 12; m is 0, 1, 2, 3, 4, 5, 6 or 7; $m_1$ is 1 or 2; and p is 6, 7 or 8.

12. The process according to claim 11, wherein: the at least one metal carbene olefin metathesis catalyst is [1,3-bis(2,6-di-isopropylphenyl)-2-imidazolidinylidene]dichloro (o-isopropoxyphenylmethylene)Ruthenium(II); the Ruthenium pincer complex represented by the structure of Formula 4 is Chlorocarbonylhydrido[4,5-bis-(di-i-propylphosphino methyl)acridine] Ruthenium (II); R is $CH_3$; $R^1$ is H; $R^2$ is $OR^3$; $R^3$ is $CH_3$(CO)—; a is 10; m is 0; $m_1$ is 1; p is 7.

13. The process according to claim 11, wherein: the at least one metal carbene olefin metathesis catalyst is [1,3-bis(2,6-di-isopropylphenyl)-2-imidazolidinylidene]dichloro (o-isopropoxyphenylmethylene)Ruthenium(II); the Ruthenium pincer complex represented by the structure of Formula 4 is Chlorocarbonylhydrido[4,5-bis-(di-cyclohexyl phosphine methyl)acridine] Ruthenium (II); R is $CH_3$; $R^1$ is H; $R^2$ is $OR^3$; $R^3$ is $CH_3$(CO)—; a is 10; m is 0; $m_1$ is 1; p is 7.

14. The process according to claim 11, wherein: the at least one metal carbene olefin metathesis catalyst is [1,3-bis(2,6-di-isopropylphenyl)-2-imidazolidinylidene]dichloro (o-isopropoxyphenylmethylene)Ruthenium(II); the Ruthenium pincer complex represented by the structure of Formula 4 is Chlorocarbonylhydrido[4,5-bis-(di-i-propylphosphino methyl)acridine] Ruthenium (II); R is $CH_3$; $R^1$ is H; $R^2$ is $OR^3$; $R^3$ is $CH_3$(CO)—; a is 11; m is 0; $m_1$ is 1; and p is 8.

15. The process according to claim 11, wherein: the at least one metal carbene olefin metathesis catalyst is [1,3- bis(2,6-di-isopropylphenyl)-2-imidazolidinylidene]dichloro(o-isopropoxyphenylmethylene)Ruthenium(II); the Ruthenium pincer complex represented by the structure of Formula 4 is Chlorocarbonylhydrido[4,5-bis-(di-cyclohexylphosphinomethyl)acridine] Ruthenium (II); R is $CH_3$; $R^1$ is H; $R^2$ is $OR^3$; $R^3$ is $CH_3(CO)$—; a is 11; m is 0; $m_1$ is 1; and p is 8.

16. A process for synthesizing methyl 11-aminoundecanoate comprising the steps of
    (a) subjecting methyl 9-decenoate to a cross metathesis reaction with 1,4-diacetoxy-2-butene in the presence of [1,3-bis(2,6-di-isopropylphenyl)-2-imidazolidinylidene] dichloro(o-isopropoxyphenylmethylene)Ruthenium(II) to form methyl 11-acetoxy-9-undecenoate;
    (b) subjecting methyl 11-acetoxy-9-undecenoate to hydrolysis in basic conditions to form methyl 11-hydroxy-undecenoate; and
    (c) subjecting methyl 11-hydroxy-undecenoate to a tandem amination-reduction reaction in the presence of catalyst Chlorocarbonylhydrido[4,5-bis-(di-i-propylphosphinomethyl)acridine] Ruthenium (II) or Chlorocarbonylhydrido[4,5-bis-(di-cyclohexylphosphinomethyl)acridine] Ruthenium (II).

17. A process for synthesizing methyl 12-aminoundecanoate comprising the steps of
    (a) subjecting methyl 10-decenoate to a cross metathesis reaction with 1,4-diacetoxy-2-butene in the presence of [1,3-bis(2,6-di-isopropylphenyl)-2-imidazolidinylidene]dichloro(o-isopropoxyphenylmethylene)Ruthenium(II) to form methyl 12-acetoxy-10-undecenoate;
    (b) subjecting methyl 12-acetoxy-10-undecenoate to basic hydrolysis to form methyl 12-hydroxy-10-undecenoate; and
    (c) subjecting the methyl 12-hydroxy-10-undecenoate to a tandem amination-reduction reaction in the presence of catalyst Chlorocarbonylhydrido[4,5-bis-(di-i-propylphosphinomethyl)acridine] Ruthenium (II) or Chlorocarbonylhydrido[4,5-bis-(di-cyclohexylphosphinomethyl)acridine] Ruthenium (II).

18. The process according to claim 1, wherein step a) has a molar ratio of monomer to catalyst, in the range from about 1,000,000:1 to about 5,000:1.

19. The process according to claim 1, wherein step a) has a molar ratio of monomer to catalyst, in the range from about 200,00:1 to 66,667:1.

20. The process according to claim 1, wherein step a) has a molar ratio of monomer to catalyst, in the range from about 200,00:1, to 100,000:1.

* * * * *